US012653963B2

(12) United States Patent (10) Patent No.: US 12,653,963 B2
Daily et al. (45) Date of Patent: Jun. 16, 2026

(54) SAFETY NEEDLES AND METHODS OF USE THEREOF

(71) Applicants: David Daily, Herzliya (IL); Lior Raday, Kibbutz Bror-Hail (IL); Hagay Drori, Tel-Aviv (IL); Gad Lewkonya, Neve Mivtach (IL)

(72) Inventors: David Daily, Herzliya (IL); Lior Raday, Kibbutz Bror-Hail (IL); Hagay Drori, Tel-Aviv (IL); Gad Lewkonya, Neve Mivtach (IL)

(73) Assignee: Dali Medical Devices LTD., Yavne (IL)

( * ) Notice: Subject to any disclaimer, the term of this patent is extended or adjusted under 35 U.S.C. 154(b) by 589 days.

(21) Appl. No.: 17/986,904

(22) Filed: Nov. 15, 2022

(65) Prior Publication Data

US 2023/0076974 A1 Mar. 9, 2023

Related U.S. Application Data

(63) Continuation of application No. 15/771,100, filed as application No. PCT/IL2016/051189 on Nov. 3, 2016, now Pat. No. 11,529,473.

(Continued)

(51) Int. Cl.
    *A61M 5/178* (2006.01)
    *A61M 5/32* (2006.01)
    *A61M 5/31* (2006.01)
(52) U.S. Cl.
    CPC .......... *A61M 5/326* (2013.01); *A61M 5/3272* (2013.01); *A61M 5/3137* (2013.01);
    (Continued)

(58) Field of Classification Search
    CPC .. A61M 5/326; A61M 5/3272; A61M 5/3271; A61M 5/3275; A61M 5/3204;
    (Continued)

(56) References Cited

U.S. PATENT DOCUMENTS

2007/0129674 A1 6/2007 Liversidge
2011/0160675 A1 6/2011 Ruan
(Continued)

FOREIGN PATENT DOCUMENTS

WO 2001/91837 12/2001
WO 2014/010503 1/2014

*Primary Examiner* — Bhisma Mehta
*Assistant Examiner* — Tania Ismail
(74) *Attorney, Agent, or Firm* — Naomi S Rosenman-Helfand

(57) ABSTRACT

A needle protection assembly, adapted to protect a tip of a hypodermic needle, comprising a shield adapted, in a protected operative orientation of the needle protection assembly, to shield the tip of the hypodermic needle, a locking element including at least one slot, the slot including at least three surfaces corresponding to three operative orientations of the shield, at least one slot engaging element, functionally associated with the shield, the slot engaging element being disposed within the slot of the locking element and movable relative thereto, between the surfaces, so as to transition the shield between the three operative orientations, and at least one biasing element, adapted for axial biasing of the shield, wherein the three operative orientations include a storage operative orientation, an injection operative orientation, and a needle protection operative orientation.

20 Claims, 39 Drawing Sheets

Related U.S. Application Data

(60) Provisional application No. 62/393,144, filed on Sep. 12, 2016, provisional application No. 62/250,033, filed on Nov. 3, 2015.

(52) U.S. Cl.
    CPC ......... *A61M 5/3204* (2013.01); *A61M 5/3243* (2013.01); *A61M 2005/3247* (2013.01); *A61M 2005/3267* (2013.01); *A61M 5/3271* (2013.01); *A61M 5/3273* (2013.01); *A61M 5/3275* (2013.01)

(58) Field of Classification Search
    CPC ........ A61M 5/3273; A61M 2005/3267; A61M 2005/3247
    See application file for complete search history.

(56) References Cited

U.S. PATENT DOCUMENTS

| | | |
|---|---|---|
| 2013/0204196 A1 | 8/2013 | Roberts |
| 2015/0038903 A1 | 2/2015 | Jensen |
| 2015/0246182 A1 | 9/2015 | Evans |

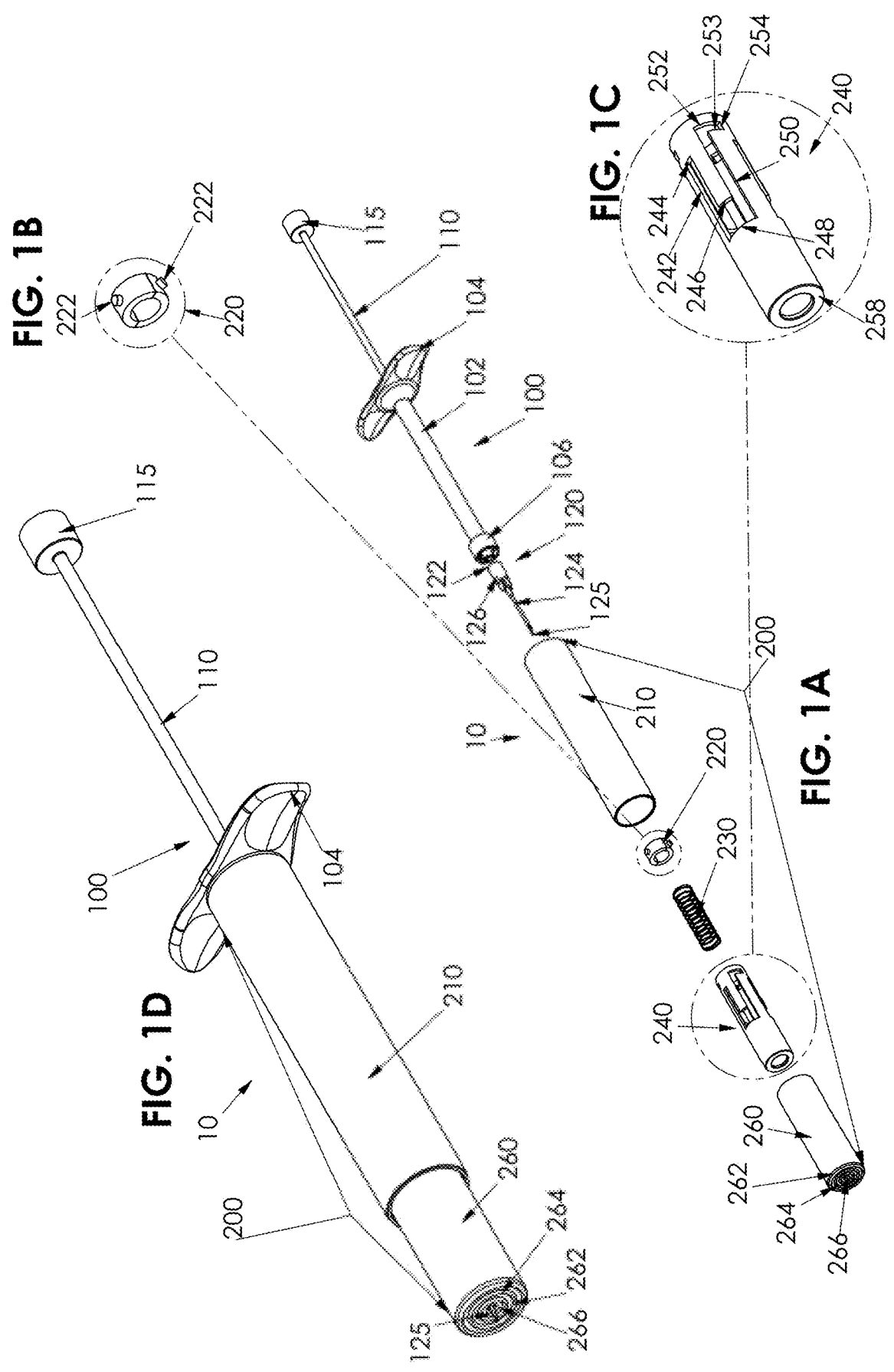

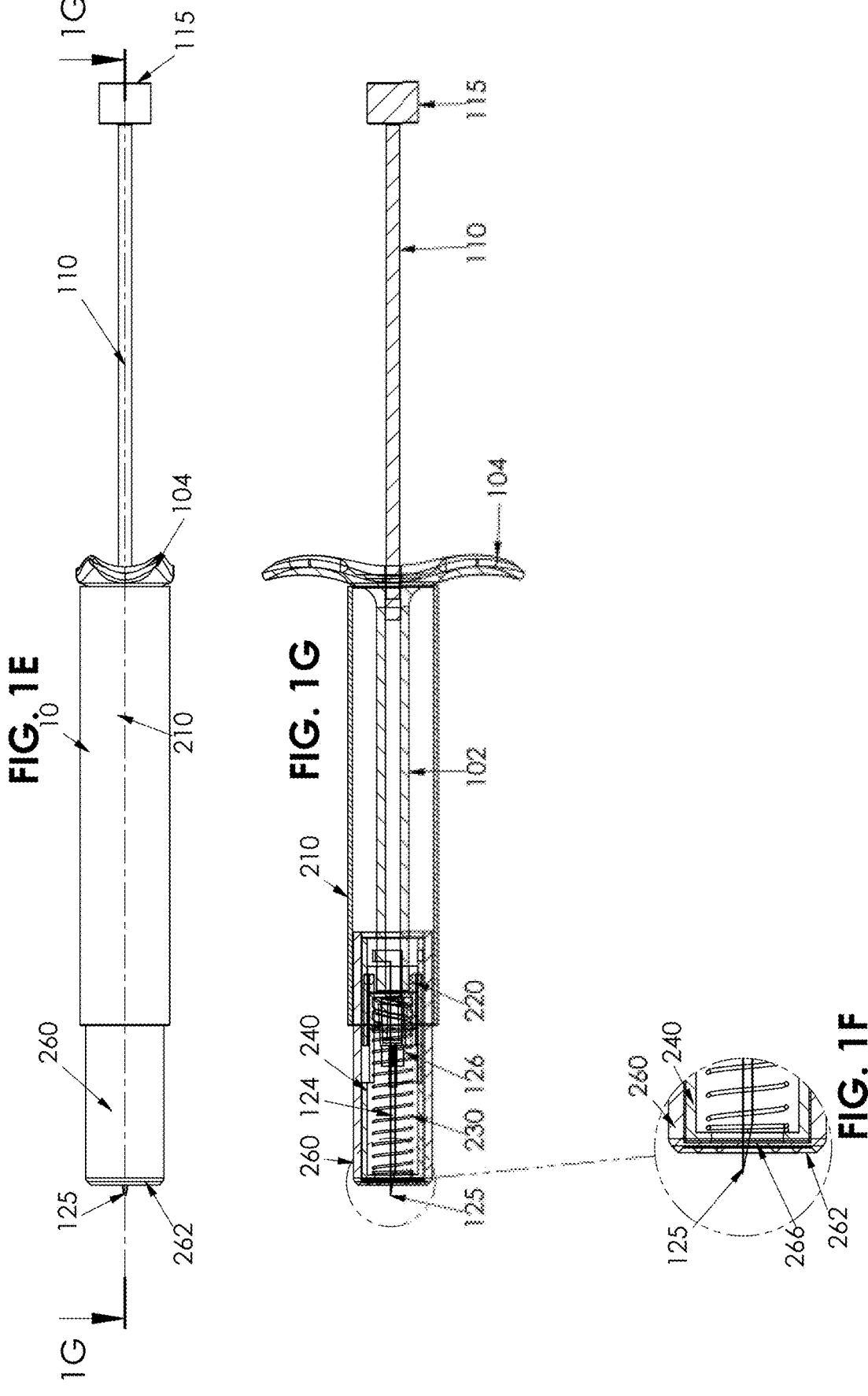

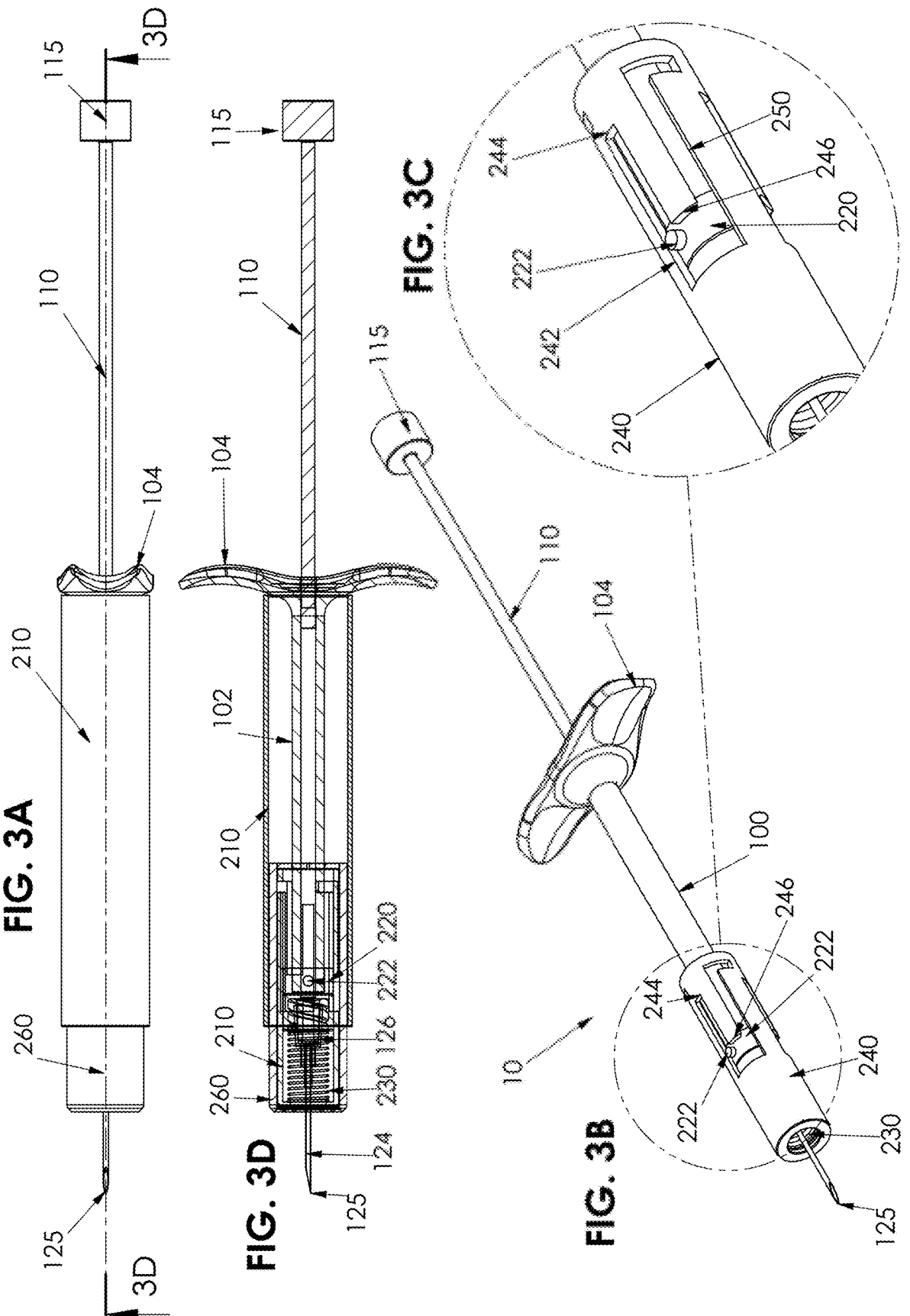

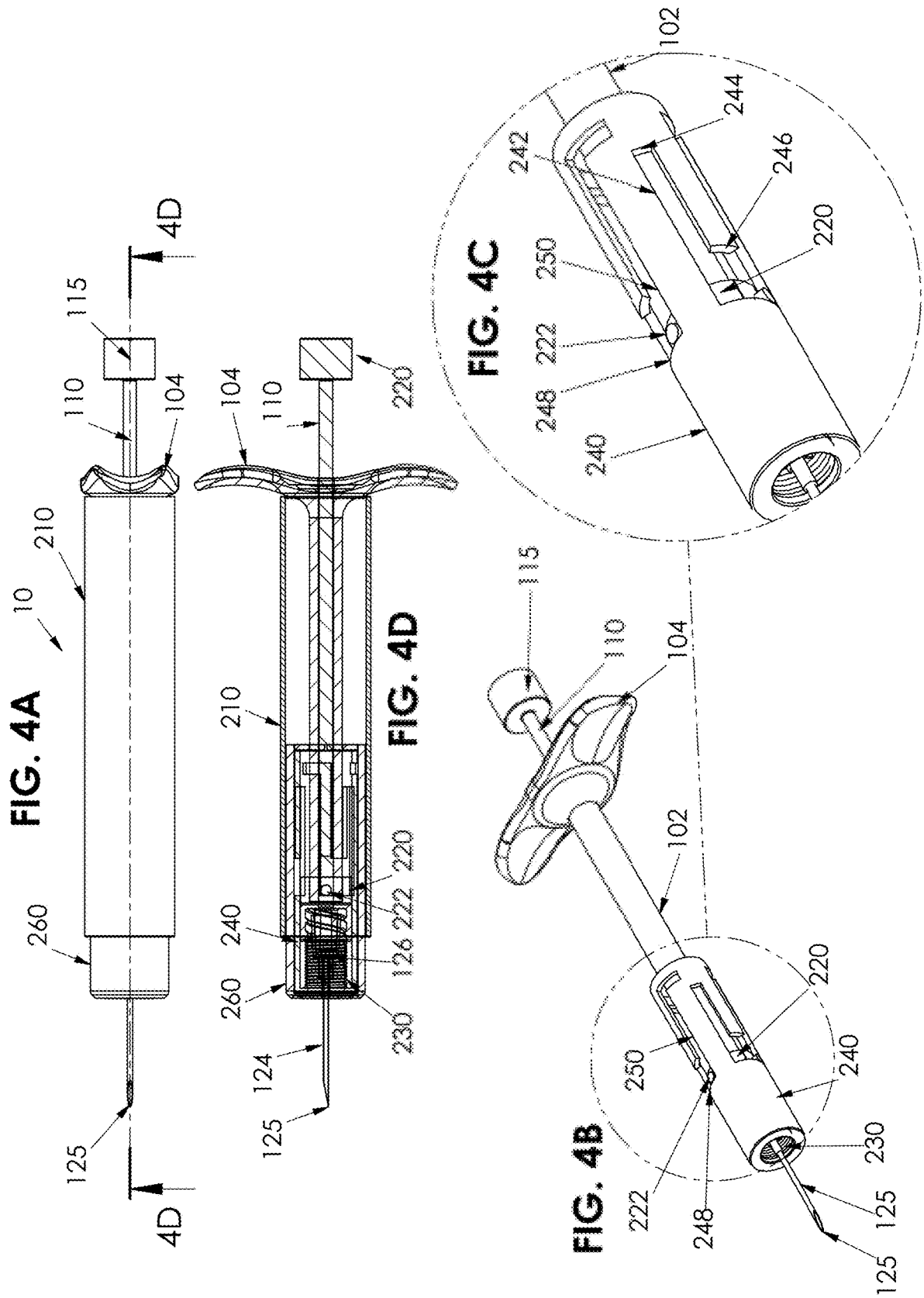

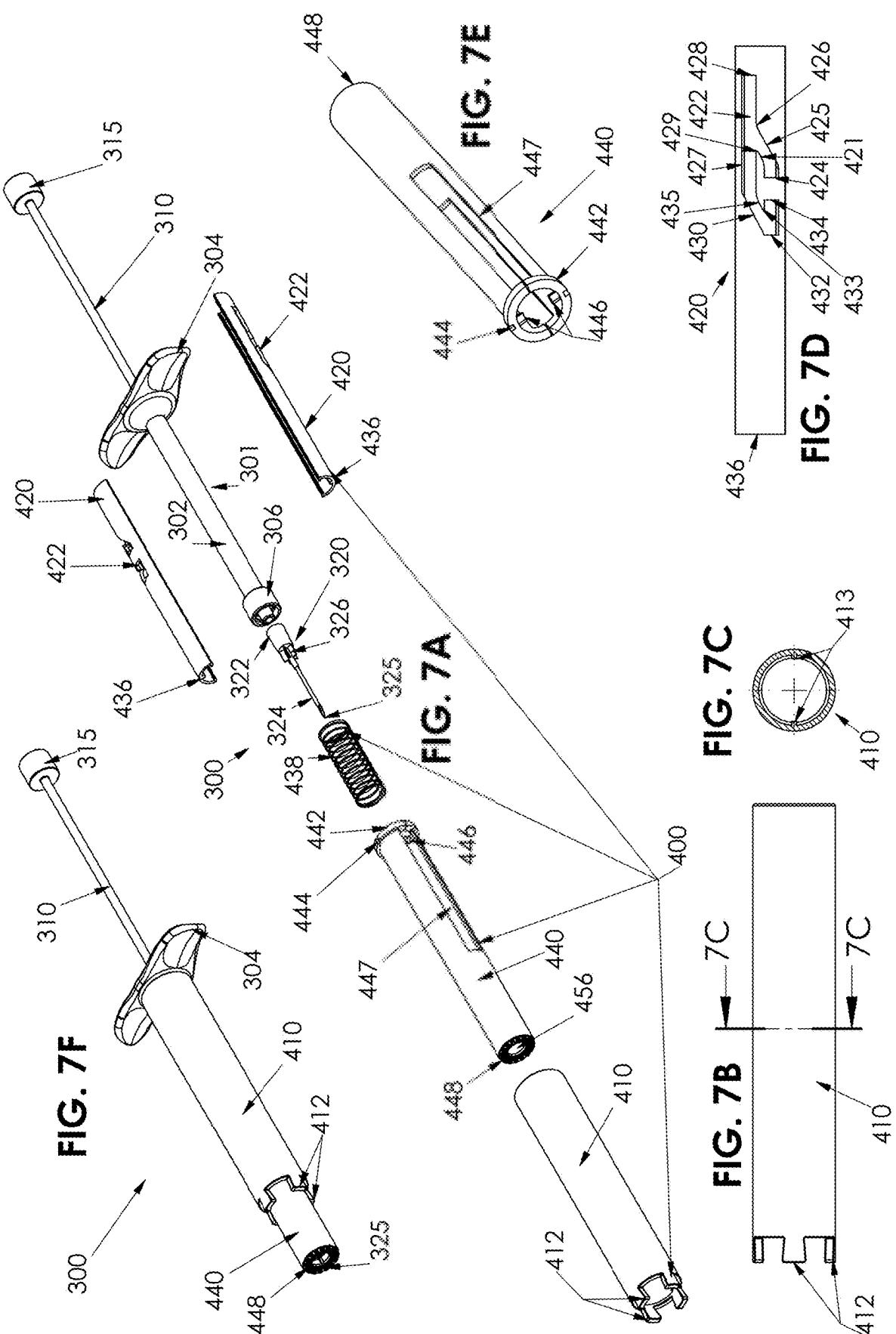

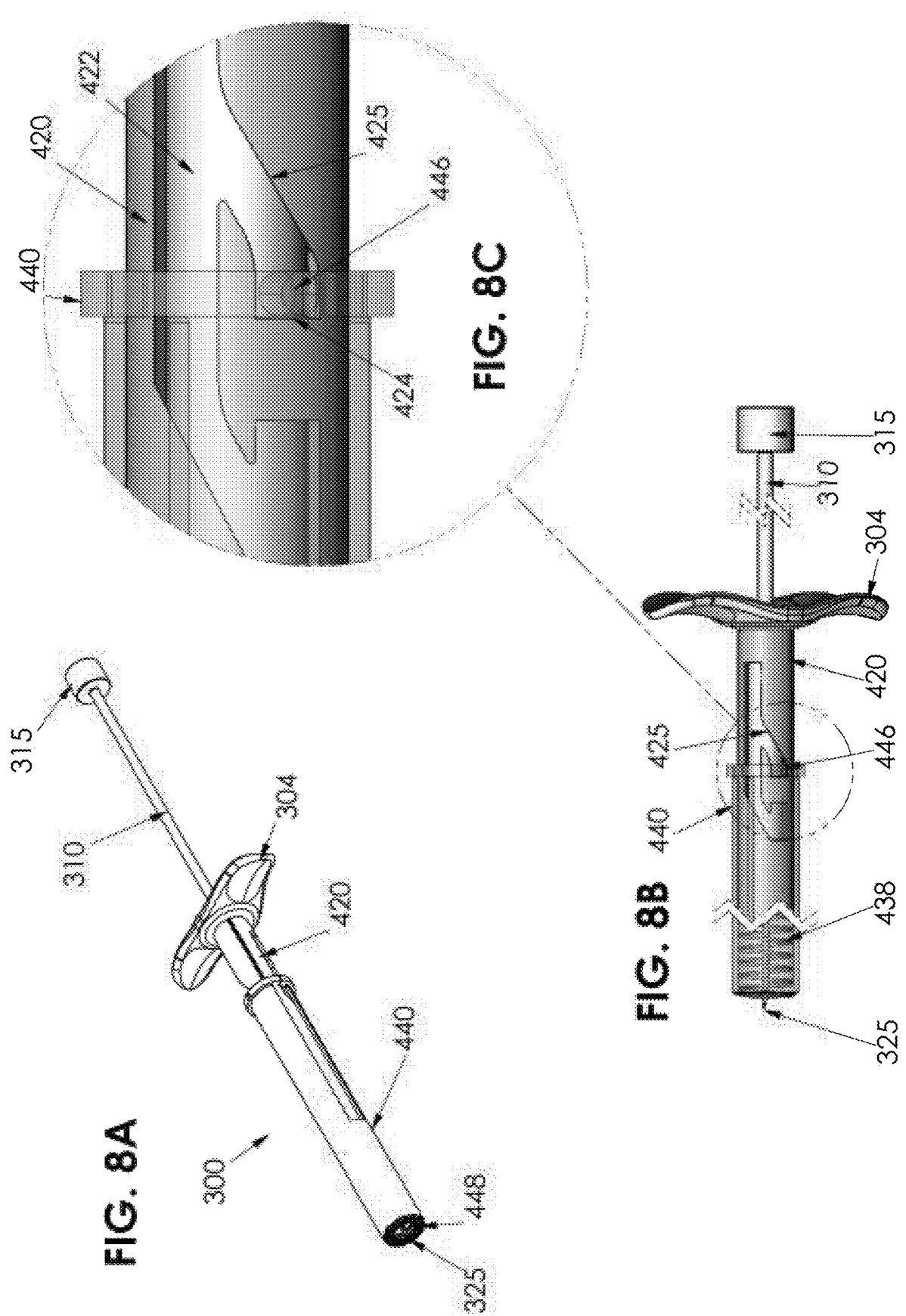

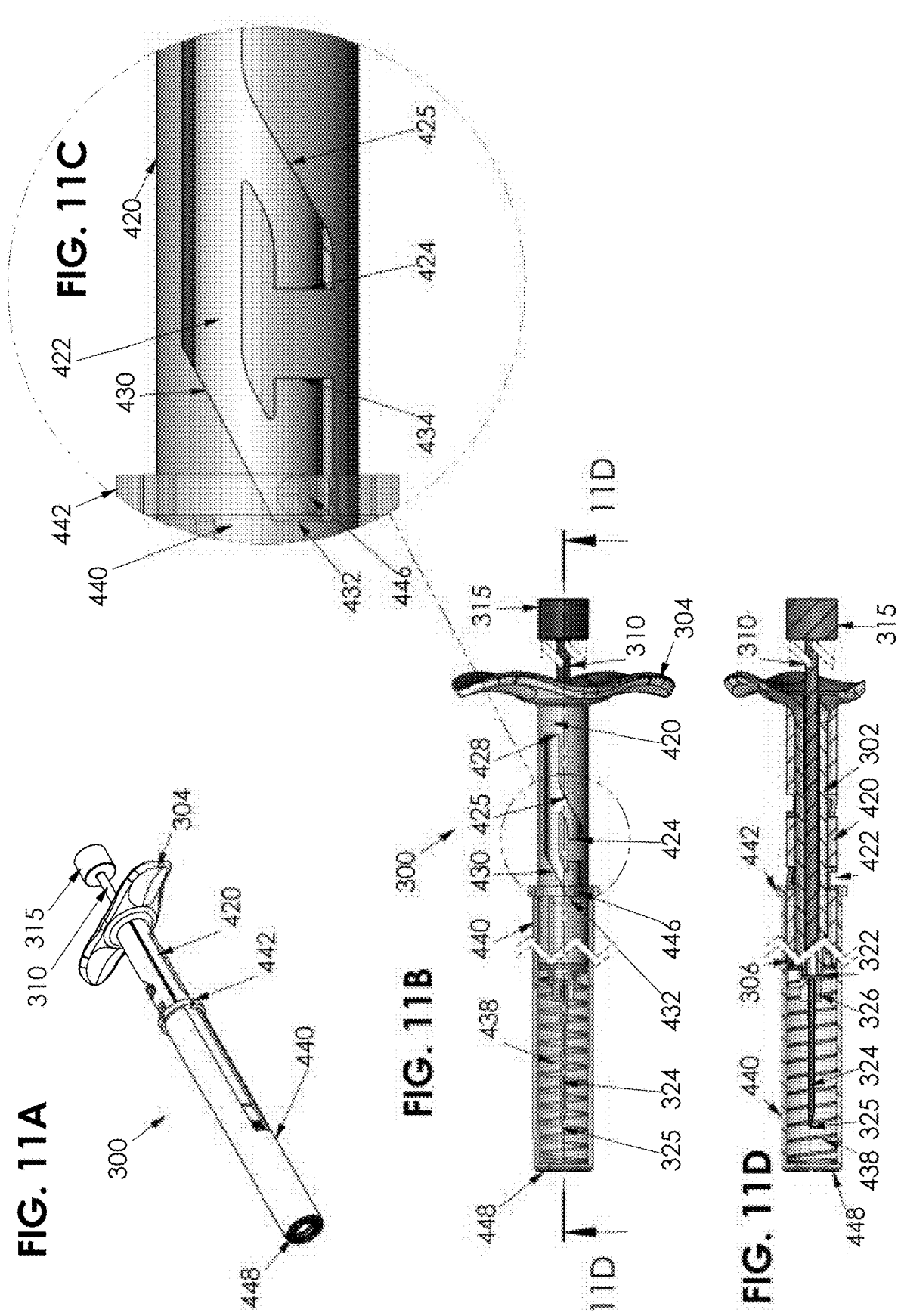

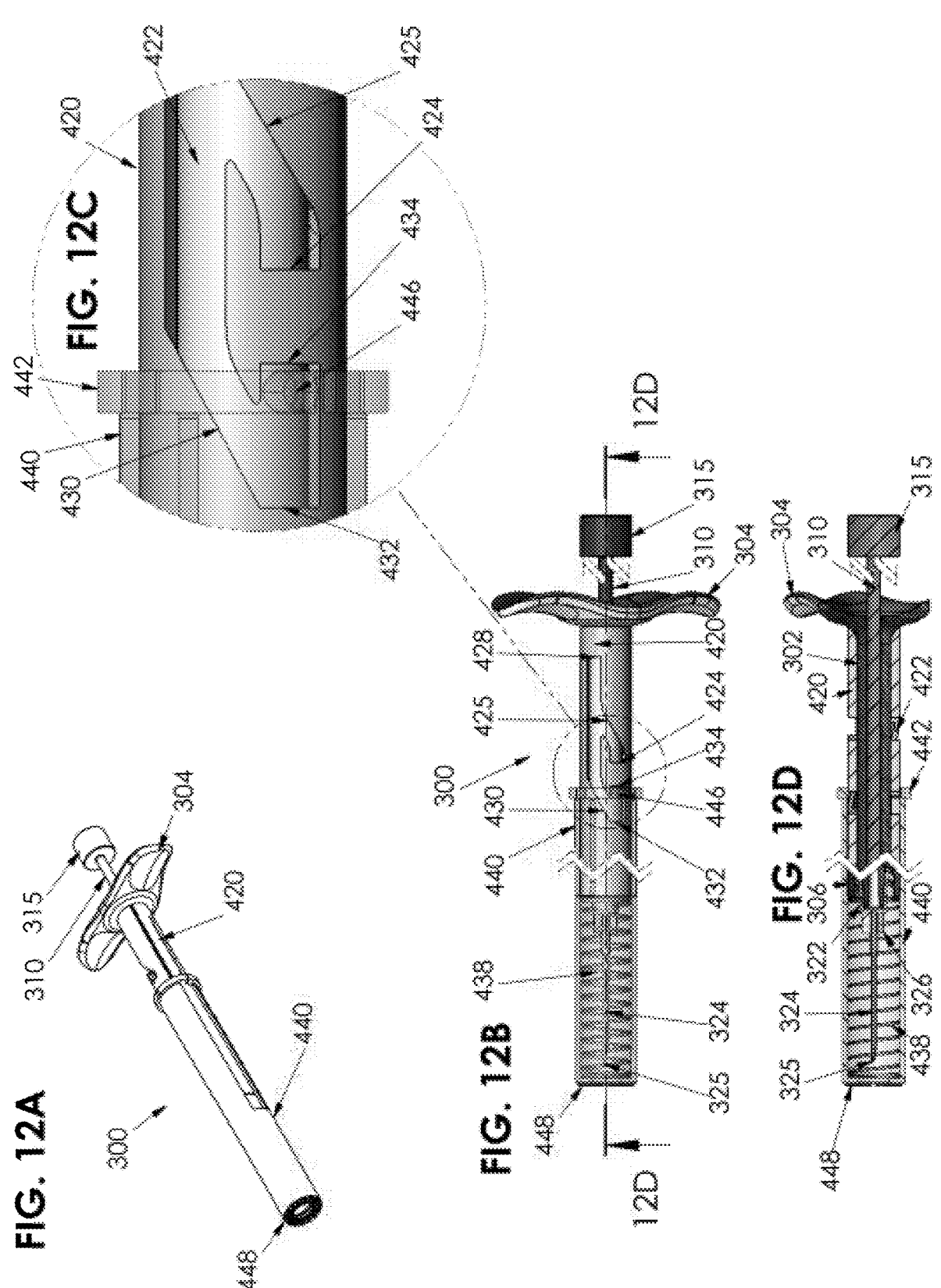

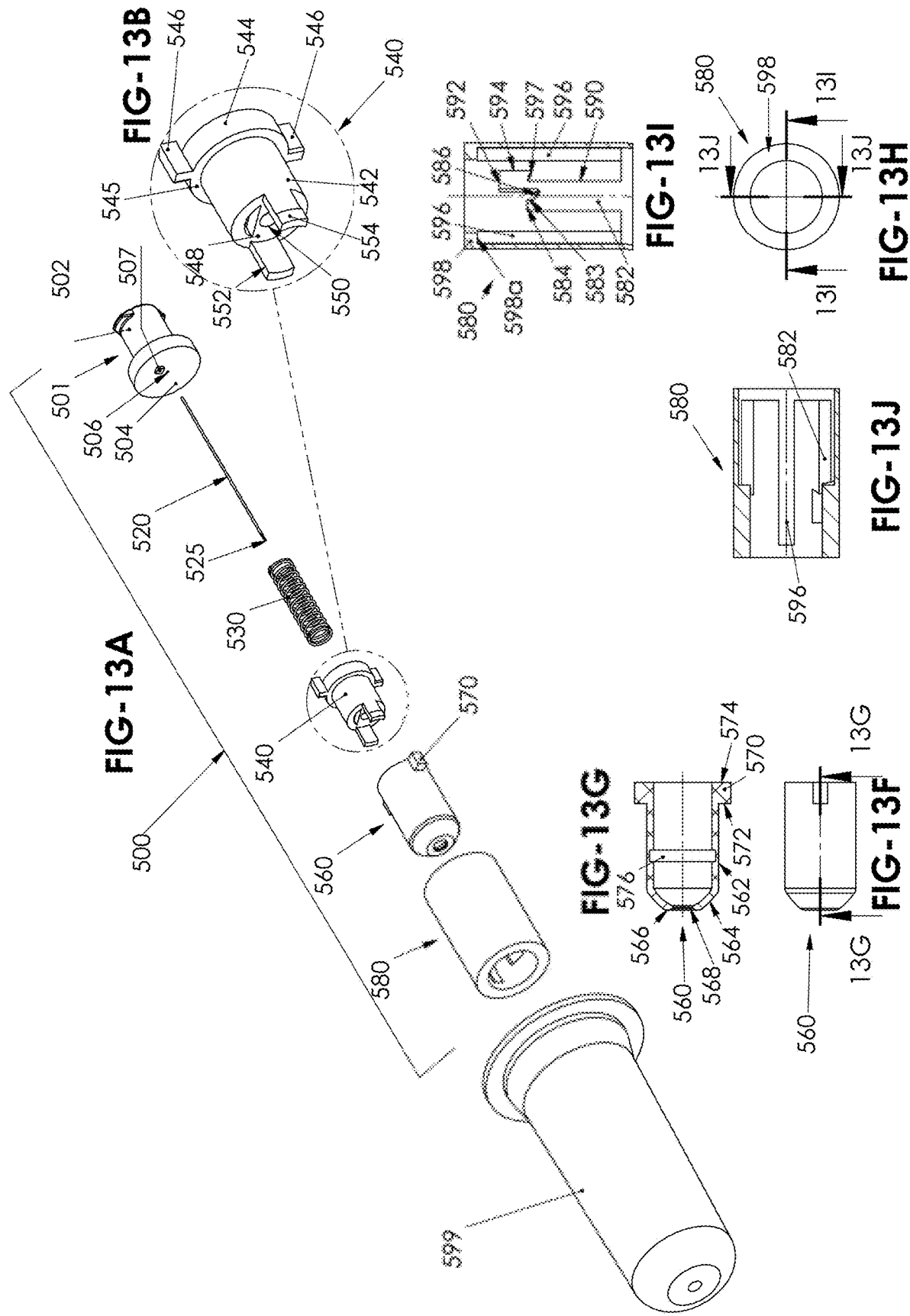

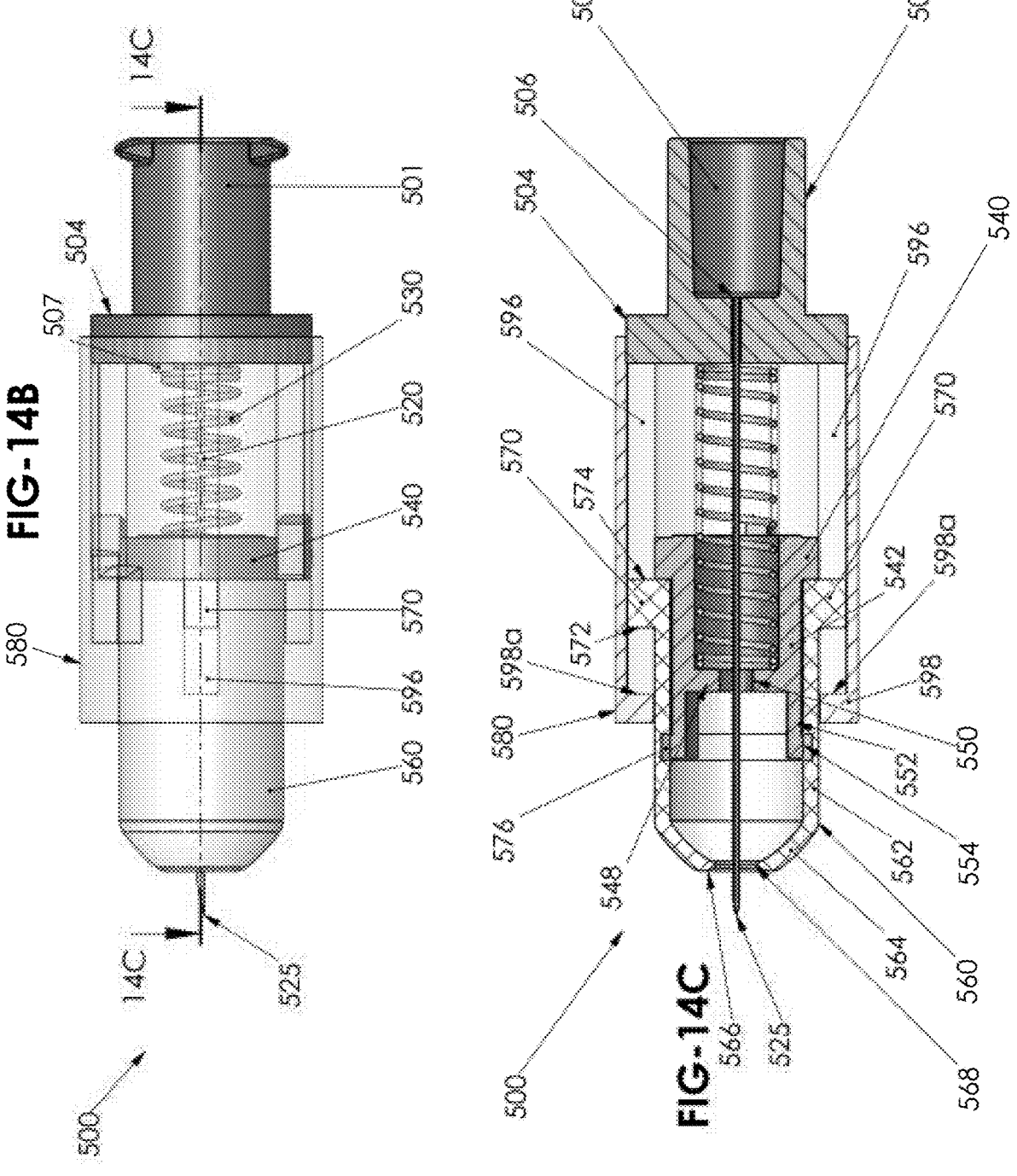

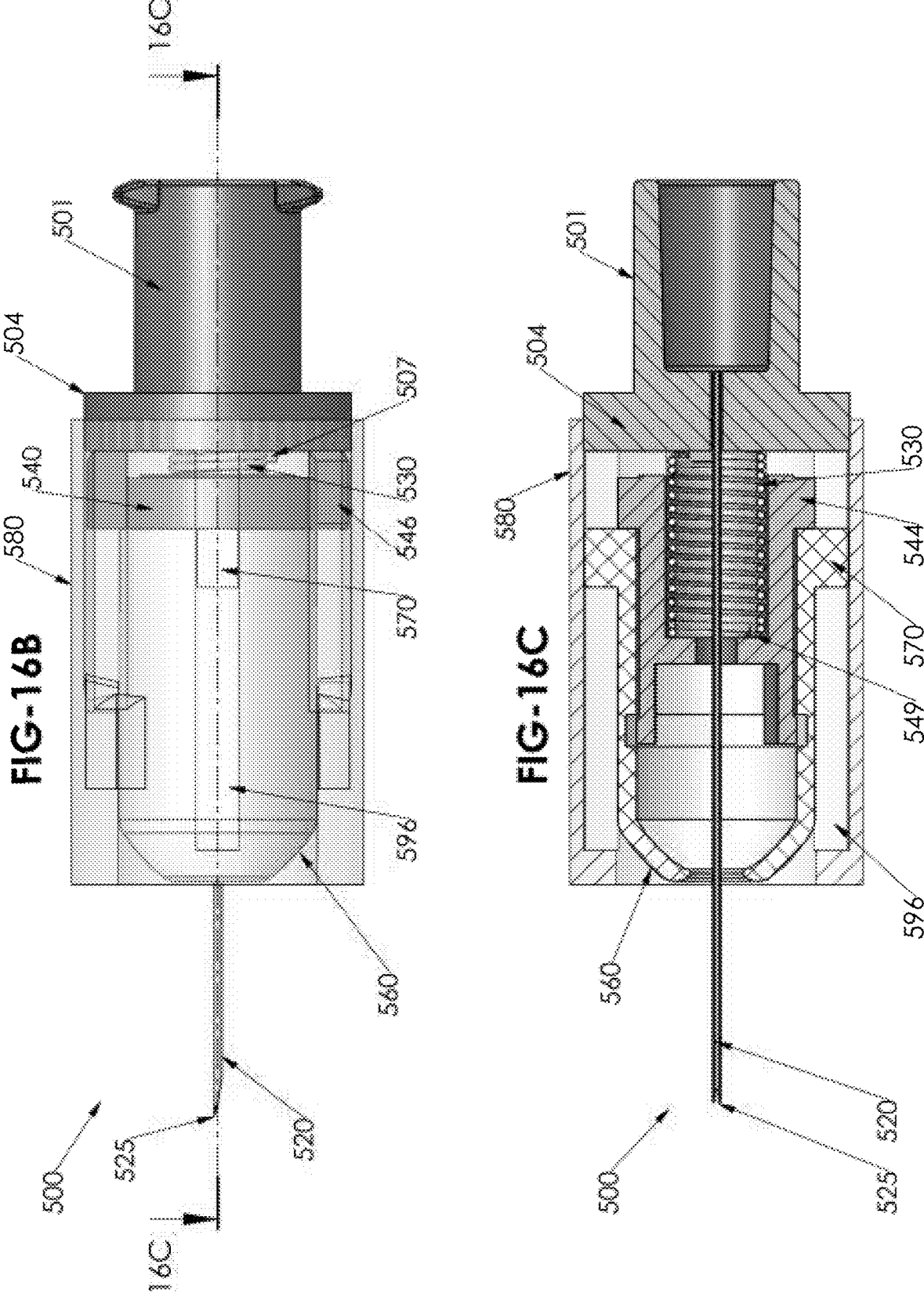

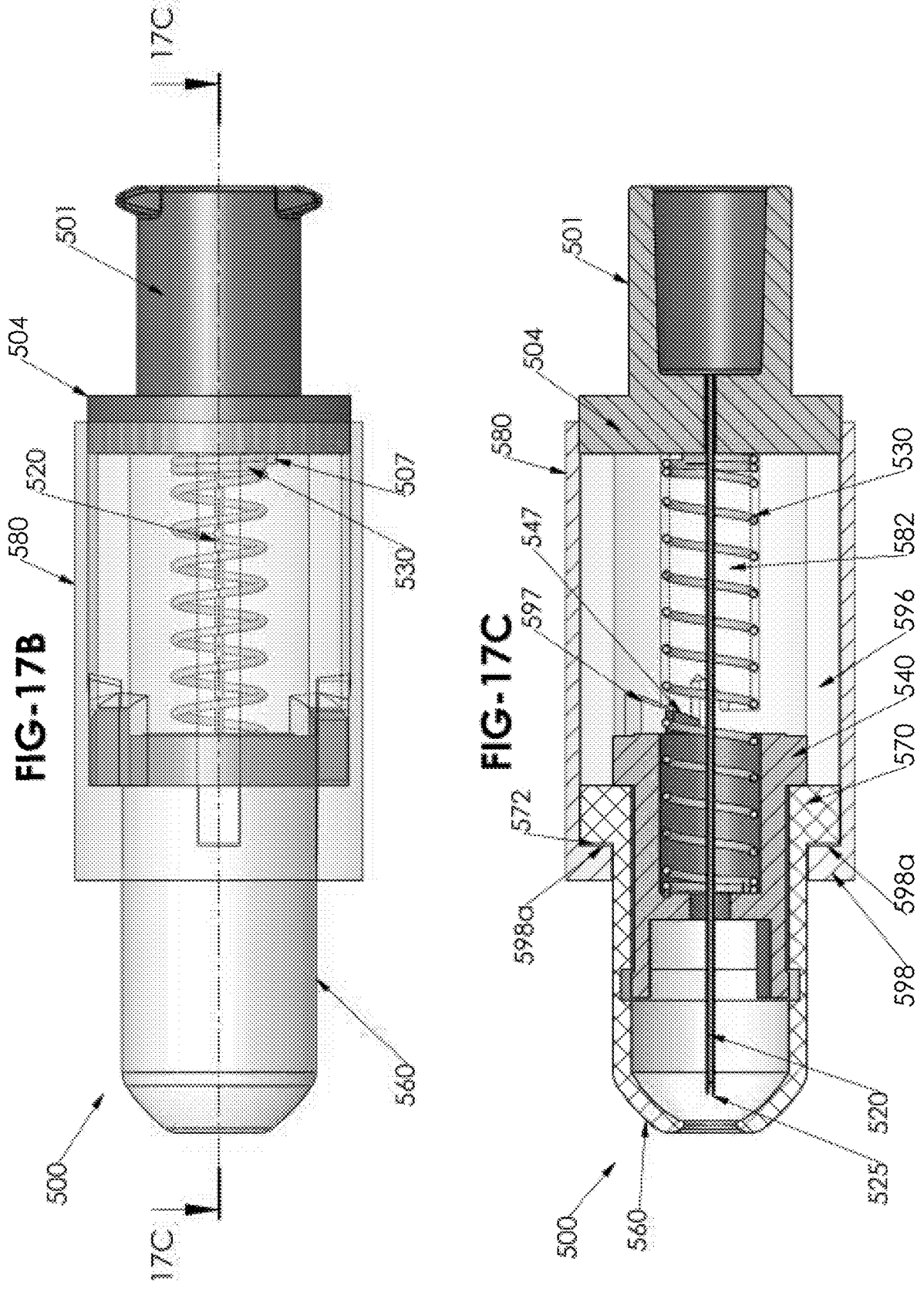

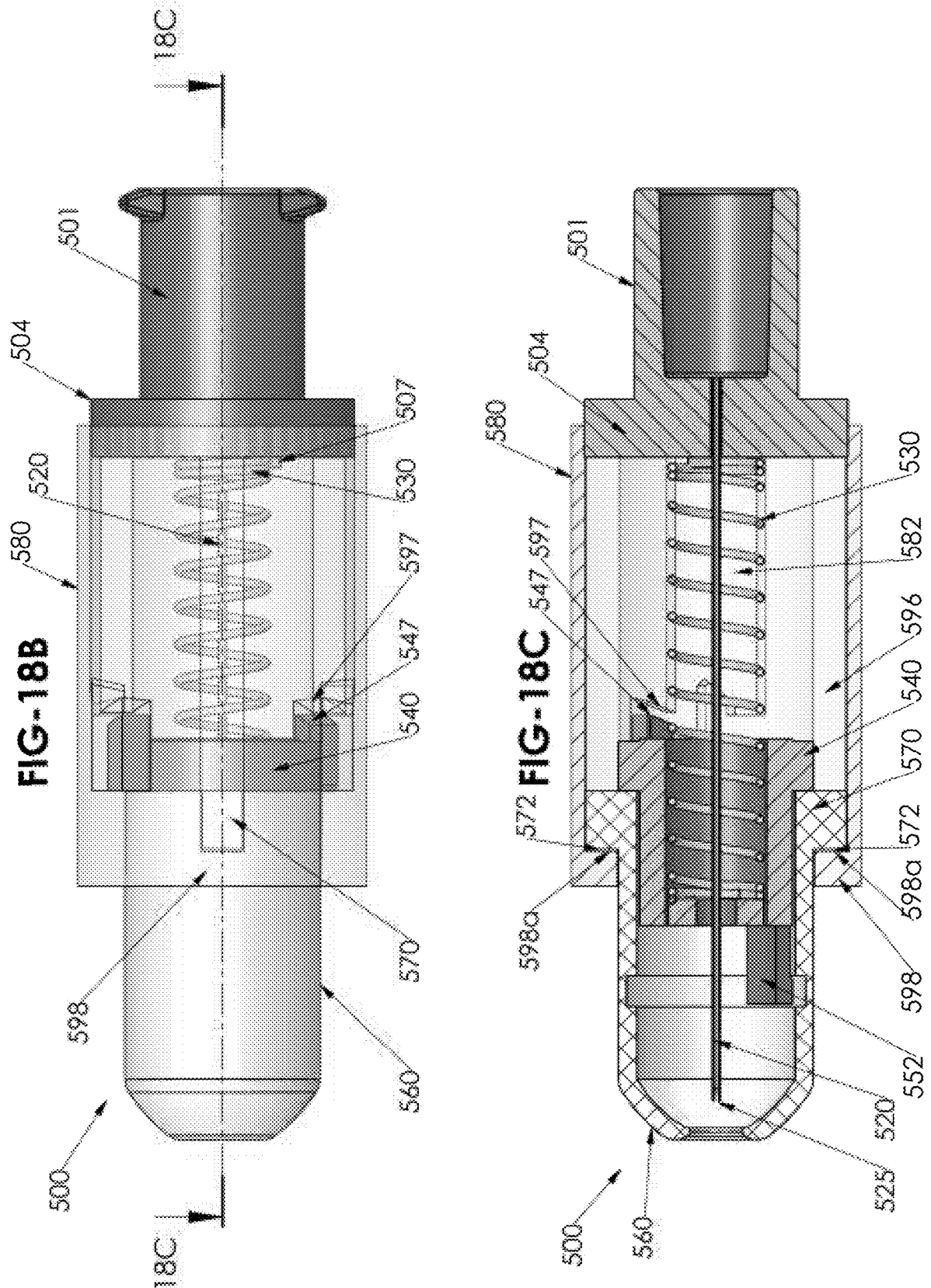

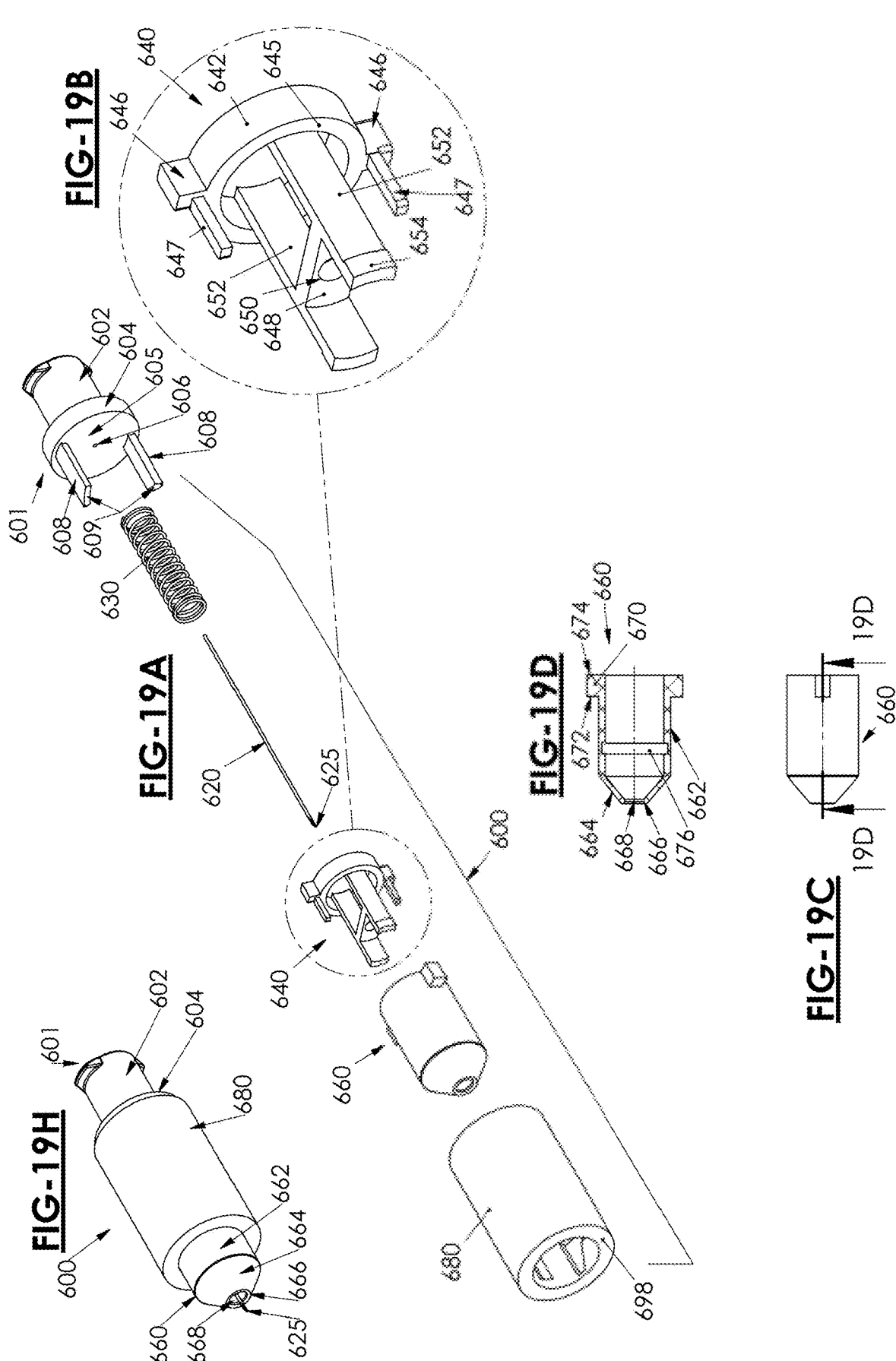

SAFETY NEEDLES AND METHODS OF USE THEREOF

FIELD AND BACKGROUND OF THE INVENTION

The invention, in some embodiments, relates to the field of injection devices, and more specifically to safety needles and/or to protection of needles which may be connected to a syringe.

SUMMARY OF THE INVENTION

In accordance with an aspect of the present invention, there is provided a needle protection assembly, adapted to protect a tip of a hypodermic needle, including:

a shield adapted, in a protected operative orientation of the needle protection assembly, to shield the tip of the hypodermic needle;

a locking element including at least one slot, the slot including at least three surfaces corresponding to three operative orientations of the shield;

at least one slot engaging element, functionally associated with the shield, the slot engaging element being disposed within the slot of the locking element and movable relative thereto, between the surfaces, so as to transition the shield between the three operative orientations; and at least one biasing element, adapted for axial biasing of the shield, wherein the three operative orientations include a storage operative orientation, an injection operative orientation, and a needle protection operative orientation.

In some embodiments, the slot engaging element includes a protrusion forming part of the shield. In some embodiments, the slot engaging element includes a protrusion formed on a locking ring, separate from the shield and functionally associated therewith. In some embodiments, the slot engaging element includes a protrusion formed on at least one of a hub of the hypodermic needle, an outer housing surrounding at least one of the hypodermic needle and the shield, and a barrel of a syringe functionally associated with the hypodermic needle.

In some embodiments, the locking ring further includes at least one flexible finger, wherein the flexible finger is not loaded in the storage operative orientation and receives a load during operation of the assembly, and wherein release of the load results in relative rotation between the locking element and the at least one slot engaging element thereby transitioning the assembly into the needle protection operative orientation.

In some embodiments, the biasing element includes a torsion force adapted for relative rotation between the at least one slot engaging element and the locking element. In some embodiments, the slot includes at least one inclined surface, such that when the slot engaging element engages the inclined surface there is relative rotation between the slot engaging element and the locking element. In some embodiments, the at least one slot engaging element rotates, thereby provide the relative rotation. In some embodiments, the locking element rotates, thereby provide the relative rotation.

In some embodiments, the slot includes an inclined locking surface and the slot engaging element includes a corresponding inclined surface, such that in the needle protection operative orientation the inclined locking surface of the slot engages the inclined surface of the slot engaging element, thereby increasing safety of locking between the slot engaging element and the slot.

In some embodiments, in the storage operative orientation, the tip of the hypodermic needle protrudes from the shield, in the injection operative orientation the hypodermic needle protrudes from the shield to a greater extent than in the storage position, and in the needle protection operative orientation the tip of the hypodermic needle is disposed within the shield and is locked therein.

In some embodiments, the at least three surfaces include a storage surface corresponding to the storage operative orientation, an end of press surface corresponding to the injection operative orientation, and a locking surface corresponding to the needle protection operative orientation, wherein the storage surface and the locking surface are at different positions along a longitudinal axis of the assembly.

In some embodiments, transition of the assembly from the storage operative orientation to the injection operative orientation is achieved by application of pressure to the biasing element, and wherein transition of the assembly from the injection operative orientation to the needle protection operative orientation is achieved by removal of pressure from the biasing element.

In some embodiments, the slot includes a triggering point, and wherein the transition of the assembly from the storage operative orientation to the injection operative orientation and to the needle protection operative orientation occurs only if the pressure applied to the biasing element is sufficient for pushing the slot engaging element past the triggering point.

In some embodiments, if the pressure applied to the biasing element is released prior to the slot engaging element passing the triggering point, the assembly returns to the storage operative orientation.

In some embodiments, the slot includes a one-way triggering passage terminating in the triggering point, the one-way triggering passage allows passage of the slot engaging element from the storage surface toward the triggering point, and once the slot engaging element has passed the triggering point, the one-way triggering passage blocks passage of the slot engaging element therein toward the storage surface.

In some embodiments, the slot includes a one-way locking passage terminating in the locking surface, the one-way locking passage allows passage of the slot engaging element from the end of press surface toward the locking surface, and once the slot engaging element has passed a locking point, the one-way locking passage blocks passage of the slot engaging element therein toward the end of press surface.

In some embodiments, the assembly further includes a connector for connection of the assembly to a container containing a fluid, and the hypodermic needle in fluid flow communication with the connector and disposed within the assembly at a radial center thereof, wherein, in the storage operative orientation, the tip of the needle protrudes from the shield, and in the needle protection operative orientation the tip of the needle is locked within the shield. In some embodiments, the assembly further includes a syringe connected to the connector as the container.

In accordance with some embodiments there is further provided a needle protection system, including a needle protection assembly as described herein, and a hypodermic needle integrally formed with or attached to a syringe, wherein the needle protection assembly is attached to the syringe such that the hypodermic needle is disposed within the assembly at a radial center thereof.

In some embodiments, the hypodermic needle is attached to or integrally formed with a syringe, the assembly further including a syringe attachment interface adapted for attachment of the assembly to the syringe, such that when the assembly is attached to the syringe, the hypodermic needle is disposed within the assembly at a radial center thereof.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures:

FIG. 1A is an exploded view illustration of a system for protection of a needle connected to a syringe according to a first embodiment of the teachings herein, the system including a safety needle device and a syringe;

FIG. 1B shows a detailed view of a guiding and locking ring forming part of the system of FIG. 1A;

FIG. 1C shows a detailed view of an internal sleeve forming part of the system of FIG. 1A;

FIG. 1D is a perspective view of the system of FIG. 1A, when constructed;

FIG. 1E is a planar side view illustration of the system of FIG. 1D;

FIG. 1F shows a detailed view of an exposed needle tip of the system of FIG. 1G;

FIG. 1G is a sectional illustration of the system of FIGS. 1A to 1E, taken along section lines 1G-1G in FIG. 1E;

FIG. 3A is a planar side view illustration of the system of FIGS. 1A to 1G, in a triggering operative orientation;

FIG. 3B is a perspective view illustration of the system of FIG. 3A, having the outer sleeve and external shield removed therefrom;

FIG. 3C shows a detailed view of a portion of the system of FIG. 3B;

FIG. 3D is a sectional illustration of the system of FIG. 3A, taken along section lines 3D-3D in FIG. 3A;

FIG. 4A is a planar side view illustration of the system of FIGS. 1A to 1G, in an injection operative orientation;

FIG. 4B is a perspective view illustration of the system of FIG. 4A, having the outer sleeve and external shield removed therefrom;

FIG. 4C shows a detailed view of a portion of the system of FIG. 4B;

FIG. 4D is a sectional illustration of the system of FIG. 4A, taken along section lines 4D-4D in FIG. 4A;

FIG. 7A is an exploded view illustration of a system for protection of a needle connected to a syringe according to a second embodiment of the teachings herein, the system including a safety needle device and a syringe;

FIG. 7B is a side view planar illustration of an outer sleeve forming part of the system of FIG. 7A;

FIG. 7C is a sectional illustration of the outer sleeve of FIG. 7B, taken along section lines 7C-7C in FIG. 7B;

FIG. 7D is a planar side view illustration of a locking tube forming part of the system of FIG. 7A;

FIG. 7E is an oriented view of a shield forming part of the system of FIG. 7A;

FIG. 7F is a perspective view of the system of FIG. 7A, when constructed;

FIG. 8A is a perspective view illustration of the system of FIGS. 7A and 7B, having an outer sleeve removed therefrom, in a storage operative orientation;

FIG. 8B is an oriented model view illustration of the system of FIG. 8A;

FIG. 8C is a detailed view of a portion of the system of FIG. 8B;

FIG. 11A is a perspective view illustration of the system of FIGS. 7A and 7B, having the outer sleeve removed therefrom, in a first locked operative orientation;

FIG. 11B is an oriented model view illustration of the system of FIG. 11A;

FIG. 11C is a detailed view of a portion of the system of FIG. 11B;

FIG. 11D is a sectional illustration of the system of FIG. 11B, the sectional illustration taken along section lines 11D-11D in FIG. 11B;

FIG. 12A is a perspective view illustration of the system of FIGS. 7A and 7B, having the outer sleeve removed therefrom, in a second locked operative orientation;

FIG. 12B is an oriented model view illustration of the system of FIG. 12A;

FIG. 12C is a detailed view of a portion of the system of FIG. 12B; and

FIG. 12D is a sectional illustration of the system of FIG. 12B, the sectional illustration taken along section lines 12D-12D in FIG. 12B;

FIG. 13A is an exploded view illustration of a system for protection of a needle connectable to a syringe according to a third embodiment of the teachings herein;

FIG. 13B shows a detailed view of a guiding and locking ring forming part of the system of FIG. 13A;

FIG. 13F is a side view planar illustration of a shield forming part of the system of FIG. 13A;

FIG. 13G is a sectional illustration of the shield of FIG. 13F, the sectional illustration being taken along section lines 13G-13G in FIG. 13F;

FIG. 13H is a front view planar illustration of an outer sleeve forming part of the system of FIG. 13A;

FIGS. 13I and 13J are sectional illustrations of the outer sleeve, the sectional illustrations taken along respective section lines 13I-13I and 13J-13J in FIG. 13H;

FIG. 14B is a model side view planar illustration of the system of FIG. 14A;

FIG. 14C is a sectional illustration of the system of FIG. 14A, taken along section lines 14C-14C in FIG. 14B;

FIG. 16B is a model side view planar illustration of the system of FIG. 16A;

FIG. 16C is a sectional illustration of the system of FIG. 16A, taken along section lines 16C-16C in FIG. 16B;

FIG. 17B is a model side view planar illustration of the system of FIG. 17A;

FIG. 17C is a sectional illustration of the system of FIG. 17A, taken along section lines 17C-17C in FIG. 17B;

FIG. 18B is a model side view planar illustration of the system of FIG. 18A;

FIG. 18C is a sectional illustration of the system of FIG. 18A, taken along section lines 18C-18C in FIG. 18B;

FIG. 19A is an exploded view illustration of a system for protection of a needle connectable to a syringe according to a fourth embodiment of the teachings herein;

FIG. 19B shows a detailed view of a guiding and locking ring forming part of the system of FIG. 19A;

FIG. 19C is a side view planar illustration of a shield forming part of the system of FIG. 19A;

FIG. 19D is a sectional illustration of the shield of FIG. 19C, the sectional illustration being taken along section lines 19D-19D in FIG. 19C;

FIG. 19H is a perspective view of the system of FIG. 19A, when constructed;

DESCRIPTION OF SOME EMBODIMENTS OF THE INVENTION

Figures 2A, 2B, 2C, 2D:
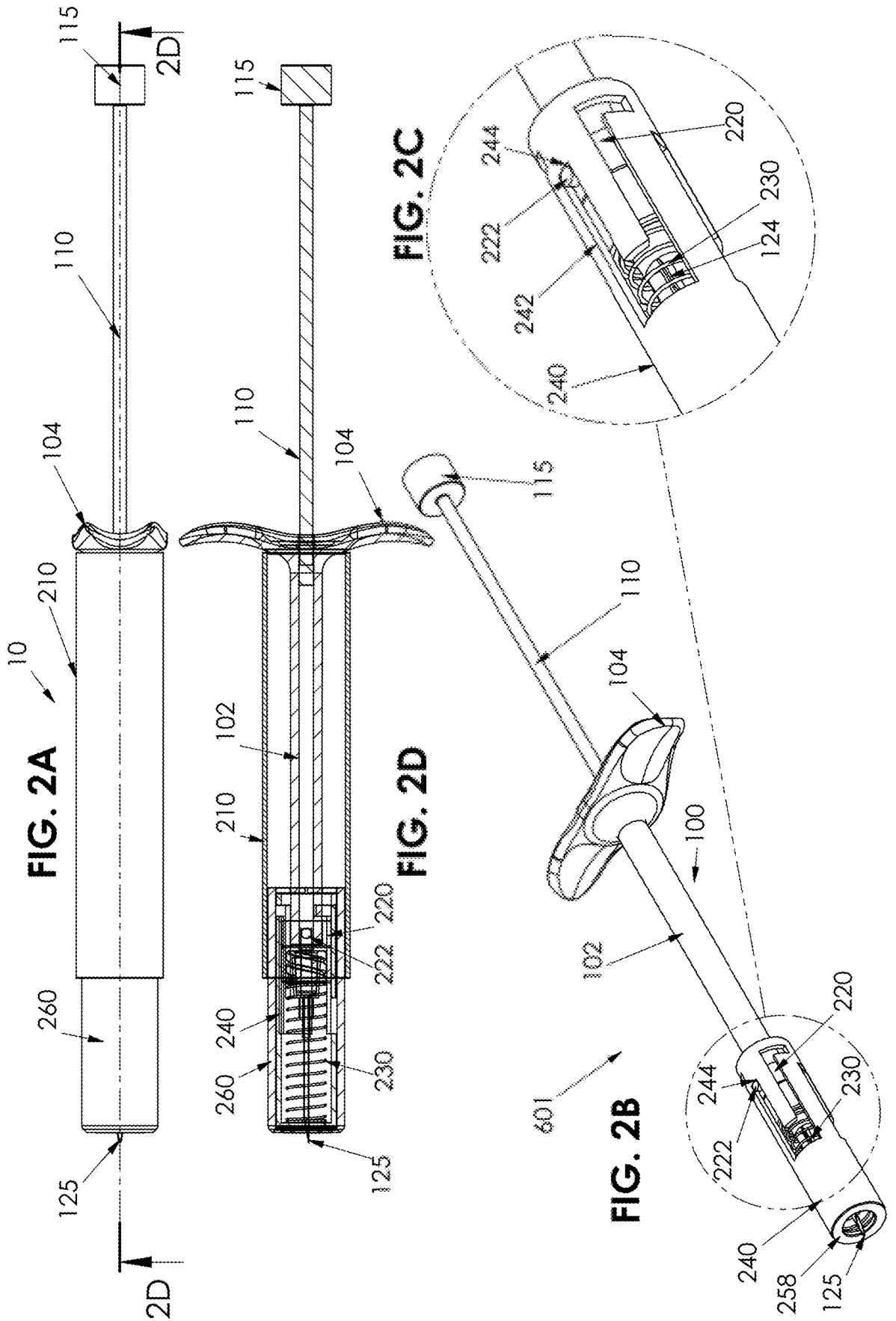
FIG. 2A is a planar side view illustration of the system of FIGS. 1A to 1G, in a storage operative orientation.
FIG. 2B is a perspective view illustration of the system of FIG. 2A, having an outer sleeve and an external shield removed therefrom.
FIG. 2C shows a detailed view of a portion of the system of FIG. 2B.
FIG. 2D is a sectional illustration of the system of FIG. 2A, taken along section lines 2D-2D in FIG. 2A.

The invention, in some embodiments, relates to the field of injection devices, and more specifically to protection of a needle connected or connectable to a syringe.

The principles, uses and implementations of the teachings herein may be better understood with reference to the accompanying description and figures. Upon perusal of the description and figures present herein, one skilled in the art is able to implement the invention without undue effort or experimentation.

Before explaining at least one embodiment of the invention in detail, it is to be understood that the invention is not limited in its applications to the details of construction and the arrangement of the components and/or methods set forth in the following description and/or illustrated in the drawings. The invention can be implemented with other embodiments and can be practiced or carried out in various ways. It is also understood that the phraseology and terminology employed herein is for descriptive purpose and should not be regarded as limiting.

In the context of the present application, the terms "forward", "forwardly", and "front" relate to the direction of the needle tip, or to elements that are closer to the needle tip, and the terms "rearward" and "rearwardly" relate to the direction away from the needle tip, or to elements that are farther from the needle tip.

Reference is now made to FIG. 1A, which is an exploded view illustration of a system 10 for protection of a needle connected to a syringe according to a first embodiment of the teachings herein, the system including a safety needle device and a syringe.

As seen in FIG. 1A, the system 10 includes a syringe 100, which may include a hollow barrel 102 terminating at a rearward end thereof in a flange 104, and at a forward end thereof in a luer lock 106, which is typically a male luer lock, and which is adapted to connect to a needle as described herein. A plunger 110 terminating at a plunger flange 115 is adapted to be disposed within barrel 102, and to be movable therein, as known in the art.

A hypodermic needle 120, which may be any needle known in the art, includes a luer lock 122, which is typically a female luer lock. A needle 124, terminating in a sharp needle tip 125, is in fluid communication with luer lock 122 via a needle hub 126.

A needle protection assembly 200 includes a generally tubular outer sleeve 210, a guiding and locking ring 220, a compression spring 230, which in some embodiments is also a torsion spring, an internal sleeve 240, and an external shield 260. While spring 230 is illustrated and described herein as a compression spring, the system may be designed to use any other suitable biasing element, such as a tension spring, a constant-force spring, an integrally formed plastic spring, or any other resilient element such as a rubber, plastic or elastomeric element.

As seen clearly in FIG. 1B, which shows a detailed view of guiding and locking ring 220 forming part of needle protection assembly 200 of system 10, the ring 220 is hollow, and has formed on an exterior surface thereof at least one guiding pin 222, here illustrated as three guiding pins. In some embodiments (not illustrated), locking ring 220 may be integrally formed as part of the needle hub 126 of hypodermic needle 120, as part of barrel 102 of syringe 100, or as part of outer sleeve 210, with suitable changes to the direction of pins 222.

Turning to FIG. 1C, which shows a detailed view of internal sleeve 240 forming part of assembly 200 of system 10, the internal sleeve is generally tubular, and includes, in a rearward portion thereof, a throughgoing slot 242. As explained in further detail hereinbelow, slot 242 includes multiple surfaces which define the stages of operation of needle protection assembly 200, the maximal needle penetration depth, and the protection depth. Specifically, slot 242 includes a storage surface 244, a triggering surface 246, an end of press surface 248, a torque limiting surface 250, a rearward protection surface 252, a forward protection surface 253, and a locking surface 254. At a forward end thereof, internal sleeve 240 terminates in a rim 258.

External shield 260 is hollow and generally tubular, and terminates at a forward facing end thereof in a skin engaging surface 262. Skin engaging surface 262 may be textured, for example by rings 264, and includes at the center thereof an opening 266 for passage of a needle therethrough.

External shield 260 may be designed as in the illustrated embodiment, such that it can rotate about its longitudinal axis. Alternately, external shield 260 may be designed such that rotation about the longitudinal axis thereof would be mechanically prevented, for example by longitudinal guiding ribs (not shown) which may be formed on the external shield 260 and disposed within corresponding slots (not shown) on outer sleeve 210, or vice versa, or by having guiding pins 222 of locking ring 220 protrude sufficiently so as to also engage slots (not shown) which may be formed on external shield 260.

The construction of system 10 will now be explained making additional reference to FIG. 1D, which is a perspective view of the system 10, when constructed, to FIG. 1E, which is a planar side view illustration of the system 10, to FIG. 1F, which shows a detailed view of exposed needle tip 125 of the system 10, and to FIG. 1G, which is a sectional illustration of the system 10, taken along section lines 1G-1G in FIG. 1E.

As seen, luer lock 122 of hypodermic needle 120 connects to luer lock 106 of syringe 100, such that the interior of barrel 102 of syringe 100 is in fluid flow communication with needle 124.

In some embodiments, in which syringe 100 already includes a fluid or medicament therein, plunger 110 is initially rearwardly extended, as shown in FIGS. 1A, 1D, 1E, and 1G. However, it will be appreciated that in cases in which syringe 100 is provided empty, plunger 110 would initially be disposed mostly within barrel 102, and would be drawn rearwardly by the user when drawing liquid into the syringe. This may be achieved, for example, by use of a removable vial adaptor which may be attached, or could be pre-attached, over the forward end of system 10.

In some embodiments, the syringe 100 may be a standard glass or plastic syringe with a staked in needle, and with a needle sheath (soft or rigid) that seals the needle for storage of a prefilled medicine. The needle sheath must be removed by the user prior to use (e.g., using a specific cap/remover). Example of such prefilled syringe are BD Hypak™ glass prefillable syringes with or without fixed needles (http://www.bd.com/pharmaceuticals/products/BDHypakProductRange.asp)

Guiding and locking ring 220 is disposed within internal sleeve 240, such that guiding pins 222 are disposed within slots 242. The interface between guiding pins 222 and slots 242 transitions system 10 between operative orientations, as explained in further detail hereinbelow. Additionally, this connection maintains the internal sleeve 240 in place and restrains its forward movement relative to locking ring 222 during storage. Guiding and locking ring 220 may be fixed to, integrated as part of, or rotatable relative to needle hub 126 and/or to barrel 102 of syringe 100.

Spring 230 is disposed around needle 124 within internal sleeve 240. The spring 230 engages, at a rearward facing end thereof, needle hub 126, and at a forward end thereof the spring 230 engages an interior surface of rim 258 of internal sleeve 240, such that compression and torsion loads of spring 230 are applied to internal sleeve 240, as explained in further detail hereinbelow. Alternately, spring 230 may engage, at the rearward facing end thereof, the luer lock 106 of syringe 100 or any other forward facing part of syringe 100.

Internal sleeve 240 is disposed within external shield 260, such that an external surface of rim 258 of internal sleeve 240 lies against an internal side of skin engaging surface 262 of external shield 260, such that needle tip 125 of needle 124 extends through opening 266 and projects slightly forward of skin engaging surface 262, as seen clearly in FIG. 1F. A rearward portion of external shield 260 is slidably disposed within a forward portion of outer sleeve 210, and a rearward end of outer sleeve 210 is fixedly attached to flange 104 of syringe 100.

In some embodiments, outer sleeve 210 may be integrally formed with flange 104, or may be pre-attached thereto. In some such embodiments, hypodermic needle 120 may be integrally formed with syringe 100, or may be connected to the syringe by the manufacturer.

In other embodiments, outer sleeve 210, together with the remainder of needle protection assembly 200, may be a standalone device, and may be connected to flange 104 of syringe 100 by the user, prior to use. The connection between the needle protection assembly 200 and the syringe 100 may be by any suitable means, such as using a snap fit connection, a fastener, adhesive, solvent, welding, or any other attachment form known to those skilled in the art. In some such embodiments, hypodermic needle 120 may form part of needle protection assembly 200, and luer lock 122 of needle 120 may be connected to luer lock 106 of syringe 100 by the user, at the time of connecting assembly 200 to syringe 100. However, the attachment between the needle 120 and syringe 100 may be using any suitable means known in the art, such as a snap fit connection, or may be by means of a fastener, adhesive, solvent, welding, threading, or any other attachment form known to those skilled in the art.

It will be appreciated by people of skill in the art that though in the illustrated embodiment, guiding and locking ring 220 is fixed to needle hub 126, and, as explained in detail hereinbelow, during operation of system 10 the transition between operative orientations is achieved by axial and rotational motion of internal sleeve 240, system 10 may be designed such that guiding and locking ring 220 is rotatable relative to hypodermic needle 120, such that transition between operative orientations of system 10 is achieved by rotation of ring 220 and axial movement of internal sleeve 240, without requiring rotational movement of internal sleeve 240.

Reference is now made to FIG. 2A, which is a planar side view illustration of system 10, in a storage operative orientation, to FIG. 2B, which is a perspective view illustration of system 10 of FIG. 2A, having outer sleeve 210 and external shield 260 removed therefrom, to FIG. 2C, which shows a detailed view of a portion of system 10 in the storage operative orientation, and to FIG. 2D, which is a sectional illustration of system 10 of FIG. 2A, taken along section lines 2D-2D in FIG. 2A.

In the storage operative orientation, spring 230 is partially compressed, and may apply torque to internal sleeve 240. In some embodiments, in which syringe 100 already has a fluid included in the barrel 102, plunger 110 is drawn rearwardly relative to barrel 102, as illustrated. However, it will be appreciated that in other embodiments, in which no fluid is provided within syringe 100, the plunger may be mostly disposed within barrel 100.

As seen in particular clarity in FIG. 2C, in the storage operative orientation, guiding pin 222 of guiding and locking ring 220 lie against storage surface 244 of slot 242 of internal sleeve 240.

As seen in FIGS. 2A, 2B, and 2D, needle tip 125 protrudes outwardly from external shield 260, via opening 266 thereof. It will be appreciated that the exact location of storage surface 244 of slot 242 determines the extent to which needle tip 125 protrudes from external shield 260. Specifically, when storage surface 244 is located closer to the rearward end of shield 240, the needle tip 125 protrudes to a lesser extent from external shield 260, and may, in some embodiments not illustrated herein, not protrude at all from the external shield 260 in the storage operative orientation. Conversely, when storage surface 244 is located closer to the forward end of shield 240, the needle tip 125 protrudes to a greater extent from external shield 260. It will be appreciated that the fact that needle tip 125 protrudes from external shield 260 is advantageous as it allows a user to better direct the needle to the injection site, as well as to aspirate the needle and syringe, remove some of the medicament from the syringe, remove air-bubbles from the syringe, add medicament to the syringe, or otherwise manipulate the liquid in the syringe by manipulating plunger 110 via flange 115 thereof, without activating the protection mechanism of assembly 200.

Reference is now made to FIG. 3A, which is a planar side view illustration of the system 10, in a triggering operative orientation, to FIG. 3B, which is a perspective view illustration of the system 10 of FIG. 3A, having outer sleeve 210 and external shield 260 removed therefrom, to FIG. 3C, which shows a detailed view of a portion of system 10 in the triggering operative orientation, and to FIG. 3D, which is a sectional illustration of the system 10 of FIG. 3A, taken along section lines 3D-3D in FIG. 3A.

In the triggering operative orientation, which occurs when the user begins pressing external shield 260 against the injection site, external shield 260 and internal sleeve 240 are guided rearwardly, against the compression force of spring 230, thereby exposing a greater portion of needle 124. Due to the rearward motion of internal sleeve 240, guiding pin 222 of guiding and locking ring 220 moves along slot 242 of internal sleeve 240 from storage surface 244 to triggering surface 246, as seen clearly in FIG. 3C. Once the pin 222 reaches triggering surface 246, is slides along triggering surface 246 until reaching torque limiting surface 250 under the torsion force applied by spring 230 to internal sleeve 240, thereby causing rotation of internal sleeve 240.

By sliding along triggering surface 246 of internal sleeve 240, needle protection assembly 200 reaches a safety feature triggering point. At this triggering point, if the user continues to press external shield 260 against the injection site, the safety feature is irreversibly activated, and once the external shield is removed from the injection site the needle will become blocked by external shield 260, as explained in further detail hereinbelow. On the other hand, if prior to reaching the triggering point the user removes pressure from the external shield 260, for example by removing it from the injection site, the needle protection assembly 200 returns to its storage position shown in FIGS. 2A-2D, due to the release of spring 230 which causes internal sleeve 240 to move forwardly, resulting in guiding pin 222 of guiding and locking ring 220 returning to lie against storage surface 244 of slot 242.

It will be appreciated that the exact location of triggering surface 246 of slot 242 determines the extent to which external shield 260 may be pressed prior to activation of the safety feature of system 10. Specifically, when triggering surface 246 is located closer to the storage surface 244 of slot 242, the safety feature is triggered by application of less pressure to external shield 260, or the system is more sensitive to pressure, and when triggering surface 246 is located farther from storage surface 244 of slot 242, the safety feature is triggered by application of more pressure to external shield 260, or the system is more sensitive to pressure.

Reference is now made to FIG. 4A, which is a planar side view illustration of the system 10, in an injection operative orientation, to FIG. 4B, which is a perspective view illustration of the system 10 of FIG. 4A, having outer sleeve 210 and external shield 260 removed therefrom, to FIG. 4C, which shows a detailed view of a portion of system 10 in the injection operative orientation, and to FIG. 4D, which is a sectional illustration of the system 10 of FIG. 4A, taken along section lines 4D-4D in FIG. 4A.

In the injection operative orientation, which occurs when the user continues pressing external shield 260 against the injection site, typically to the full extent possible, external shield 260 and internal sleeve 240 are guided rearwardly, against the compression force of spring 230. Due to the rearward motion of internal sleeve 240, guiding pin 222 of guiding and locking ring 220 moves along torque limiting surface 250 of slot 242 of internal sleeve 240 from the height of triggering surface 246 to the corner between end of press surface 248 and torque limiting surface 250, as seen clearly in FIG. 4C. When guiding pin 222 engages the end of press surface 248, the needle 124, and particularly needle tip 125, is at its full penetration depth.

It will be appreciated that the exact location of end of press surface 248 of slot 242 determines the extent to which needle 124, and particularly needle tip 125, penetrates the injection site. Specifically, end of press surface 248 being located closer to the rearward end of shield 240 results in a smaller needle penetration depth, whereas end of press surface 248 being located closer to the forward end of shield 240 results in a greater needle penetration depth.

Following needle penetration, the user presses the plunger flange 115 of plunger 110 to inject the fluid contained in syringe barrel 102. Typically, the user presses plunger flange 115 until a hard stop is reached, which is indicative of the end of injection, meaning that all fluid contained in barrel 102 of syringe 100 was injected.

It will be appreciated that one of the advantages system 10 is that, regardless whether the user has fully pressed syringe plunger 110 to inject the full fluid dose, or whether the user injected only partial amount of the fluid, the safety mechanism is activated once the triggering surface has been reached, or passed, by guiding pins 222.

Figures 5A, 5B, 5C, 5D:
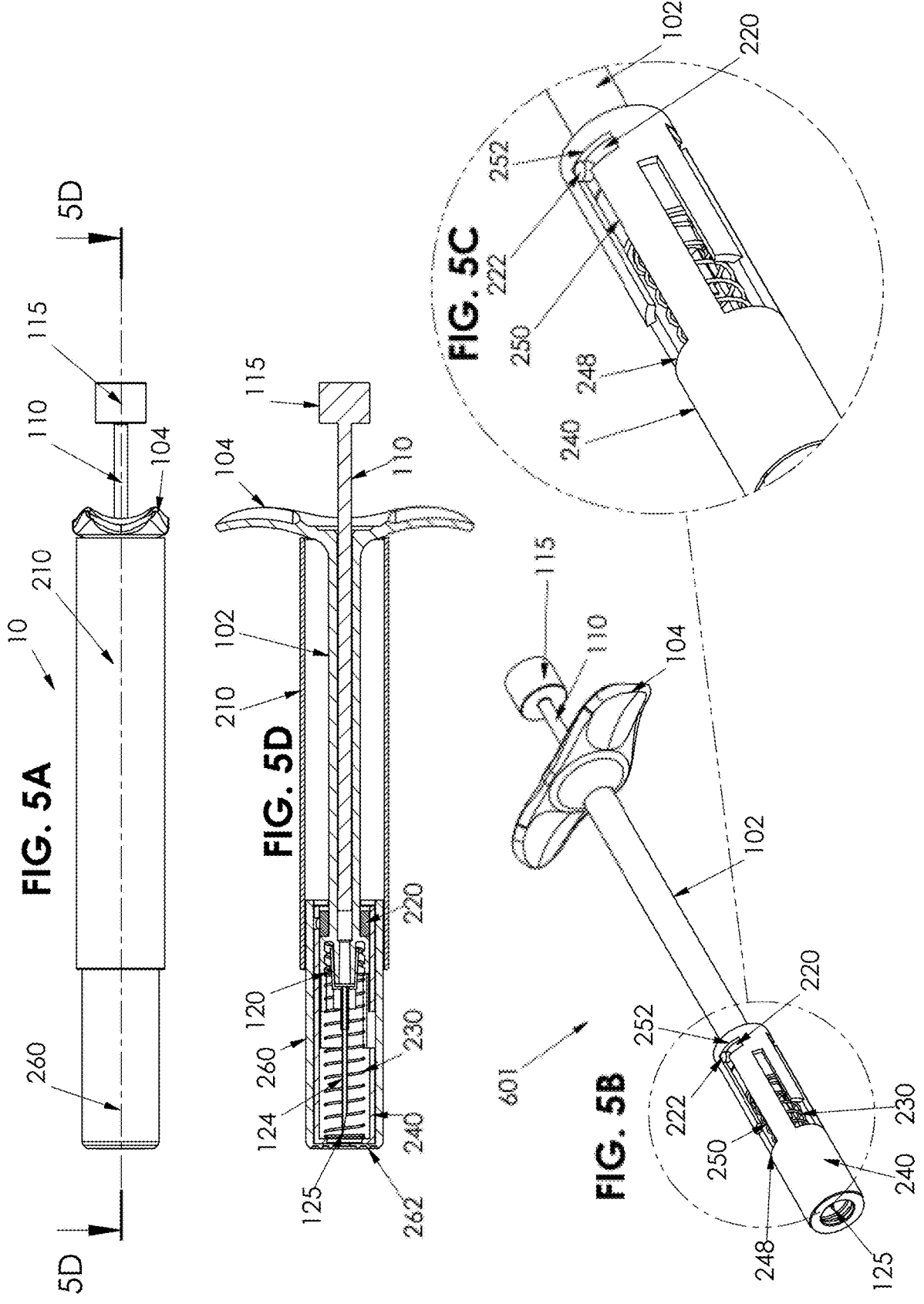
FIG. 5A is a planar side view illustration of the system of FIGS. 1A to 1G, in a pre-locking operative orientation.
FIG. 5B is a perspective view illustration of the system of FIG. 5A, having the outer sleeve and external shield removed therefrom.
FIG. 5C shows a detailed view of a portion of the system of FIG. 5B.
FIG. 5D is a sectional illustration of the system of FIG. 5A, taken along section lines 5D-5D in FIG. 5A.

Reference is now made to FIG. 5A, which is a planar side view illustration of the system 10, in a pre-locking operative orientation, to FIG. 5B, which is a perspective view illustration of the system 10 of FIG. 5A, having outer sleeve 210 and external shield 260 removed therefrom, to FIG. 5C, which shows a detailed view of a portion of system 10 in the pre-locking operative orientation, and to FIG. 5D, which is a sectional illustration of the system 10 of FIG. 5A, taken along section lines 5D-5D in FIG. 5A.

The pre-locking operative orientation occurs following injection, or following triggering of the safety feature of assembly 200, when the user releases the pressure from external shield 260, for example by removing system 10 from the injection site, and just before the internal sleeve 240 locks around needle 120. As seen clearly in FIG. 5C, following removal of pressure from external shield 260, pressure is removed from spring 230, which decompresses and drives internal sleeve 240 forwardly, together with external shield 260. Forward motion of internal sleeve 240 results in relative rearward motion of guiding pin 222 of guiding and locking ring 220 along torque limiting surface 250 slot 242 of internal sleeve 240 to protection surface 252. When guiding pin 222 engages the protection surface 252, the needle 124, and particularly needle tip 125, is disposed within external shield 260.

It will be appreciated that the exact location of protection surface 252 of slot 242 determines the protection depth of needle 124, and particularly needle tip 125, or the extent to which external shield 260 extends beyond needle tip 125. Specifically, protection surface 252 being located closer to the rearward end of shield 240 results in a greater needle protection depth, whereas protection surface 252 being located closer to the forward end of shield 240 results in a smaller needle protection depth.

Figures 6A, 6B, 6C, 6D:
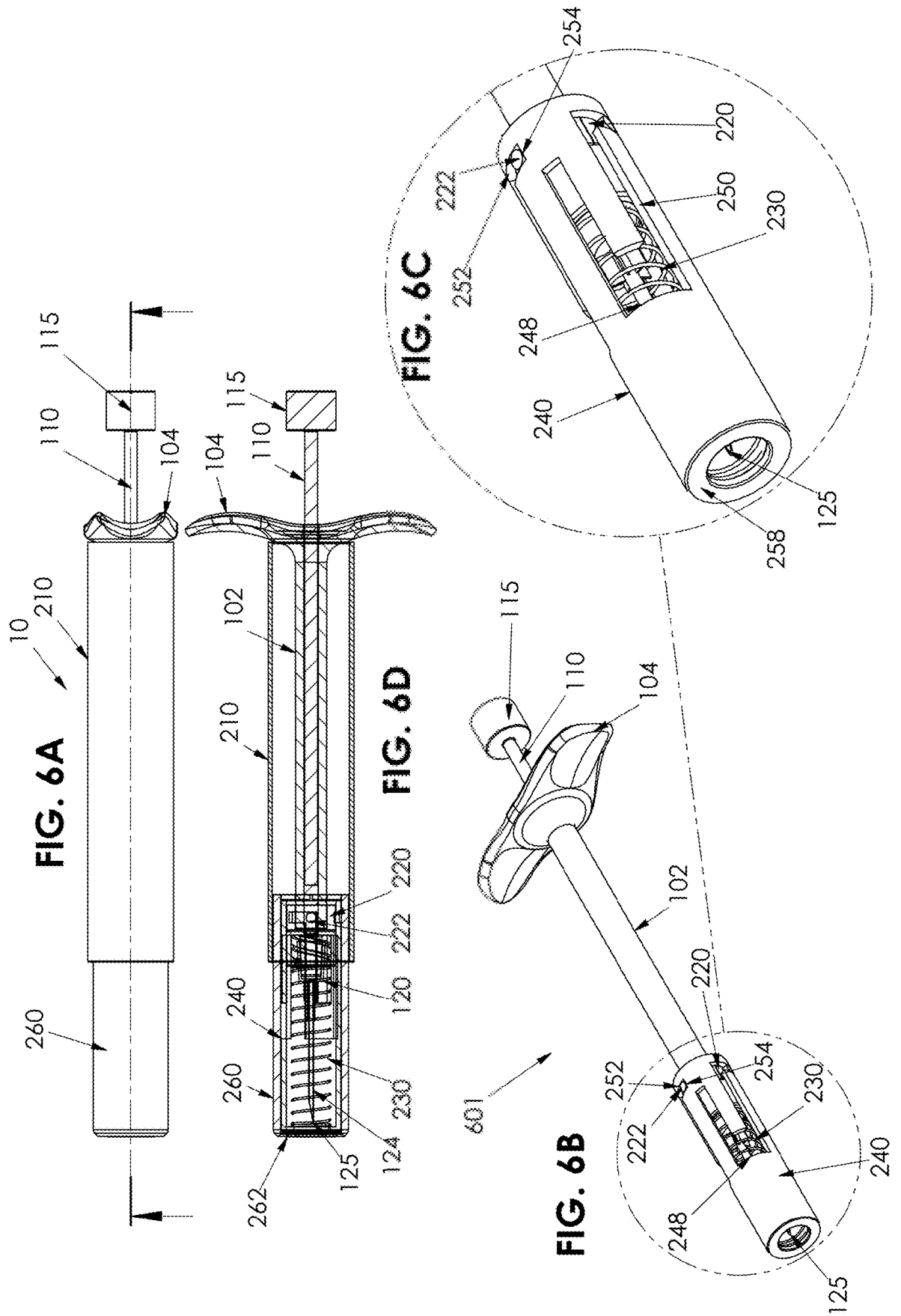
FIG. 6A is a planar side view illustration of the system of FIGS. 1A to 1G, in a locked operative orientation.
FIG. 6B is a perspective view illustration of the system of FIG. 6A, having the outer sleeve and external shield removed therefrom.
FIG. 6C shows a detailed view of a portion of the system of FIG. 6B.
FIG. 6D is a sectional illustration of the system of FIG. 6A, taken along section lines 6D-6D in FIG. 6A.

Reference is now made to FIG. 6A, which is a planar side view illustration of the system 10, in a locked operative orientation, to FIG. 6B, which is a perspective view illustration of the system 10 of FIG. 6A, having outer sleeve 210 and external shield 260 removed therefrom, to FIG. 6C, which shows a detailed view of a portion of system 10 in the locked operative orientation, and to FIG. 6D, which is a sectional illustration of the system 10 of FIG. 6A, taken along section lines 6D-6D in FIG. 6A.

The locked operative orientation occurs automatically immediately following the pre-locking operative orientation, without requiring any additional action by the user. As seen clearly in FIG. 6C, internal sleeve 240 rotates under the torsion force of spring 230, such that guiding pin 222 of guiding and locking ring 220 slides along protection surface 252 to locking surface 254 of slot 242. The location of locking surface 254 determines the locking point of system 10 and of needle protection assembly 200.

It will be appreciated that the width of locking surface 254 determines the "give", or maneuverability, of the external shield 260 when assembly 200 is in the locked operative orientation. Specifically, a wider locking surface 254 would allow more movement of external shield 260 in the locked operative orientation, whereas a narrower locking surface 254 would allow less, or no, movement of external shield 260 in the locked operative orientation.

Reference is now made to FIG. 7A, which is an exploded view illustration of a system 300 for protection of a needle connected to a syringe according to a second embodiment of the teachings herein, the system including a safety needle device and a syringe.

As seen in FIG. 7A, the system 300 includes a syringe 301, which may include a hollow barrel 302 terminating at a rearward end thereof in a flange 304, and at a forward end thereof in a luer lock 306, which is typically a male luer lock, and which is adapted to connect to a needle as described herein. A plunger 310 terminating at a plunger flange 315 is adapted to be disposed within barrel 302, and to be movable therein, as known in the art.

A hypodermic needle 320, which may be any needle known in the art, includes a luer lock 322, which is typically a female luer lock. A needle 324, terminating in a sharp needle tip 325, is in fluid communication with luer lock 322 via a needle hub 326.

A needle protection assembly 400 includes a generally tubular outer sleeve 410, a guiding and locking tube 420, a compression spring 438, and a shield 440. While spring 438 is illustrated and described herein as a compression spring, the system may be designed to use any other suitable biasing element, such as a tension spring, a constant-force spring, an integrally formed plastic spring, or any other resilient element such as a rubber, plastic or elastomeric element.

Reference is now additionally made to FIG. 7B, which is a side view planar illustration of an outer sleeve 410, and to FIG. 7C, which is a sectional illustration of the outer sleeve 410, taken along section lines 7C-7C in FIG. 7B. In some embodiments, outer sleeve 410 is generally tubular and includes, at a forward facing end thereof, a plurality of protrusions 412, which may be rectangular or may have any other suitable shape, and may be used to assist in orientation of the outer sleeve during assembly of system 300. On an inner surface thereof, outer sleeve 410 includes longitudinal ribs 413, adapted to engage shield 440 as described in further detail hereinbelow.

As seen clearly in FIG. 7D, which shows a planar side view illustration of guiding and locking tube 420 forming part of needle protection assembly 400 of system 300, the guiding and locking tube is typically hollow, and may be formed of two or more separate portions which join together to form the hollow tube, as shown in FIG. 7A. Guiding and locking tube 420, or each portion thereof includes, in a rearward portion thereof, a throughgoing slot 422. As explained in further detail hereinbelow, slot 422 includes multiple surfaces which define the stages of operation of needle protection assembly 400, the maximal needle penetration depth, and the protection depth. Specifically, slot 422 includes a storage surface 424, a first sloped surface 425, a triggering point 426, a transition surface 427, an end of press surface 428, a second sloped surface 430, a protection surface 432, and a locking surface 434. A first counter surface 421, terminating at a first corner 429, is disposed opposite first sloped surface 425, and together first counter surface 421, corner 429, and first sloped surface 425 define a triggering passage. A second counter surface 435, terminating at a second corner 433, is disposed opposite second sloped surface 430, and together second counter surface 435, corner 433, and second sloped surface 430 define a locking passage. Guiding and locking tube 420 terminates at a forward end thereof in a forward surface 436.

Turning to FIG. 7E, which shows a detailed view of shield 440 forming part of assembly 400 of system 300, the shield 440 is generally tubular, and includes, in a rearward portion thereof, an exterior rim 442 including one or more slots 444 adapted to engage longitudinal ribs 413 of outer sleeve 410, as described in further detail hereinbelow. Shield 440 further includes, slightly forwardly to rim 442, an interiorly protruding guiding pin 446, and may, in some embodiments, further include an axially extending window 447 extending forwardly of pin 446 to approximately half the length of shield 440. At a forward end thereof, shield 440 terminates in a skin engaging rim 448 having an opening 456 at the center thereof.

The construction of system 300 will now be explained making additional reference to FIG. 7F, which is a perspective view of the system 300, when constructed, to FIG. 7G, which is a side view planar illustration of the system 300, when constructed, and to FIG. 7H, which is a sectional illustration of the system 300, taken along section lines 7H-7H in FIG. 7G.

As seen, luer lock 322 of hypodermic needle 320 connects to luer lock 306 of syringe 301, such that the interior of barrel 302 of syringe 301 is in fluid flow communication with needle 324.

In some embodiments, in which syringe 301 already includes a fluid or medicament therein, plunger 310 is initially rearwardly extended, as shown in FIGS. 7A, 7F, 7G, and 7H. However, it will be appreciated that in cases in which syringe 301 is provided empty, plunger 310 would initially be disposed mostly within barrel 302, and would be drawn rearwardly by the user when drawing liquid into the syringe. This may be achieved, for example, by use of a removable vial adaptor which may be attached, or could be pre-attached, over the forward end of system 10.

In some embodiments, the syringe 100 may be a standard glass or plastic syringe with a staked in needle, and with a needle sheath (soft or rigid) that seals the needle for storage of a prefilled medicine. The needle sheath must be removed by the user prior to use (e.g., using a specific cap/remover). Example of such prefilled syringe are BD Hypak™ glass prefillable syringes with or without fixed needles (http://www.bd.com/pharmaceuticals/products/BDHypakProductRange.asp)

Guiding and locking tube 420 is disposed about barrel 302 of syringe 301 and within shield 440, such that guiding pins 446 are disposed within slots 422. The interface between guiding pins 446 and slots 422 transitions system 300 between operative orientations, as explained in further detail hereinbelow. Additionally, this connection maintains the shield 440 in place and restrains its forward movement relative to guiding and locking tube 420 during storage. Guiding and locking tube 420 may be fixed to, integrated as part of, or rotatable relative to needle hub 326 and/or to barrel 302 of syringe 301.

Spring 438 is disposed around needle 324 within shield 440. The spring 438 engages, at a rearward facing end thereof, luer lock 306, and at a forward end thereof the spring 438 engages an interior surface of rim 448 of shield 440, such that compression, and when relevant also torsion, loads of spring 438 are applied to shield 440, as explained in further detail hereinbelow. Alternatively, spring 438 may engage, at a rearward facing end thereof, forward end 436 of guiding and locking tube 420, such that compression loads of spring 438 are applied to guiding and locking tube 420.

Figure 7G:
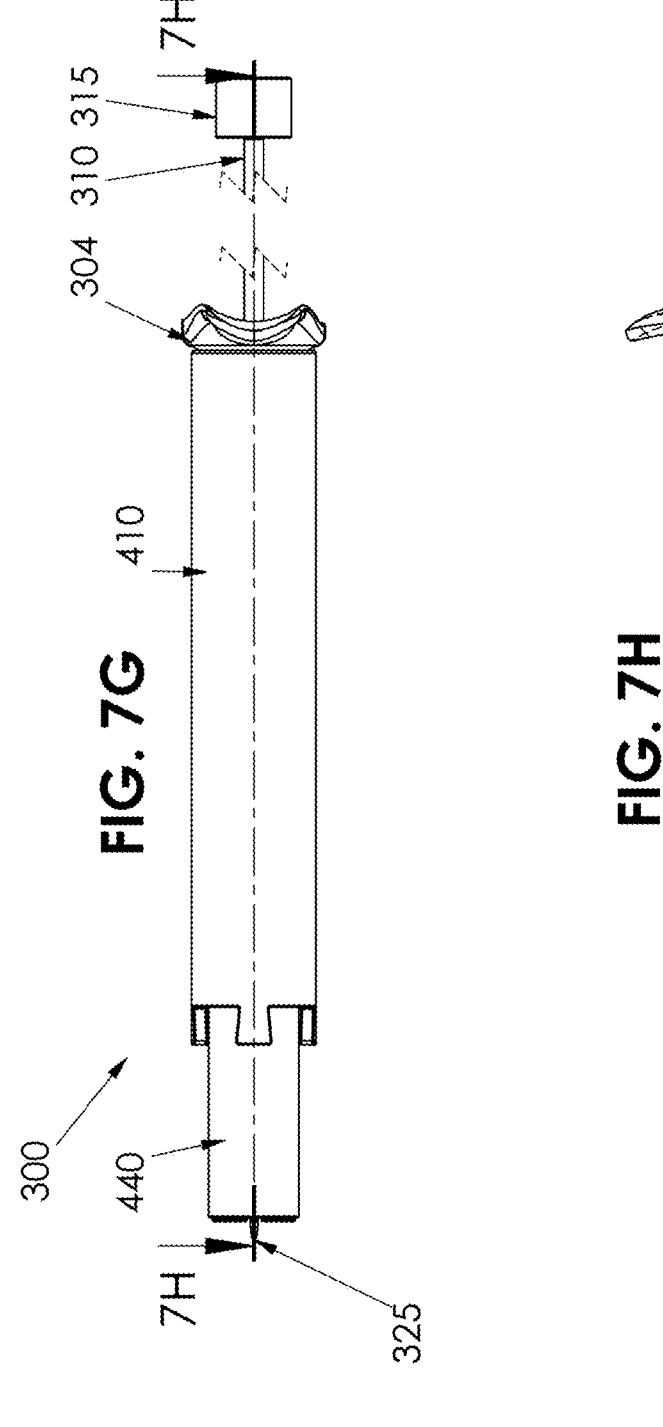
FIG. 7G is a side view planar illustration of the system of FIG. 7A, when constructed.
Figure 7H:
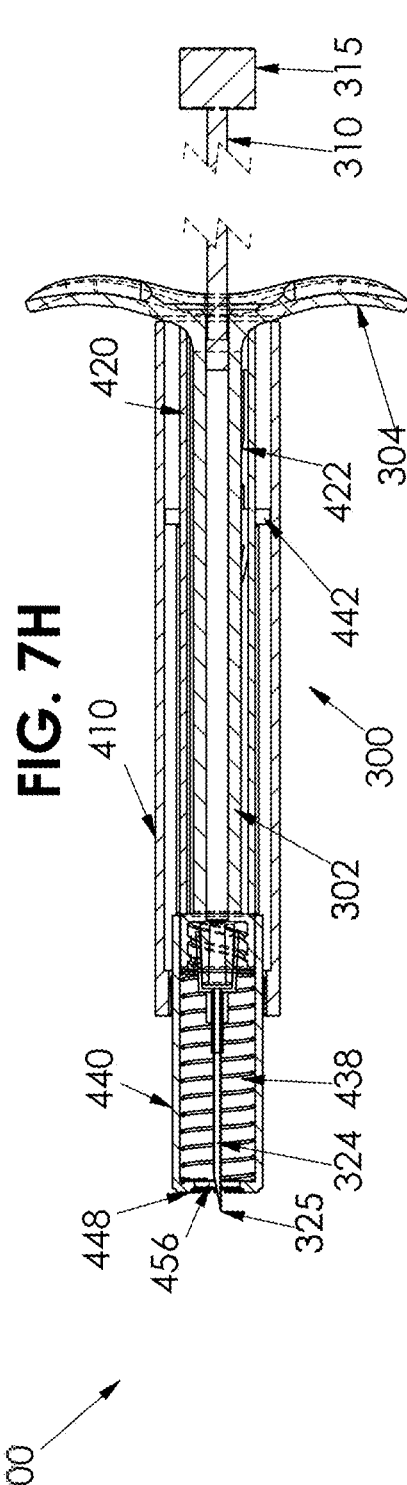
FIG. 7H is a sectional illustration of the system of FIG. 7G, taken along section lines 7H-7H in FIG. 7G.

Needle tip 325 of needle 324 extends through opening 456 of shield 440, and projects slightly forward of skin engaging rim 448, as seen clearly in FIGS. 7G and 7H. Shield 440 and guiding and locking tube 420 are slidably disposed within outer sleeve 410, such that longitudinal ribs 413 of outer sleeve 410 are disposed in slots 444 of shield 440 and prevent relative rotation of between shield 440 and outer sleeve 410. A rearward end of outer sleeve 410 is fixedly attached to flange 304 of syringe 301.

In some embodiments, outer sleeve 410 may be integrally formed with flange 304, or may be pre-attached thereto. In some such embodiments, hypodermic needle 320 may be integrally formed with syringe 301, or may be connected to the syringe by the manufacturer.

In other embodiments, outer sleeve 410, together with the remainder of needle protection assembly 400, may be a standalone device, and may be connected to flange 304 of syringe 301 by the user, prior to use. The connection between the needle protection assembly 400 and the syringe 301 may be by any suitable means, such as using a snap fit connection, a fastener, adhesive, solvent, welding, or any other attachment form known to those skilled in the art. In some such embodiments, hypodermic needle 320 may form part of needle protection assembly 400, and luer lock 322 of needle 320 may be connected to luer lock 306 of syringe 301 by the user, at the time of connecting assembly 400 to syringe 301. However, the attachment between the needle 320 and syringe 301 may be using any suitable means known in the art, such as a snap fit connection, or may be by means of a fastener, adhesive, solvent, welding, or any other attachment form known to those skilled in the art.

Reference is now made to FIG. 8A, which is a perspective view illustration of system 300, having outer sleeve 410 removed therefrom, in a storage operative orientation, to FIG. 8B, which is an oriented model view illustration of the system 300 in the storage operative orientation, and to FIG. 8C, which is a detailed view of a portion of system 300 in the storage operative orientation.

In the storage operative orientation, spring 438 is partially compressed, and may, in some embodiments, apply torque to shield 440 and/or to guiding and locking tube 420. In some embodiments, in which syringe 301 already has a fluid included in the barrel 302, plunger 310 is drawn rearwardly relative to barrel 302, as illustrated. However, it will be appreciated that in other embodiments, in which no fluid is provided within syringe 301, the plunger may be mostly disposed within barrel 302.

As seen in particular clarity in FIG. 8C, in the storage operative orientation, guiding pin 446 of shield 440 lie against storage surface 424 of slot 422 of guiding and locking tube 420.

As seen in FIGS. 8A and 8B, needle tip 325 protrudes outwardly from shield 440, via opening 456 thereof. It will be appreciated that the exact location of storage surface 424 of slot 422 determines the extent to which needle tip 325 protrudes from shield 440. Specifically, when storage surface 424 is located closer to the rearward end of guiding and locking tube 420, the needle tip 325 protrudes to a greater extent from shield 440, and when storage surface 424 is located closer to the forward end of guiding and locking tube 420, the needle tip 325 protrudes to a lesser extent from shield 440, and may, in some embodiments not illustrated herein, not protrude at all from the external shield 260 in the storage operative orientation.

It will be appreciated that the fact that needle tip 325 protrudes from shield 440 is advantageous as it allows a user to better direct the needle to the injection site, as well as to aspirate the needle and syringe, remove some of the medicament from the syringe, remove air-bubbles from the syringe, add medicament to the syringe, or otherwise manipulate the liquid in the syringe by manipulating plunger 310 via flange 315 thereof, without activating the protection mechanism of assembly 400.

Figures 9A, 9B, 9C:
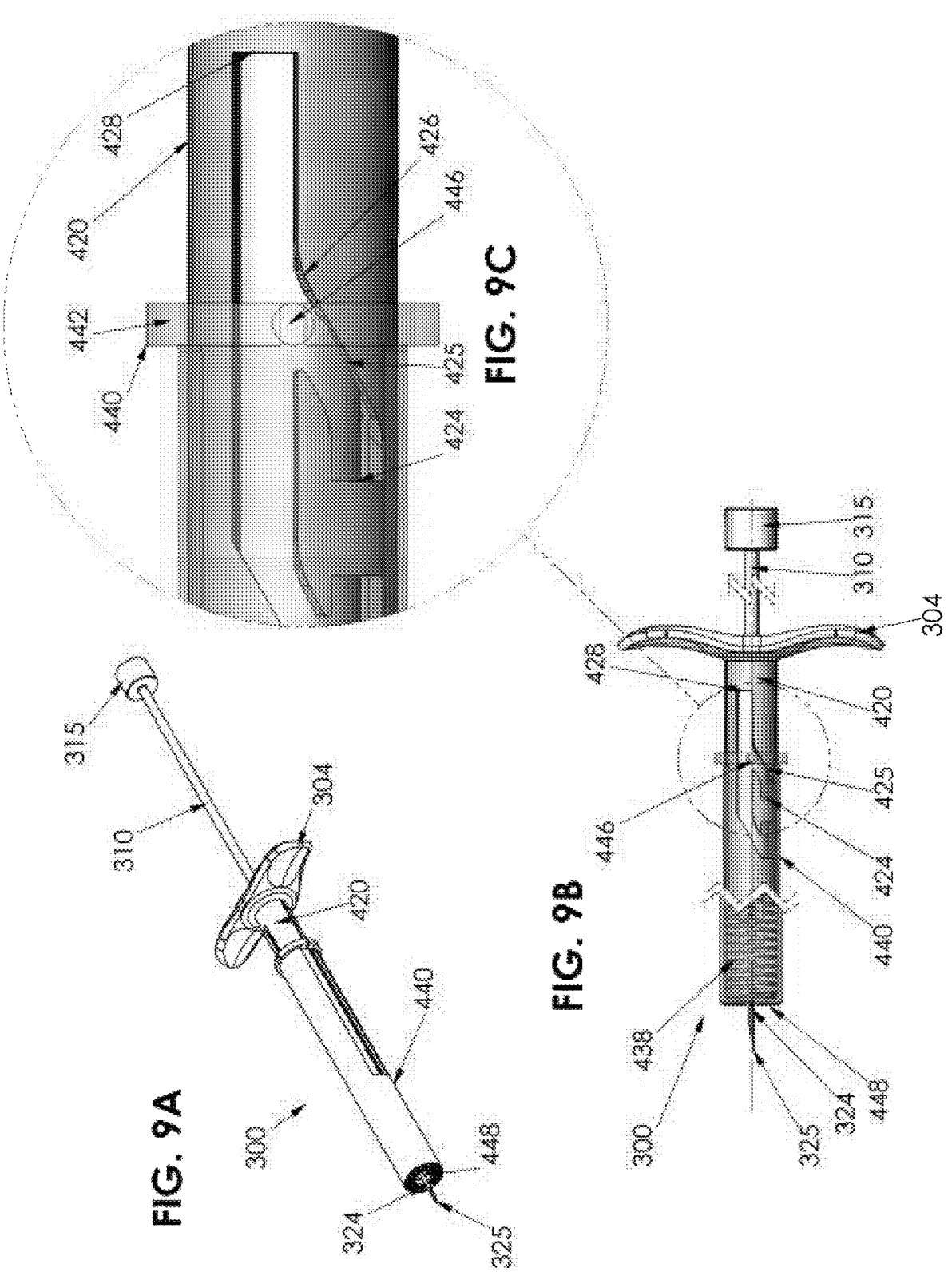
FIG. 9A is a perspective view illustration of the system of FIGS. 7A and 7B, having the outer sleeve removed therefrom, in a triggering operative orientation.
FIG. 9B is a model view illustration of the system of FIG. 9A.
FIG. 9C is a detailed view of a portion of the system of FIG. 9B.

Reference is now made to FIG. 9A, which is a perspective view illustration of system 300, having outer sleeve 410 removed therefrom, in a triggering operative orientation, to FIG. 9B, which is an oriented model view illustration of the system 300 in the triggering operative orientation, and to FIG. 9C, which is a detailed view of a portion of system 300 in the triggering operative orientation.

In the triggering operative orientation, which occurs when the user begins pressing shield 440 against the injection site, shield 440 is guided rearwardly, against the compression force of spring 438, thereby exposing a greater portion of needle 324. Due to the rearward motion of shield 440, guiding pin 446 thereof moves along slot 422 of guiding and locking tube 420 from storage surface 424, along first slope 425, to triggering point 426, via the triggering passage, as seen clearly in FIG. 9C. Since shield 440 cannot rotate relative to outer sleeve 410, due to engagement between longitudinal ribs 413 of outer sleeve 410 and slots 444 of shield 440, motion of guiding pin 446 along slope 425 causes rotation of tube 420 relative to shield 440 and to needle 324.

When guiding pin 446 of shield 440 reaches triggering point 426, the safety feature of needle protection assembly 400 may be triggered. At this triggering point the safety feature is irreversibly activated, and once the shield is removed from the injection site the needle will become blocked by shield 440, as explained in further detail hereinbelow. On the other hand, if prior to reaching the triggering point the user removes pressure from the shield 440, for example by removing it from the injection site, the needle protection assembly 400 returns to its storage position shown in FIGS. 8A-8C, due to the release of spring 438 which causes shield 440 to move forwardly, guiding pin 446 of shield 440 causes rotation of locking tube 420 back to its storage position, resulting in guiding pin 446 of shield 440 returning to lie against storage surface 424 of slot 422 of guiding and locking tube 420.

In some embodiments, the safety feature is activated by the triggering passage between surfaces 421 and 425 allowing passage of pin 446 only in one direction. For example, corner 429 may include, or end in, a flexible resilient finger (not shown) allowing passage of pin 446 out of the triggering passage but not back into the triggering passage, thus making sure that the pin 446 would not go back to the storage operative orientation once the triggering point 426 has been passed. In other embodiments, a similar one-way passage may be achieved by having the width of the triggering passage between surfaces 421 and 425 be smaller than the width or diameter of pin 446, which would cause the pin to apply pressure in order to move past the triggering point 426. As another embodiment, a one-way passage may be formed creating a detent in the triggering passage. It will be appreciated that the exact location of triggering point 426 of slot 422 determines the extent to which shield 440 may be pressed prior to activation of the safety feature of system 300. Specifically, when triggering point 426 is located closer to the forward end of guiding and locking tube 420, the safety feature is triggered by application of less pressure to shield 400, or the system is more sensitive to pressure, and when triggering point 426 is located closer to the rearward end of guiding and locking tube 420, the safety feature is triggered by application of more pressure to shield 440.

Figures 10A, 10B, 10C:
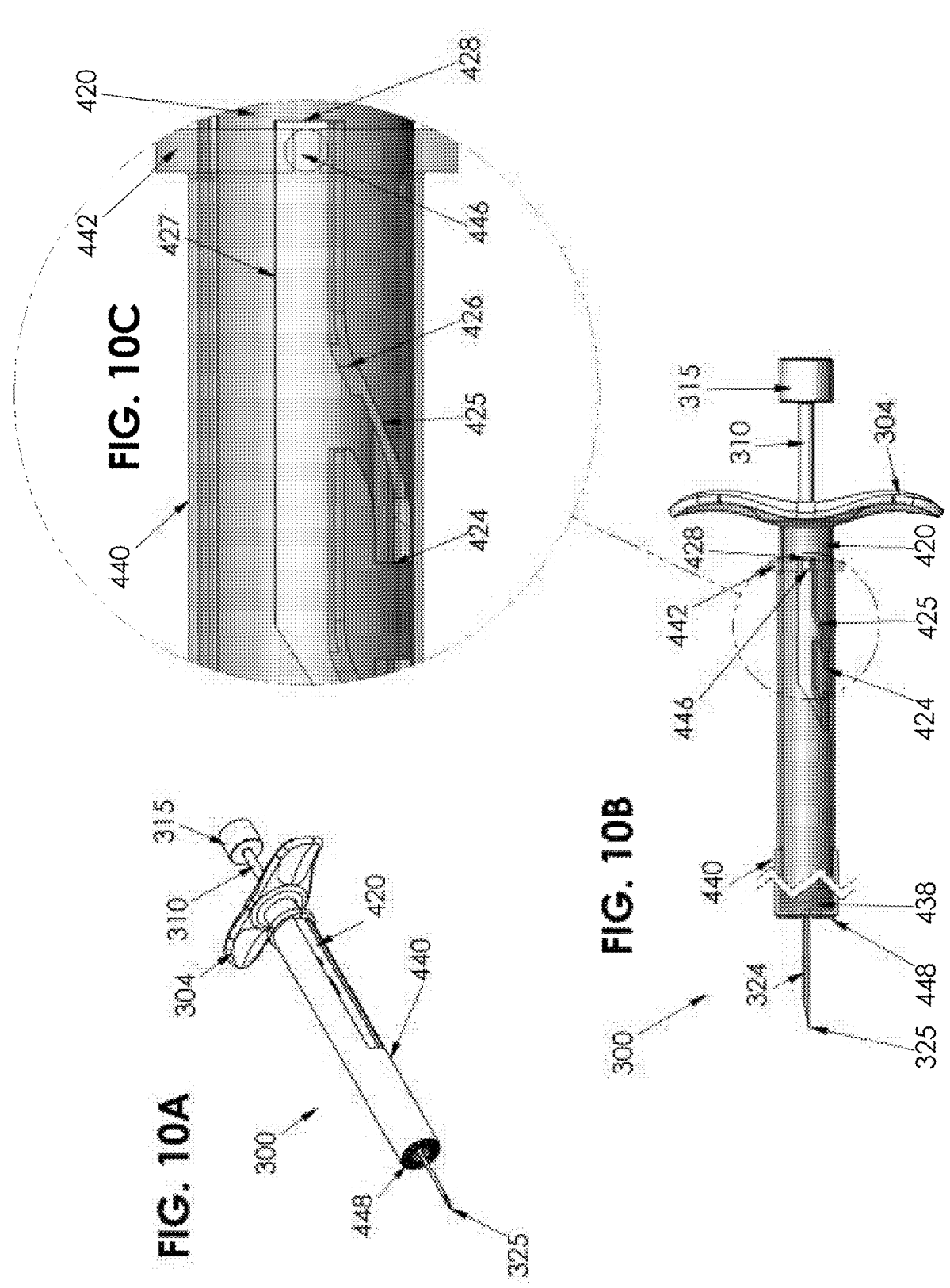
FIG. 10A is a perspective view illustration of the system of FIGS. 7A and 7B, having the outer sleeve removed therefrom, in an injection operative orientation.
FIG. 10B is a model view illustration of the system of FIG. 10A.
FIG. 10C is a detailed view of a portion of the system of FIG. 10B.

Reference is now made to FIG. 10A, which is a perspective view illustration of system 300, having outer sleeve 410 removed therefrom, in an injection operative orientation, to FIG. 10B, which is an oriented model view illustration of the system 300 in the injection operative orientation, and to FIG. 10C, which is a detailed view of a portion of system 300 in the injection operative orientation.

In the injection operative orientation, which occurs when the user continues pressing shield 440 against the injection site, typically to the full extent possible, shield 440 is guided rearwardly, against the compression force of spring 438. Due to the rearward motion of shield 440, guiding pin 446 thereof moves along transition surface 427 of slot 422 of guiding and locking tube 420 between triggering point 426 and end of press surface 428, as seen clearly in FIG. 10C. When guiding pin 446 engages the end of press surface 428, the needle 324, and particularly needle tip 325, is at its full penetration depth.

It will be appreciated that the exact location of end of press surface 428 of slot 422 determines the extent to which needle 324, and particularly needle tip 325, penetrates the injection site. Specifically, end of press surface 428 being located closer to the forward end of guiding and locking tube 420 results in a smaller needle penetration depth, whereas end of press surface 428 being located closer to the rearward end of guiding and locking tube 420 results in a greater needle penetration depth.

Following needle penetration, the user presses the plunger flange 315 of plunger 310 to inject the fluid contained in syringe barrel 302. Typically, the user presses plunger flange 315 until a hard stop is reached, which is indicative of the end of injection, meaning that all fluid contained in barrel 302 of syringe 301 was injected.

It will be appreciated that one of the advantages system 300 is that, regardless whether the user has fully pressed the syringe plunger 310 to inject the full fluid dose, or whether the user injected only partial amount of the fluid, the safety mechanism is activated once the triggering surface has been reached, or passed, by guiding pins 446.

Reference is now made to FIG. 11A, which is a perspective view illustration of system 300, having outer sleeve 410 removed therefrom, in a first locked operative orientation, to FIG. 11B, which is an oriented model view illustration of the system 300 in the first locked operative orientation, to FIG. 11C, which is a detailed view of a portion of system 300 in the first locked operative orientation, and to FIG. 11D, which is a sectional illustration of the system 300 in the first locked operative orientation, the sectional illustration taken along section lines 11D-11D in FIG. 11B.

The first locked operative orientation occurs following injection, or following triggering of the safety feature of assembly 400, when the user releases the pressure from shield 440, for example by removing system 300 from the injection site, and the shield 440 extends fully forwardly, safely locking around needle 320. As seen clearly in FIG. 11B, following removal of pressure from shield 440, pressure is removed from spring 438, which decompresses and drives shield 240 forwardly. Forward motion of shield 440 results in guiding pin 446 thereof moving forwardly along transition surface 427 and along second sloped surface 430 of slot 422 of guiding and locking tube 420 to protection surface 432. It will be appreciated that motion of pin 446 along second sloped surface 430 results in rotation of guiding and locking tube 420 relative to syringe 301. When guiding pin 446 engages the protection surface 432, the needle 324, and particularly needle tip 325, is disposed within shield 440.

In some embodiments, locking is achieved by the structure of the locking passage between surfaces 430 and 435 allowing passage of pin 446 only in one direction. For example, corner 433 may include, or end in, a flexible resilient finger (not shown) allowing passage of pin 446 out of the locking passage but not back into the locking passage, thus making sure that the pin 446 would not go back to the transition surface 427. In other embodiments, a similar one-way passage may be achieved by having the width of the locking passage between surfaces 430 and 435 be smaller than the width or diameter of pin 446, which would cause the pin to apply pressure in order to move along sloped surface 430. As another embodiment, a one-way passage may be formed creating a detent in the locking passage.

It will be appreciated that the exact location of protection surface 432 of slot 422 determines the protection depth of needle 324, and particularly needle tip 325, or the extent to which shield 440 extends beyond needle tip 325. Specifically, protection surface 432 being located closer to the forward end of guiding and locking tube 420 results in a greater needle protection depth, whereas protection surface 432 being located closer to the rearward end of guiding and locking tube 420 results in a smaller needle protection depth.

Reference is now made to FIG. 12A, which is a perspective view illustration of system 300, having outer sleeve 410 removed therefrom, in a second locked operative orientation, to FIG. 12B, which is an oriented model view illustration of the system 300 in the second locked operative orientation, to FIG. 12C, which is a detailed view of a portion of system 300 in the second locked operative orientation, and to FIG. 12D, which is a sectional illustration of the system 300 in the second locked operative orientation, the sectional illustration taken along section lines 12D-12D in FIG. 12B.

The second locked operative orientation occurs when a force in a rearward direction is applied to shield 440, against the force of spring 438. As seen clearly in FIG. 12C, when shield 440 moves rearwardly against the force of spring 438, guiding pin 446 of shield 440 moves from protection surface 432 to locking surface 434 of slot 422 of guiding and locking tube 420. The location of locking surface 434 determines amount of possible rearward movement of shield 440, or the 'give' of system 300, while maintaining needle tip 325 safely covered by shield 440, as seen clearly in FIGS. 12B and 12D.

Reference is now made to FIG. 13A, which is an exploded view illustration of a system 500 for protection of a needle, the system being connectable to a syringe (not shown), according to a third embodiment of the teachings herein.

As seen in FIG. 13A, the system 500 includes a luer housing 501, which includes a hollow luer connector 502, and a base 504 including a needle receiving through-going bore 506 at the center thereof, the needle receiving through-going bore being in fluid flow communication with luer connector 502. Luer connector 502 is connectable to a syringe or to any other suitable luer connector, as described hereinbelow. Disposed on a forward facing surface of base 504 is a spring engaging protrusion 507, described in further detail hereinbelow.

A hypodermic needle 520, which may be any needle known in the art, terminating in a sharp needle tip 525, is adapted to be received in needle receiving through-going bore 506 and thus to be in fluid communication with luer connector 502.

System 500 further includes a compression spring 530, which in some embodiments is also a torsion spring, a guiding and locking ring 540, a shield 560, and an outer sleeve 580. The system may be packaged in a packaging 599. While spring 530 is illustrated and described herein as a compression spring, the system may be designed to use any other suitable biasing element, such as a tension spring, a constant-force spring, an integrally formed plastic spring, or any other resilient element such as a rubber, plastic or elastomeric element.

Figure 13E:
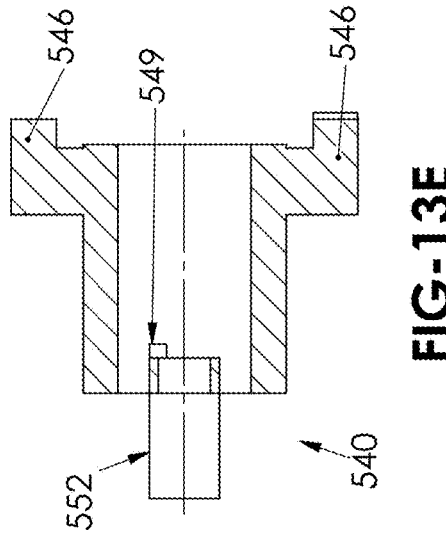
FIGS. 13D and 13E are sectional illustrations of the guiding and locking ring, the sectional illustrations taken along respective section lines 13D-13D and 13E-13E in FIG. 13C.
Figure 13C:
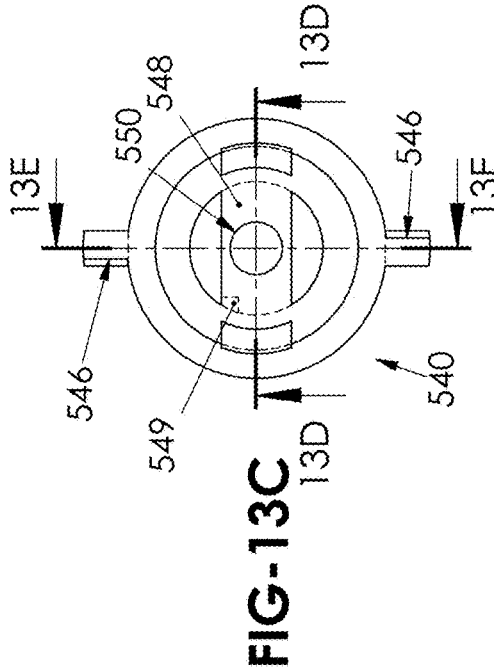
FIG. 13C is a front view planar illustration of the guiding and locking ring of FIG. 13B.
Figure 13D:
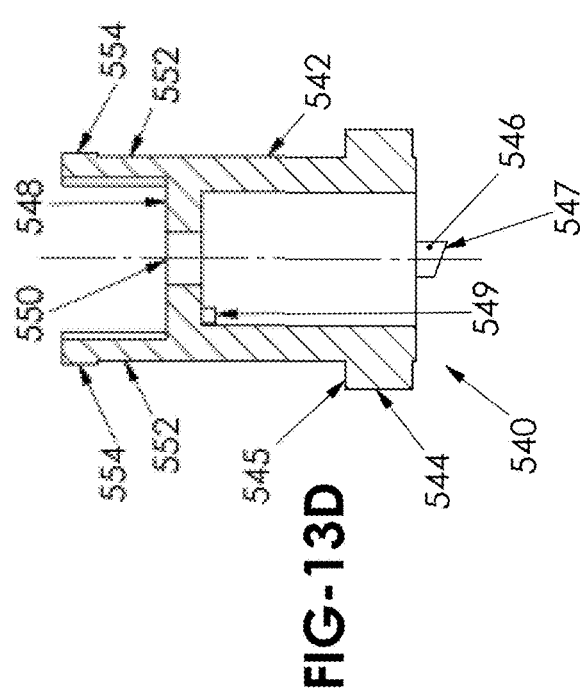

Reference is now additionally made to FIG. 13B, which shows a detailed view of guiding and locking ring 540 forming part of system 500, to FIG. 13C, which is a front view planar illustration of the guiding and locking ring 540, and to FIGS. 13D and 13E, which are sectional illustrations of the guiding and locking ring 540, the sectional illustrations taken along respective section lines 13D-13D and 13E-13E in FIG. 13C. As seen, the ring 540 includes a hollow barrel 542, terminating at a rearward end thereof in an outwardly extending flange portion 544 including a forward facing surface 545 and having two guiding protrusions 546 extending outwardly therefrom. Each of guiding protrusions 546 terminates at a rearward end thereof in an inclined surface 547, seen clearly in FIG. 13D. Disposed about a forward end of barrel 542 is a partial wall portion 548, including, on a rearward facing surface thereof, a spring engaging protrusions 549, and having a through-going needle opening 550 disposed at the center thereof. Extending forwardly from barrel 542, on either side thereof, are a pair of locking tabs 552, each terminating in a radially outwardly facing tooth 554.

Returning to FIG. 13A, and referring additionally to FIG. 13G, which is a side view planar illustration of shield 560 and to FIG. 13H, which is a sectional illustration of the shield 560, the sectional illustration being taken along section lines 13H-13H in FIG. 13G, it is seen that shield 560 is side-to-side and top-to-bottom symmetrical, and includes a cylindrical body portion 562. At a forward end thereof, body portion 562 extends toward a tapered portion 564 terminating in a skin engaging surface 566 including, at a center thereof, an opening 568. Protruding from an exterior surface of body portion 562, at a rearward end thereof, are range limiting protrusions 570 each including a forward facing surface 572. Body portion 562 and range limiting protrusions 570 terminate, at a rearward end thereof, in a rearward facing surface 574. As seen with particular clarity in FIG. 13G, disposed along an interior surface of body portion 562 is a circumferential groove 576, adapted for engagement of shield 560 to guiding and locking ring 540, as described in further detail hereinbelow.

Reference is now made to FIG. 13H, which is a front view planar illustration of outer sleeve 580 forming part of the system 500, and to FIGS. 13I and 13J, which are sectional illustrations of the outer sleeve 580, the sectional illustrations taken along respective section lines 13I-13I and 13J-13J in FIG. 13H. As seen in FIGS. 13H to 13J, sleeve 580 is generally tubular, and has formed, in a rearward portion of an interior surface thereof, guiding slots 582, one of which seen clearly in FIG. 13J. In some embodiments, slot 582 does not extend through the entire width of sleeve 580, such that the exterior surface of sleeve 580 is completely tubular. It will be appreciated that though sleeve 580 is illustrated as having a tubular shape, the sleeve may have a rectangular or any other suitable cross-section, with proper adjustments to other mating parts of system 500 and to packaging 599.

As explained in further detail hereinbelow, slot 582 includes multiple surfaces which define the stages of operation of system 500, and the protection depth. Specifically, slot 582 includes a side storage surface 583, a forward storage surface 584, a triggering surface 586, a torque limiting surface 590, a protection surface 592, and a locking surface 594, terminating in an inclined surface 597.

Disposed along sides of the interior surface are a pair of axial shield guiding slots 596, seen clearly in FIG. 13I. At a forward end thereof, sleeve 580 terminates in a rim 598, including a rearwardly facing rim surface 598a.

The construction of system 500 in a storage operative orientation will now be explained making additional reference to FIG. 13K, which is a perspective view of the system 500, when constructed, to FIG. 14A, which is an oriented model view illustration of system 500, in a storage operative orientation, to FIG. 14B, which is a model side view planar illustration of the system 500 in the storage operative orientation, and to FIG. 14C, which is a sectional illustration of the system 500 in the storage operative orientation.

As seen, hypodermic needle 520 is inserted into needle receiving through-going bore 506 of luer housing 501, such that luer connector 502 is in fluid flow communication with needle 520. Needle 520 may be glued to luer housing 501, insert-molded with luer housing 501, or attached thereto in any other common way. Compression spring 530 is disposed about needle 520, such that a rearward facing end thereof engages protrusion 507 of base 504 of luer housing 501, and a forward facing end thereof engages protrusion 549 of wall portion 548 of guiding and locking ring 540, such that spring 530 is fixed relative to luer housing 501 and to guiding and locking ring 540, and that compression and torsion loads of spring 530 are applied to guiding and locking ring 540.

Shield 560 is disposed about barrel 542 of guiding and locking ring 540, such that a rearward facing surface 574 of shield 560 engages forward facing surface 545 of flange portion 544 of guiding and locking ring 540. Additionally, as seen clearly in FIG. 14C, teeth 554 of locking tabs 552 of guiding and locking ring 540 are disposed within circumferential groove 576 of shield 560. It will be appreciated that due to the connections between guiding and locking ring 540 and shield 560, the shield and guiding and locking ring move axially together as a single unit, guiding and locking ring 540 is rotatable relative to shield 560.

Guiding and locking ring 540, together with a rearward portion of shield 560, is disposed within outer sleeve 580, such that a forward portion of shield 560, including part of body portion 562 as well as tapered portion 564 and skin engaging surface 566, extends beyond the rim 598 of sleeve 580. At a rearward end thereof, outer sleeve 580 may be integrally formed with base 504, of luer housing 501.

Range limiting protrusions 570 of shield 560 are disposed within shield guiding slots 596 of sleeve 580, such that shield 560 is not rotatable relative to sleeve 580. Additionally, as seen clearly in FIG. 14A, guiding protrusions 546 of guiding and locking ring 540 are disposed within slots 582, and, in the storage operative orientation, lie against storage surfaces 583 and 584. The interface between guiding protrusions 546 and slots 582 transitions system 500 between operative orientations, as explained in further detail hereinbelow.

Figure 13K:
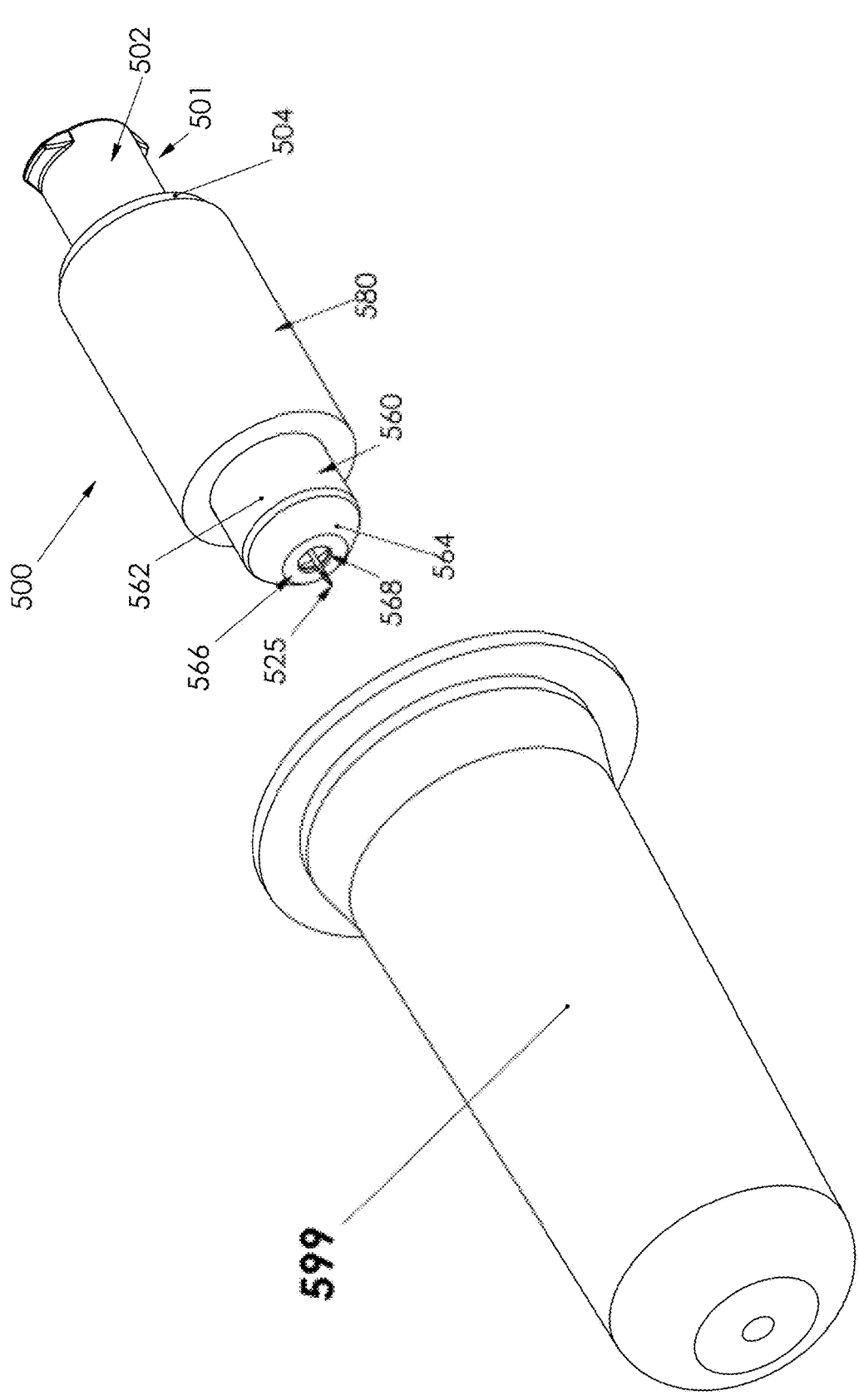
FIG. 13K is a perspective view of the system of FIG. 13A, when constructed.
Figure 14A:
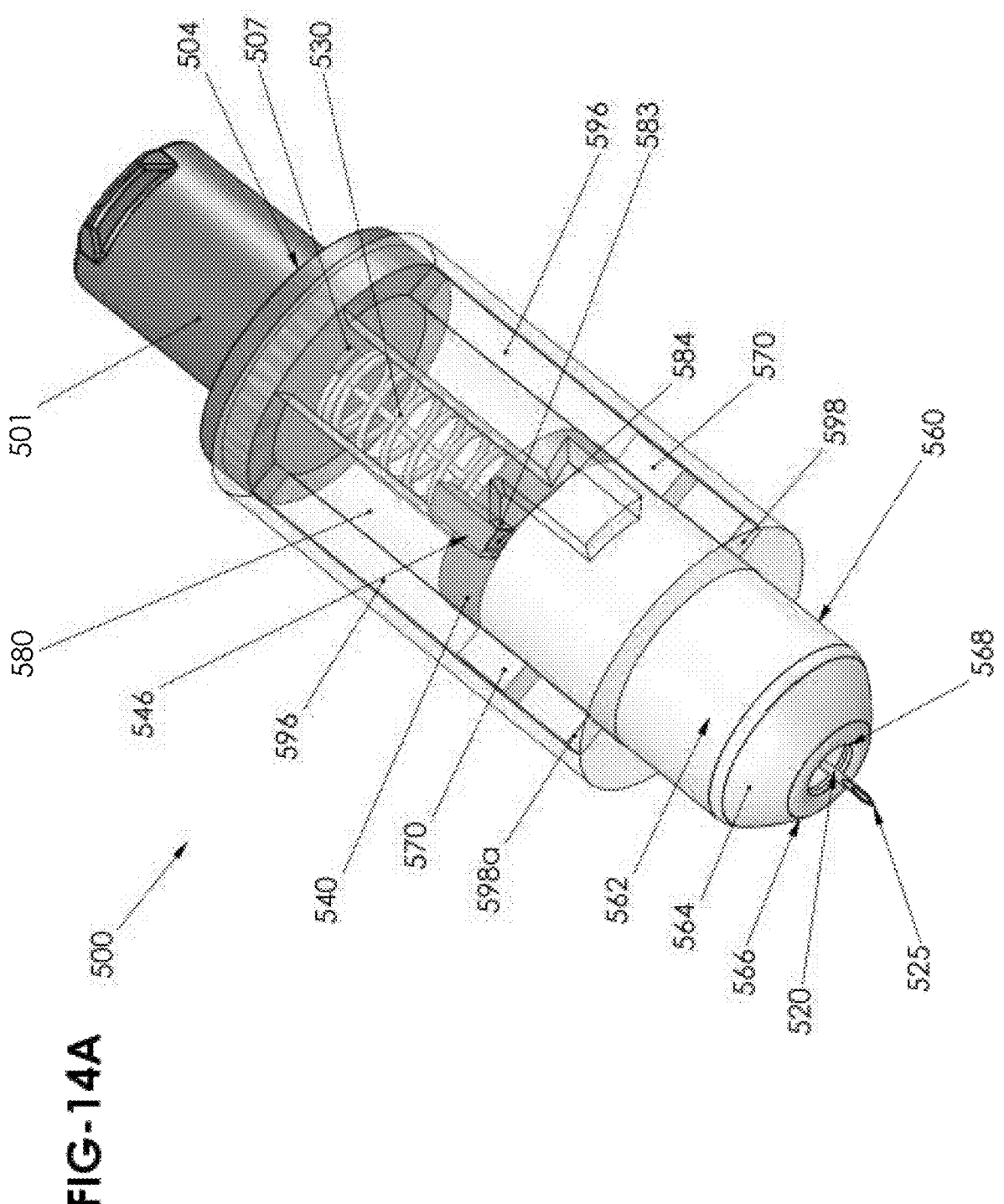
FIG. 14A is an oriented model view illustration of the system of FIGS. 13A to 13K, in a storage operative orientation.

As seen clearly in FIG. 13K, needle tip 525 of needle 520 extends through opening 568 of shield 560 and projects slightly forward of skin engaging surface 566. It will be appreciated that the exact location of storage surface 584 of slot 582 determines the extent to which shield 560 extends forwardly relative to sleeve 580, and thus the extent to which needle tip 525 protrudes from shield 560. Specifically, when storage surface 584 is located closer to the forward end of sleeve 580, the needle tip 525 protrudes to a lesser extent from shield 560, and when storage surface 584 is located closer to the rearward end of sleeve 580, the needle tip 525 protrudes to a greater extent from shield 560.

It will be appreciated that the fact that needle tip 525 protrudes from shield 560 is advantageous as it allows a user to better direct the needle toward the injection site, and, when using the needle with a syringe (not shown), to aspirate the syringe through the needle, remove some of the medicament from the syringe, remove air bubbles from the syringe, add medicament to the syringe, or otherwise manipulate the liquid in the syringe by manipulating a plunger of the syringe, without activating the protection mechanism of system 500.

In some embodiments, system 500 may be integrally formed with a syringe (not shown), such that fluid flow communication exists between the interior of luer connector 502 and the barrel of the syringe. In other embodiments, system 500 may be a standalone device, and may be connected to a syringe by the user, prior to use. The connection between the system 500 and the syringe may be by any suitable means, such as using the luer lock connection of luer housing 501, a snap fit connection, a fastener, adhesive, solvent, welding, or any other attachment form known to those skilled in the art.

Figure 15A:
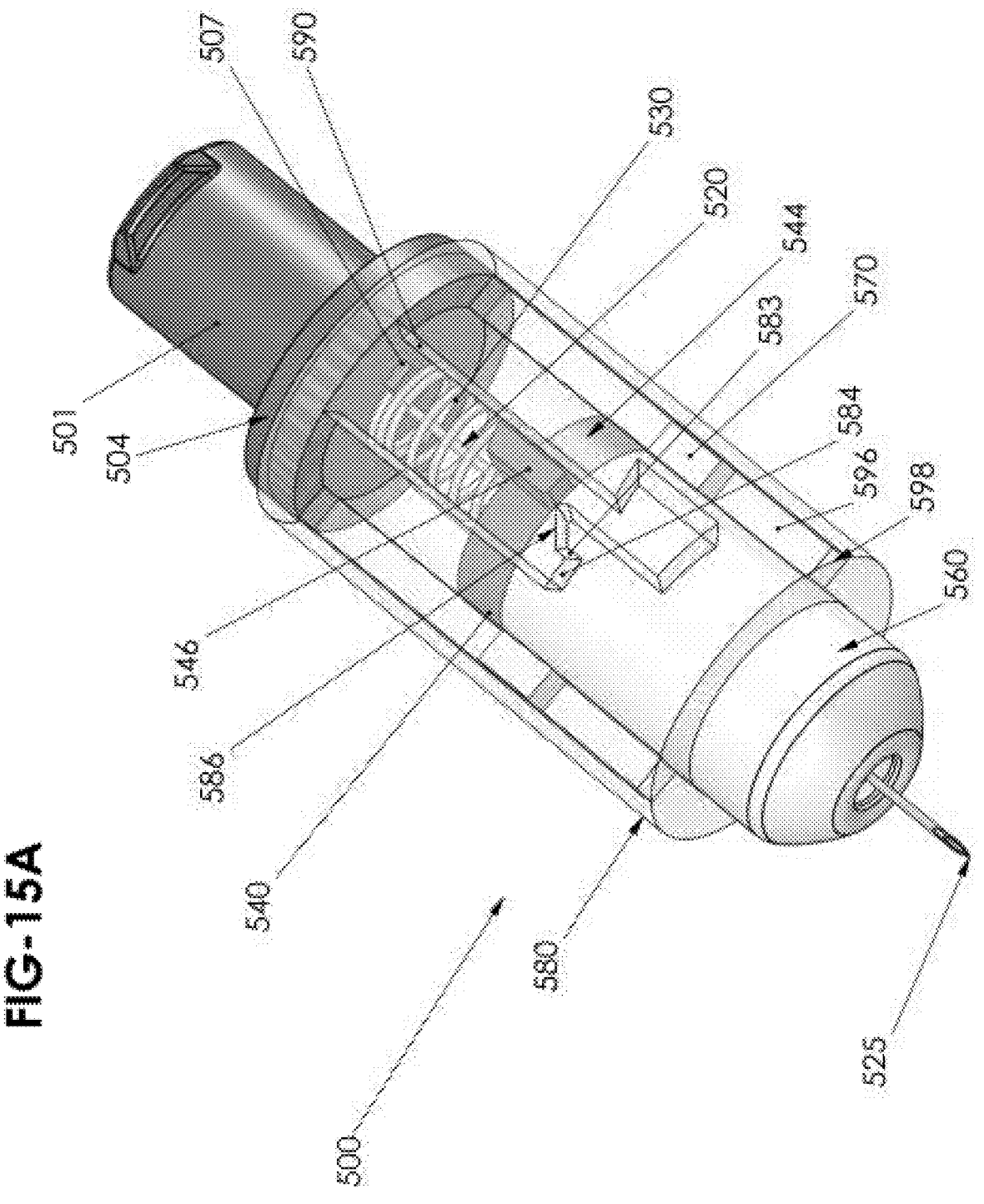
FIG. 15A is an oriented model view illustration of the system of FIGS. 13A to 13I, in a triggering operative orientation.
Figures 15B, 15C:
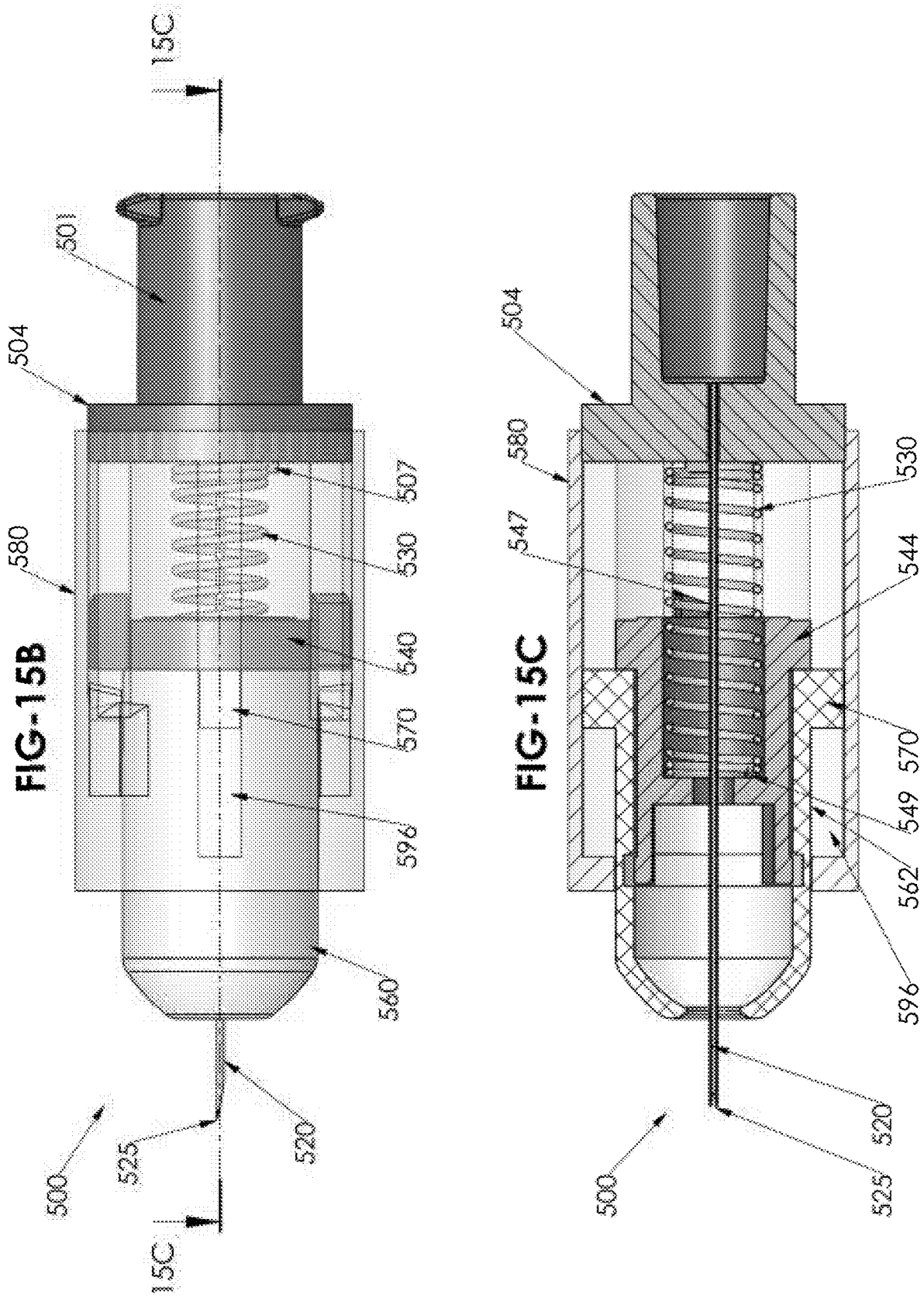
FIG. 15B is a model side view planar illustration of the system of FIG. 15A.
FIG. 15C is a sectional illustration of the system of FIG. 15A, taken along section lines 15C-15C in FIG. 15B.

Reference is now made to FIG. 15A, which is an oriented model view illustration of the system 500, in a triggering operative orientation, to FIG. 15B, which is a model side view planar illustration of the system 500 in the triggering operative orientation, and to FIG. 15C, which is a sectional illustration of system 500 in the triggering operative orientation.

In the triggering operative orientation, which occurs when the user begins pressing shield 560 against the injection site, shield 560 and guiding and locking ring 540 are guided rearwardly, against the compression force of spring 530. The rearward motion of shield 560 is guided by range limiting protrusions 570 moving rearwardly in shield guiding slots 596, and results in exposure of a greater portion of needle 520. Due to the rearward motion of guiding and locking ring 540, guiding protrusions 546 of guiding and locking ring 540 moves along slot 582 of outer sleeve 580 from forward storage surface 584, along side storage surface 583, to triggering surface 586, and can now slide along triggering surface 586 under the torsion force applied by spring 530 to torque limiting surface 590, which would cause rotation of guiding and locking ring 540, as seen clearly in FIG. 15A.

By sliding along triggering surface 586 of outer sleeve 580, system 500 reaches a safety feature triggering point. At this triggering point the safety feature is irreversibly activated, and once the shield is removed from the injection site the needle will become blocked by shield 560, as explained in further detail hereinbelow. On the other hand, if prior to reaching the triggering point the user removes pressure from the shield 560, for example by removing it from the injection site, the system 500 returns to its storage position shown in FIGS. 14A-14C, due to the release of spring 530 which causes guiding and locking ring 540 to move forwardly together with shield 560, resulting in guiding protrusions 546 of guiding and locking ring 540 returning to lie against storage surfaces 583 and 584 of slot 582.

It will be appreciated that the exact location of triggering surface 586 of slot 582 determines the extent to which shield 560 may be pressed prior to activation of the safety feature of system 500. Specifically, when triggering surface 586 is located closer to the forward end of outer sleeve 580, the safety feature is triggered by application of less pressure to shield 260, or the system is more sensitive to pressure, and when triggering surface 586 is located closer to the rearward end of outer sleeve 580, the safety feature is triggered by application of more pressure to shield 560.

Figure 16A:
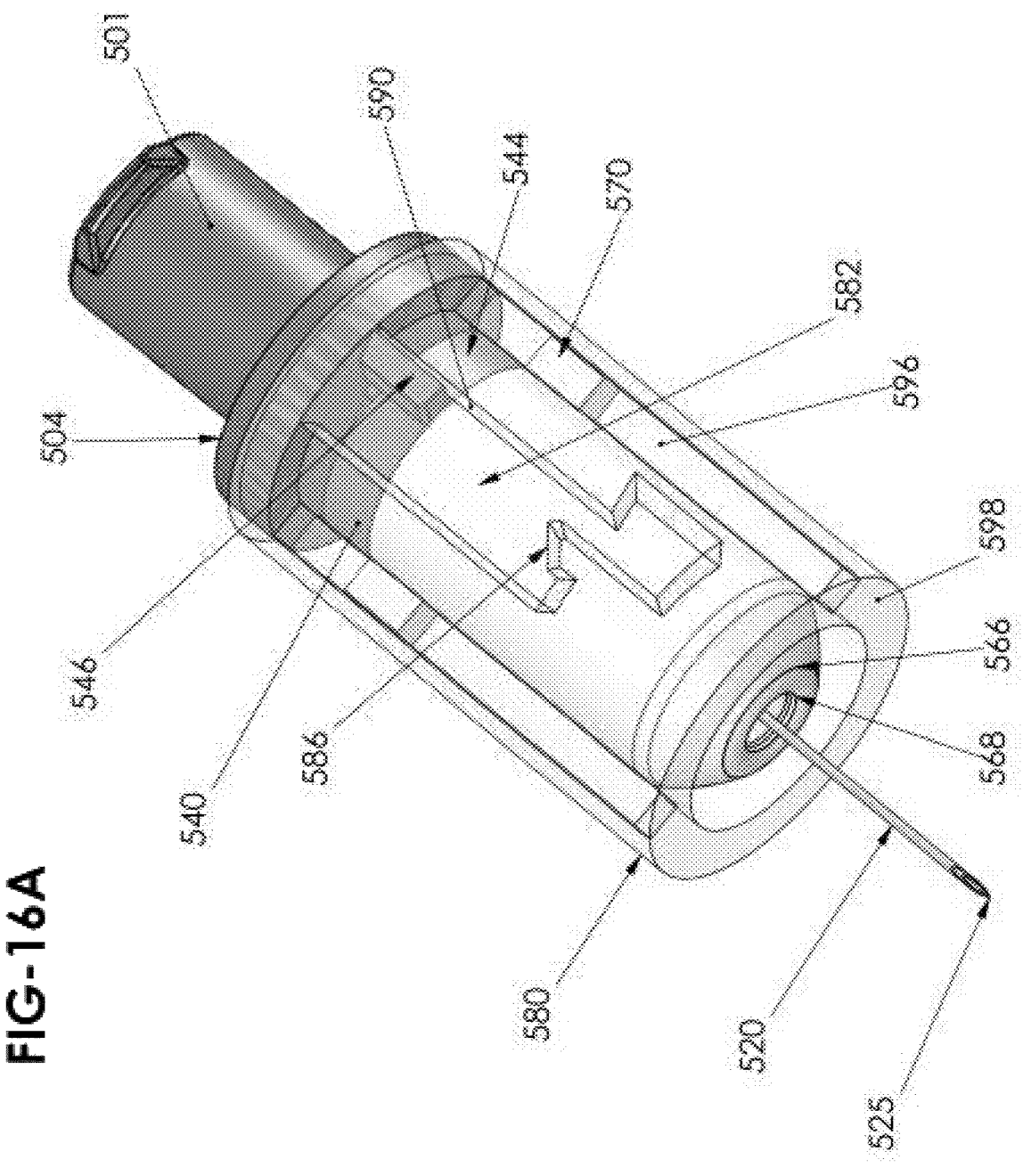
FIG. 16A is an oriented model view illustration of the system of FIGS. 13A to 13I, in an injection operative orientation.

Reference is now made to FIG. 16A, which is an oriented model view illustration of the system 500, in an injection operative orientation, to FIG. 16B, which is a model side view planar illustration of the system 500 in the injection operative orientation, and to FIG. 16C, which is a sectional illustration of system 500 in the injection operative orientation.

In the injection operative orientation, which occurs when the user continues pressing shield 560 against the injection site, typically to the full extent possible, shield 560 and guiding and locking ring 540 are guided rearwardly, against the compression force of spring 530. The rearward motion of shield 560 is guided by range limiting protrusions 570 moving rearwardly in shield guiding slots 596, and results in exposure of a greater portion of needle 520, up to the maximal needle penetration depth.

Due to the rearward motion of guiding and locking ring 540, guiding protrusions 546 of guiding and locking ring 540 moves rearwardly along torque limiting surface 590 of slot 582 of outer sleeve 580, away from triggering surface 586 under the torsion force applied by spring 530 to guiding and locking ring 540. Rearward motion of guiding protrusions 546 may continue, as long as additional pressure is applied to shield 560, until the spring is fully compressed, until the guiding protrusions 546 engage base 504 of luer housing 501 or any other applicable mechanical stop, or until shield 560 is fully depressed into sleeve 580 as seen clearly in FIG. 16C. When shield 560 is fully depressed into sleeve 580, the needle 520, and particularly needle tip 525, is at its full penetration depth.

Following needle penetration, the user may press a plunger (not shown) of a syringe (not shown) functionally associated with system 500 to inject the fluid contained in the syringe, as is well known in the art.

Figure 17A:
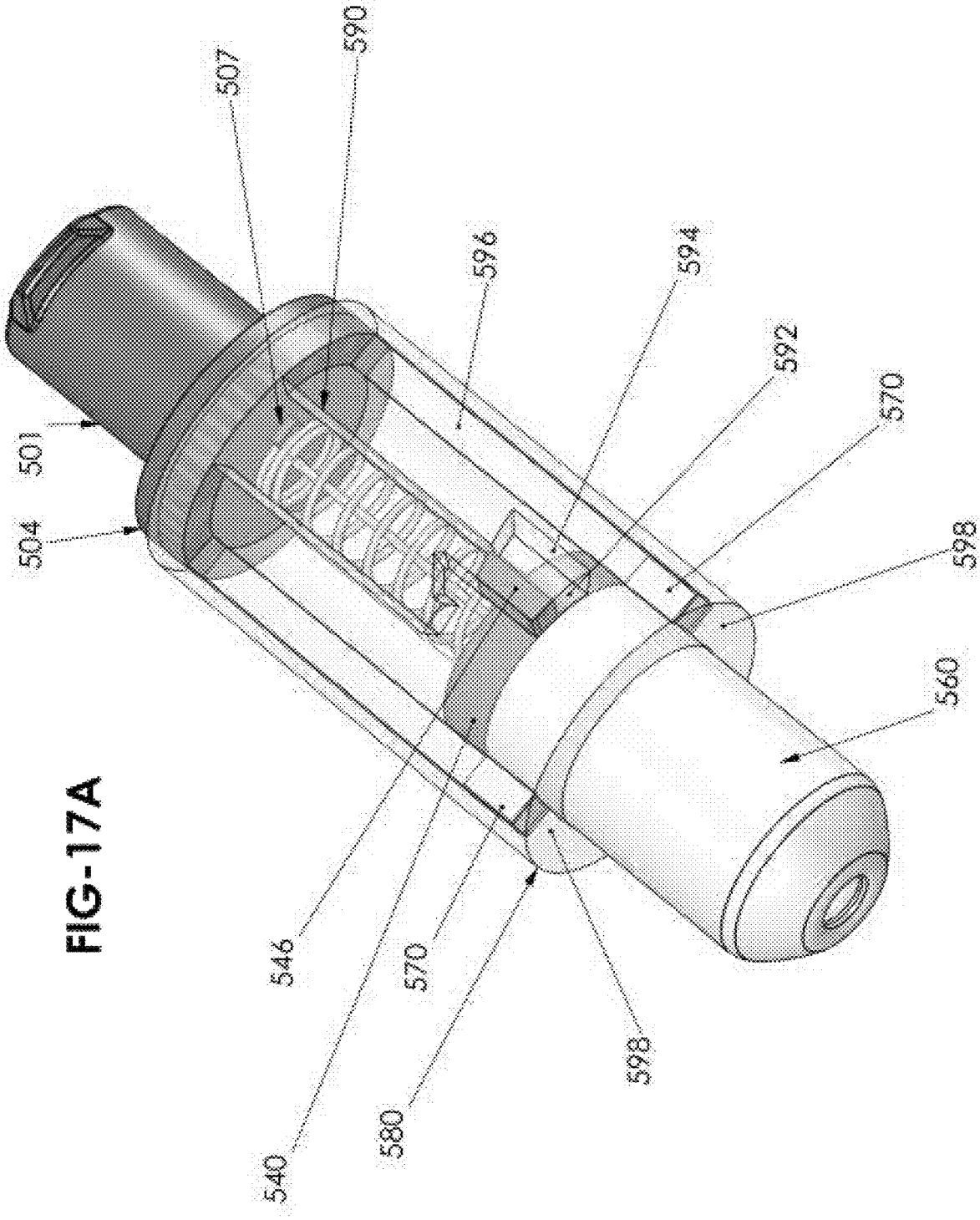
FIG. 17A is an oriented model view illustration of the system of FIGS. 13A to 13I, in a pre-locking operative orientation.

Reference is now made to FIG. 17A, which is an oriented model view illustration of the system 500, in a pre-locking operative orientation, to FIG. 17B, which is a model side view planar illustration of the system 500 in the pre-locking operative orientation, and to FIG. 17C, which is a sectional illustration of system 500 in the pre-locking operative orientation.

The pre-locking operative orientation occurs following injection, or following triggering of the safety feature of system 500, when the user releases the pressure from shield 560, for example by removing system 500 from the injection site, and just before the shield 560 locks around needle 520. As seen clearly in FIGS. 17A and 17C, following removal of pressure from shield 560, pressure is removed from spring 530, which decompresses and drives guiding and locking ring 540 forwardly, together with shield 560.

Forward motion of shield 560 is guided by forward motion of range limiting protrusions 570 thereof within slots 596 of outer sleeve 580, and is limited by forward facing surfaces 572 of protrusions 570 engaging rearward facing surface 598*a* of rim 598 of outer sleeve 580. Forward motion of guiding and locking ring 540 results in guiding protrusions 546 of guiding and locking ring 540 moving forwardly along torque limiting surface 590 of slot 582 of outer sleeve 580 to protection surface 592. When forward facing surfaces 572 of protrusions 570 engage rearward facing surface 598*a* of rim 598 of outer sleeve 580, or when guiding protrusions 546 engage the protection surfaces 592, the needle 520, and particularly needle tip 525, is disposed within shield 560.

It will be appreciated that the exact location of protection surface 592 of slot 582, or the distance of rearward facing surface 598*a* of outer sleeve 580 from base 504 of luer housing 501, determines the protection depth of needle 520, and particularly needle tip 525, or the extent to which shield 560 extends beyond needle tip 525. Specifically, protection surface 592 being located closer to the forward end of outer sleeve 580 results in a greater needle protection depth, whereas protection surface 592 being located closer to the rearward end of outer sleeve 580 results in a smaller needle protection depth.

Figure 18A:
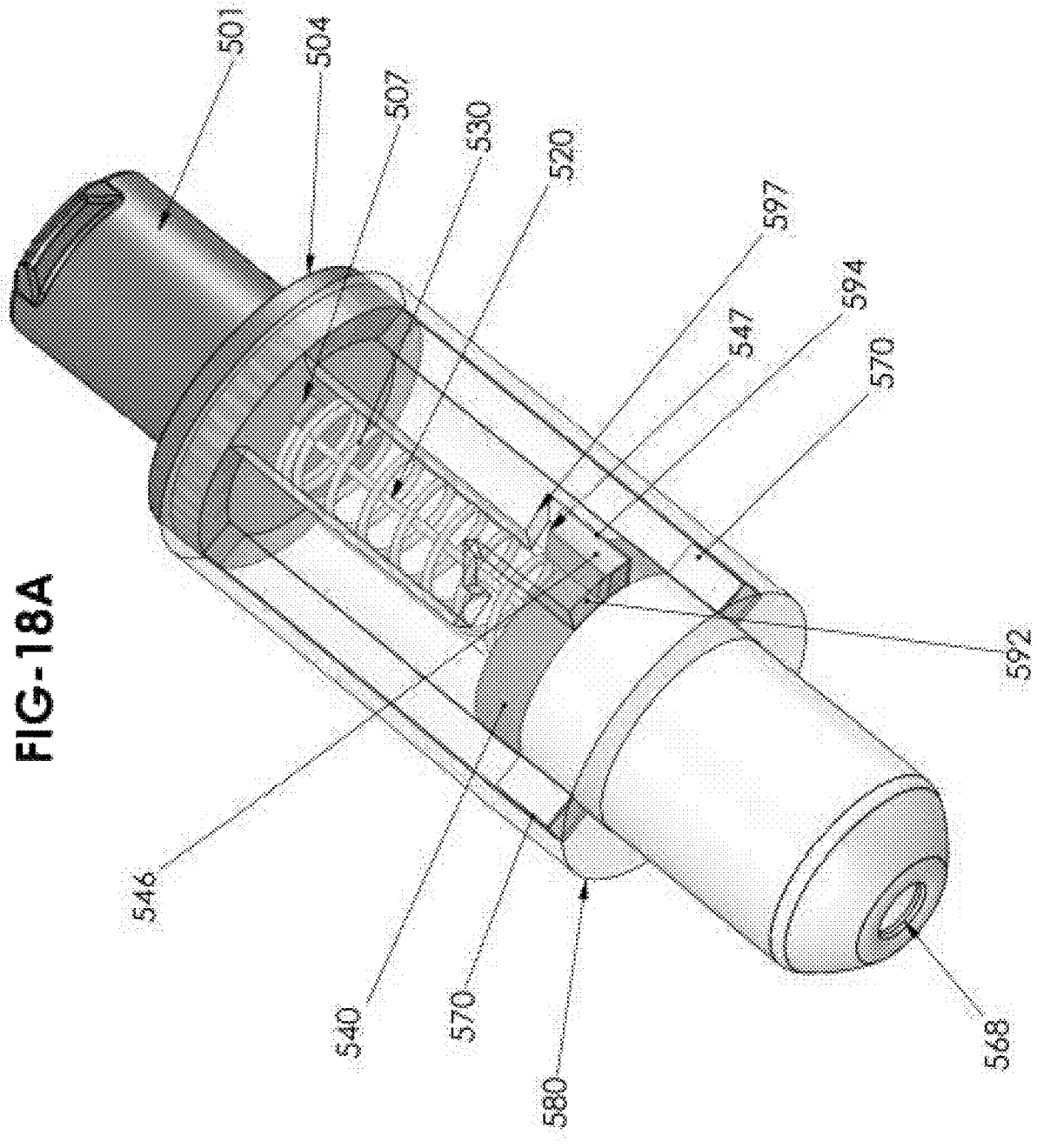
FIG. 18A is an oriented model view illustration of the system of FIGS. 13A to 13I, in a locked operative orientation.

Reference is now made to FIG. 18A, which is an oriented model view illustration of the system 500, in a locked operative orientation, to FIG. 18B, which is a model side view planar illustration of the system 500 in the locked operative orientation, and to FIG. 18C, which is a sectional illustration of system 500 in the locked operative orientation.

The locked operative orientation occurs automatically immediately following the pre-locking operative orientation, without requiring any additional action by the user. As seen clearly in FIG. 18A, guiding and locking ring 540 rotates under the torsion force of spring 530, such that guiding protrusion 546 of guiding and locking ring 540 slides along protection surface 592 to locking surface 594 of slot 582. The location of locking surface 594 determines the locking point of system 500.

When system 500 is in the locked position, inclined surface 547 of guiding protrusion 546 faces inclined surface 597 of slot 582. It will be appreciated that the distance between inclined surfaces 547 and 597 determines the "give", or maneuverability, of the shield 560 when assembly 500 is in the locked operative orientation. Specifically, a greater distance between the inclined surfaces would allow more movement of shield 560 in the locked operative orientation, whereas smaller distance between the two inclined surfaces would allow less, or no, movement of shield 560 in the locked operative orientation. The inclined surfaces provide higher safety in locking.

Reference is now made to FIG. 19A, which is an exploded view illustration of a system 600 for protection of a needle, the system being connectable to a syringe (not shown), according to a fourth embodiment of the teachings herein.

As seen in FIG. 19A, the system 600 includes a luer housing 601, which includes a hollow luer connector 602, and a base 604 having a forward facing surface 605 and including a needle receiving through-going bore 606 at the center thereof, the needle receiving through-going bore being in fluid flow communication with luer connector 602. Extending forwardly from forward facing surface 605 of base 604 are a pair of arms 608, each terminating in an angled surface 609.

Luer housing 601 is connectable to a syringe or to any other suitable luer connector, as described hereinbelow. Additionally, luer connector 602 may be replaced by any other suitable connector known in the art for connection to a syringe.

A hypodermic needle 620, which may be any needle known in the art, terminating in a sharp needle tip 625, is adapted to be received in needle receiving through-going bore 606 and thus to be in fluid communication with luer connector 602. Needle 620 can be glued to luer housing 601, insert-molded with luer housing 601 or attached thereto in any other common way.

System 600 further includes a compression spring 630, a guiding and locking ring 640, a shield 660, and an outer sleeve 680. The system may be packaged in a packaging (not shown) similar to packaging 599 of FIG. 13A. While spring 630 is illustrated and described herein as a compression spring, the system may be designed to use any other suitable biasing element, such as a tension spring, a constant-force spring, an integrally formed plastic spring, or any other resilient element such as a rubber, plastic or elastomeric element.

As seen clearly in FIG. 19B, which shows a detailed view of guiding and locking ring 640 forming part of system 600, the ring 640 may be top-to-bottom and side-to-side symmetrical. Ring 640 includes a ring-shaped body portion 642 including a forward facing surface 645 and having two guiding protrusions 646 extending radially outwardly therefrom, each terminating in a rearward facing surface 646a, which may, in some embodiments, be inclined. Extending forwardly from each guiding protrusion 646 is a narrower resilient finger 647. Extending forwardly from body portion 642, on either side thereof, are a pair of fingers 652, each terminating in a radially outwardly facing tooth 654. Fingers 652 are connected, at a forward portion thereof disposed rearwardly of teeth 654, by a partial wall portion 648 having a needle opening 650 disposed at the center thereof.

Returning to FIG. 19A, and referring additionally to FIG. 19C, which is a side view planar illustration of shield 660 and to FIG. 19D, which is a sectional illustration of shield 660 taken along section lines 19D-19D in FIG. 19C, it is seen that shield 660 may be side-to-side and top-to-bottom symmetrical, and includes a cylindrical body portion 662. At a forward end thereof, body portion 662 extends toward a tapered portion 664 terminating in a skin engaging surface 666 including, at a center thereof, an opening 668. Protruding from an exterior surface of body portion 662, at a rearward end thereof, are range limiting protrusions 670 each including a forward facing surface 672. Body portion

662 as well as range limiting protrusions 670 terminate at a rearward end thereof in a rearward facing surface 674. As seen with particular clarity in FIG. 19D, disposed along an interior surface of body portion 662 is a circumferential groove 676, adapted for connection of shield 660 to additional components of system 600, as described in further detail hereinbelow.

Figure 19G:
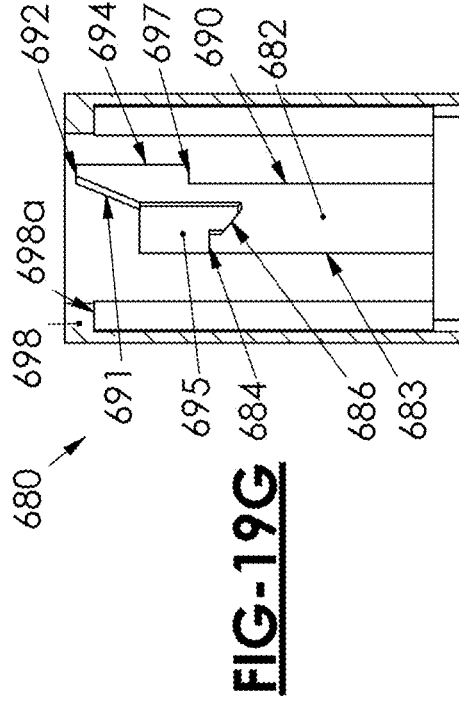
FIGS. 19F and 19G are sectional illustrations of the outer sleeve, the sectional illustrations taken along respective section lines 19F-19F and 19G-19G in FIG. 19E.
Figure 19E:
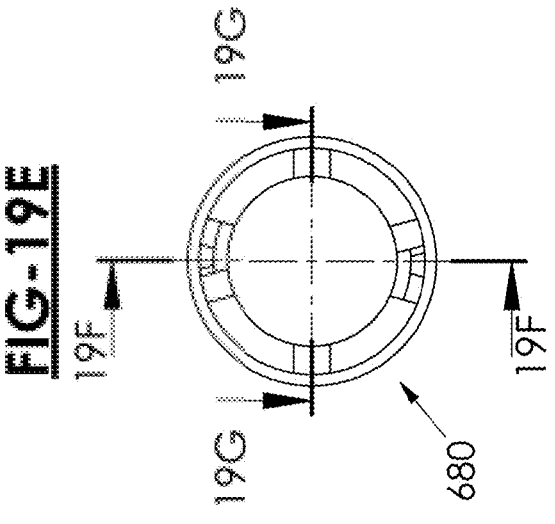
FIG. 19E is a front view planar illustration of an outer sleeve forming part of the system of FIG. 19A.
Figure 19F:
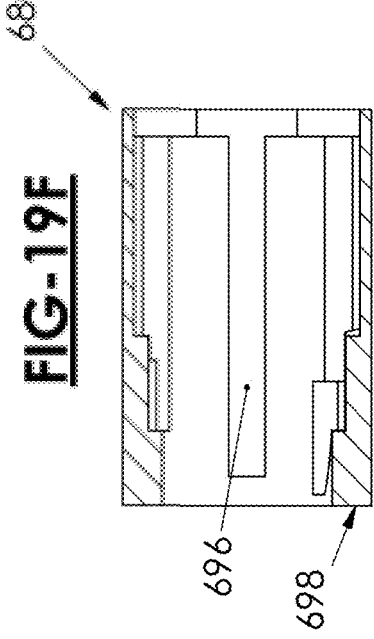

Turning to FIG. 19E, which is a front view planar illustration of outer sleeve 680, and to FIGS. 19F and 19G, which are sectional illustrations of the outer sleeve 680, it is seen that sleeve 680 is generally tubular, and has formed, in a rearward portion of an interior surface thereof, one or more guiding slots 682, one of which seen clearly in FIG. 19F. In some embodiments, the slot 682 does not extend through the entire wall thickness of sleeve 680, such that the exterior surface of sleeve 680 is completely tubular.

As explained in further detail hereinbelow, slot 682 includes multiple surfaces which define the stages of operation of system 600 and the needle protection depth. Specifically, slot 682 includes a side storage surface 683, a forward storage surface 684, a triggering surface 686, a rotation limiting surface 690, a slanted guiding surface 691, a protection surface 692, and locking surfaces 694 and 697. In some embodiments, surface 697 may be inclined, similarly to surface 597 of FIG. 13I. Extending forwardly of forward storage surface 684 and of triggering surface 686 is an ingress region 695, at which the thickness of material remaining of sleeve 680 is greater than the thickness remaining in slot 682, while still forming an ingress relative to the total thickness of sleeve 680.

Disposed along sides of the interior surface are a pair of axial shield guiding slots 696, seen clearly in FIG. 19G. At a forward end thereof, sleeve 680 terminates in a rim 698, including a rearwardly facing rim surface 698a.

The construction of system 600 in a storage operative orientation will now be explained making additional reference to FIG. 19H, which is a perspective view of the system 600, when constructed, to FIG. 20A, which is an oriented model view illustration of system 600, in a storage operative orientation, to FIG. 20B, which is a model side view planar illustration of the system 600 in the storage operative orientation, and to FIG. 20C, which is a sectional illustration of the system 600 in the storage operative orientation.

As seen, hypodermic needle 620 is inserted into needle receiving through-going bore 606 of luer housing 601, such that luer connector 602 is in fluid flow communication with needle 620. Compression spring 630 is disposed about needle 620, such that a rearward facing end thereof engages forward facing surface 605 of base 604 of luer housing 601, and a forward facing end thereof engages wall portion 648 of guiding and locking ring 640, such that compression loads of spring 630 are applied to guiding and locking ring 640. Shield 660 is disposed about fingers 652 of guiding and locking ring 640, such that rearward facing surface 674 of shield 660 engages forward facing surface 645 of body portion 642 of guiding and locking ring 640. Additionally, as seen clearly in FIG. 20C, teeth 654 of fingers 652 of guiding and locking ring 640 are disposed within circumferential groove 676 of shield 660. It will be appreciated that due to the connections between guiding and locking ring 640 and shield 660, the shield and guiding and locking ring move axially together as a single unit, while guiding and locking ring 640 is rotatable relative to shield 660.

Guiding and locking ring 640, together with a rearward portion of shield 660, is disposed within outer sleeve 680, such that a forward portion of shield 660, including part of body portion 662 as well as tapered portion 664 and skin engaging surface 666, extends beyond the rim 698 of sleeve 680. At a rearward end thereof, outer sleeve 680 may be integrally formed with, or connected to, base 604 of luer housing 601.

Range limiting protrusions 670 of shield 660 are disposed within shield guiding slots 696 of sleeve 680, such that shield 660 is not rotatable relative to sleeve 680. Additionally, as seen clearly in FIG. 20A, guiding protrusions 646 of guiding and locking ring 640 are disposed within slots 682, and, in the storage operative orientation, lie against storage surfaces 683 and 684, while fingers 647 extend into ingress regions 695 forwardly of forward storage surface 684. As can be seen clearly in FIG. 20A, in the storage operative orientation, fingers 647 are not loaded. The interface of guiding protrusions 646 and fingers 647 with slots 682 and ingress regions 695 moves system 600 between operative orientations, as explained in further detail hereinbelow.

In an alternative embodiment, shield 660 may be formed with a rearward facing surface (not shown), for example disposed on an internal surface of tapered portion 664, and guiding and locking ring 640 may be formed without the wall portion 648, such that the forward facing end of spring 630 would engage the rearward facing surface formed on the internal surface of tapered portion 664. In such a design, the compression load of spring 630 would be applied directly to shield 660 and not to guiding and locking ring 640. In this alternative design the friction between the guiding and locking ring 640 and the shield 660 would be significantly lower, so that rotation of the locking ring 640 would be easier and less torque would be required.

Figure 20A:
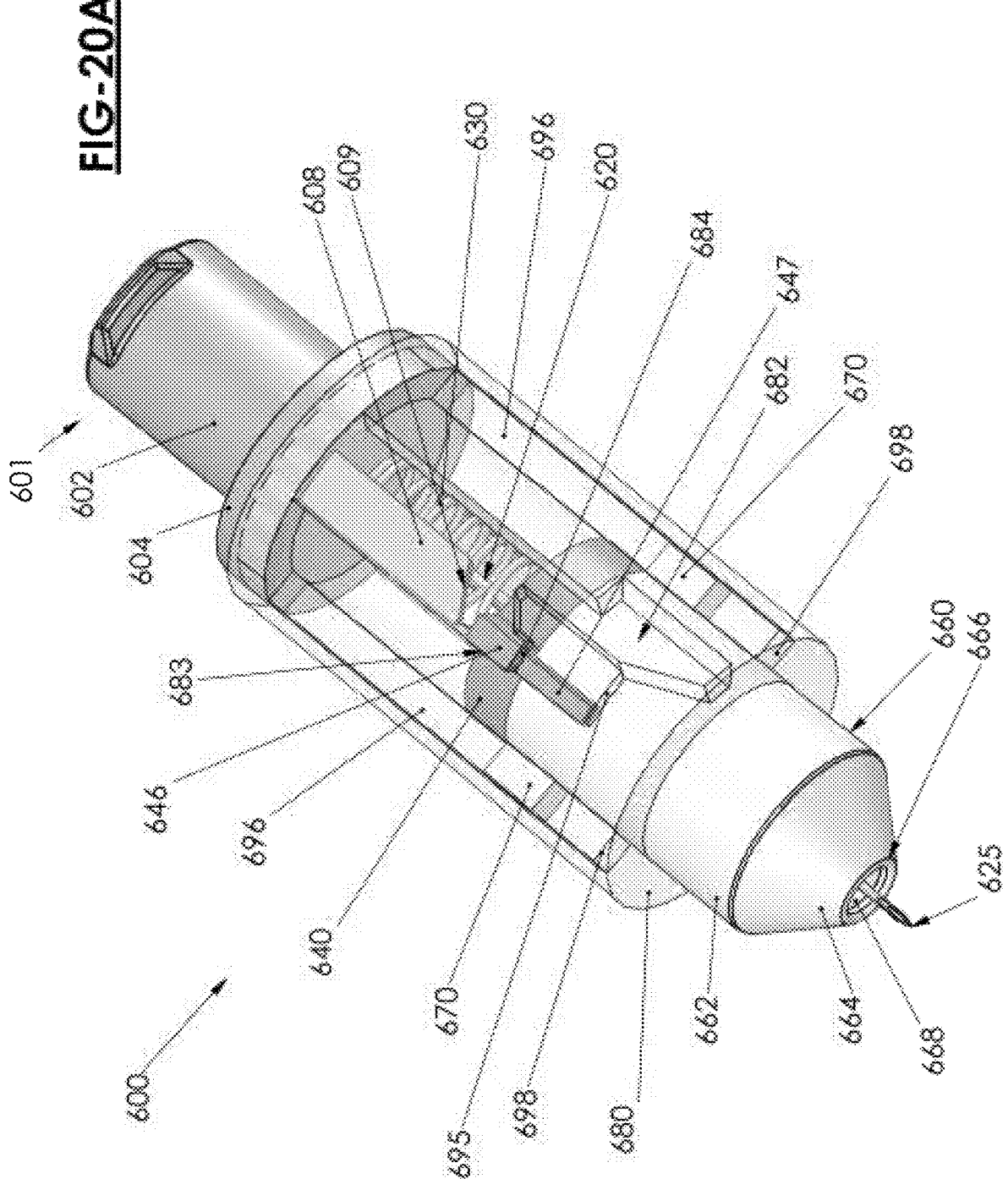
FIG. 20A is an oriented model view illustration of the system of FIGS. 19A to 19H, in a storage operative orientation.
Figures 20B, 20C:
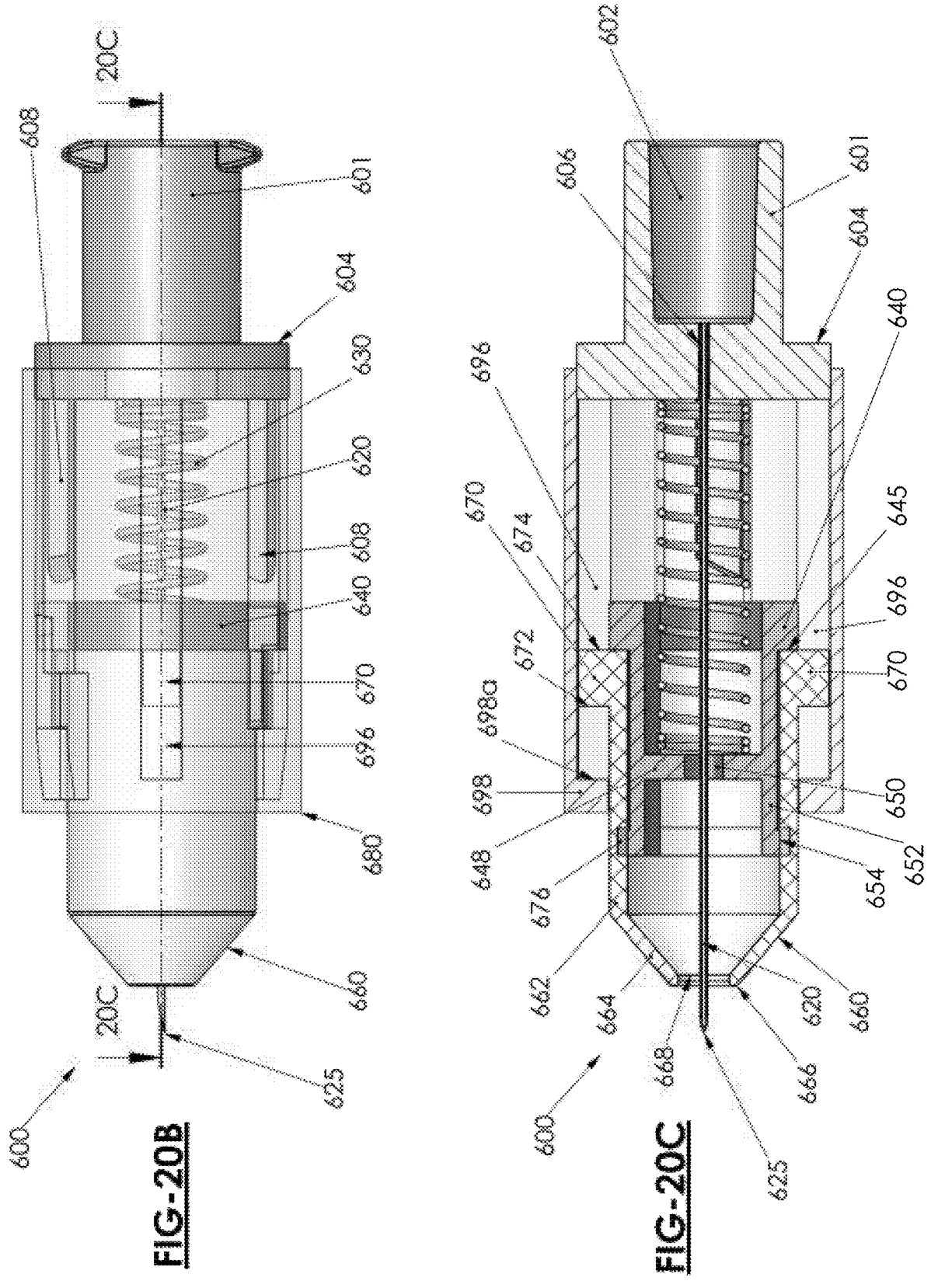
FIG. 20B is a model side view planar illustration of the system of FIG. 20A.
FIG. 20C is a sectional illustration of the system of FIG. 20A, taken along section lines 20C-20C in FIG. 20B.

As seen clearly in FIGS. 19H and 20A, needle tip 625 of needle 620 extends through opening 668 of shield 660 and projects slightly forward of skin engaging surface 666. It will be appreciated that the exact location of storage surface 684 of slot 682 determines the extent to which shield 660 extends forwardly relative to sleeve 680, and thus the extent to which needle tip 625 protrudes from shield 660. Specifically, when storage surface 684 is located closer to the forward end of sleeve 680, the needle tip 625 protrudes to a lesser extent from shield 660, and may, in some embodiments not illustrated herein, not protrude at all from the shield 660 in the storage operative orientation. Conversely, when storage surface 684 is located closer to the rearward end of sleeve 680, the needle tip 625 protrudes to a greater extent from shield 660.

It will be appreciated that the fact that needle tip 625 protrudes from shield 660 is advantageous as it allows a user better direct the needle to the injection site, and when using the needle with a syringe (not shown), allows the user to aspirate the syringe, remove some of the medicament from the syringe, remove air bubbles from the syringe, add medicament to the syringe, or otherwise manipulate the liquid in the syringe by manipulating a plunger of the syringe, without activating the protection mechanism of system 600.

In some embodiments, system 600 may be integrally formed with a syringe (not shown), such that fluid flow communication exists between the interior of luer connector 602 and the barrel of the syringe. In other embodiments, system 600 may be a standalone device, and may be connected to a syringe by the user, prior to use. The connection between the system 600 and the syringe may be by any suitable means, such as using a luer lock of luer housing 601, or using a snap fit connection, a fastener, adhesive, solvent, welding, or any other attachment form known to those skilled in the art.

Figure 21A:
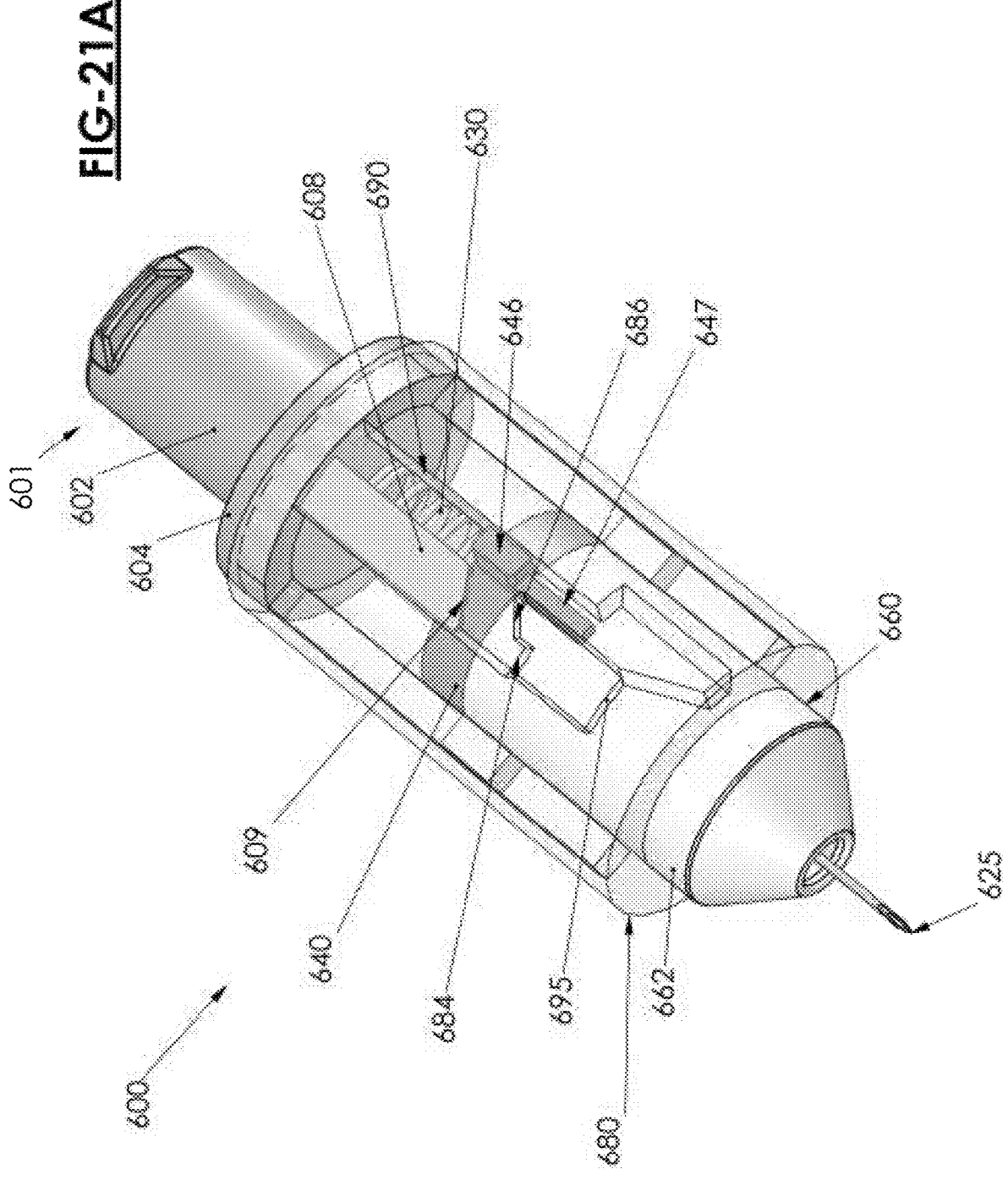
FIG. 21A is an oriented model view illustration of the system of FIGS. 19A to 19H, in a triggering operative orientation.
Figures 21B, 21C:
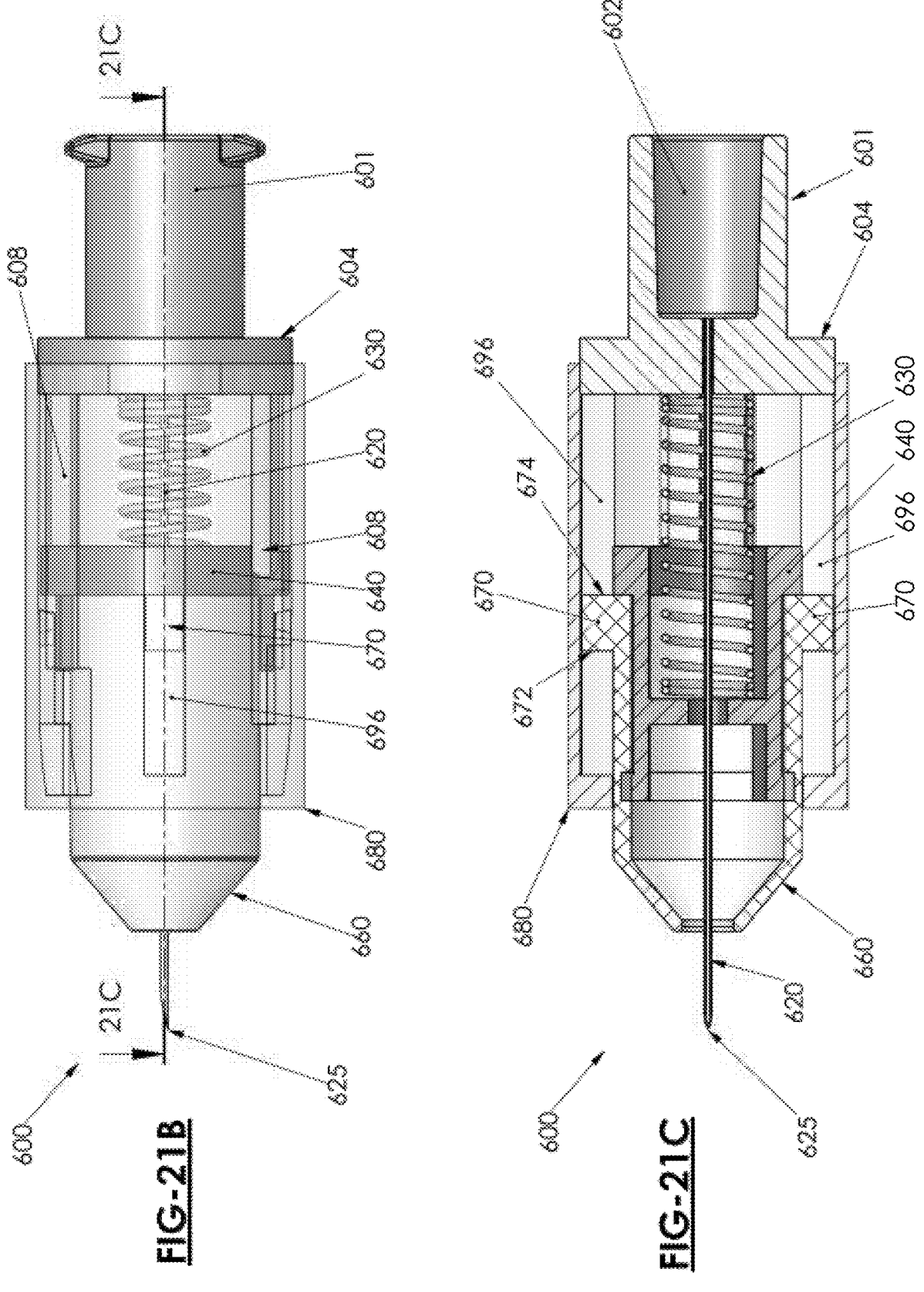
FIG. 21B is a model side view planar illustration of the system of FIG. 21A.
FIG. 21C is a sectional illustration of the system of FIG. 21A, taken along section lines 21C-21C in FIG. 21B.

Reference is now made to FIG. 21A, which is an oriented model view illustration of the system 600, in a triggering operative orientation, to FIG. 21B, which is a model side view planar illustration of the system 600 in the triggering operative orientation, and to FIG. 21C, which is a sectional illustration of system 600 in the triggering operative orientation.

In the triggering operative orientation, which occurs when the user begins pressing shield 660 against the injection site, shield 660 and guiding and locking ring 640 are guided rearwardly, against the compression force of spring 630. The rearward motion of shield 660 is guided by range limiting protrusions 670 moving rearwardly in shield guiding slots 696, and results in exposure of a greater portion of needle 620. Due to the rearward motion of guiding and locking ring 640, guiding protrusions 646 of guiding and locking ring 640 moves along slot 682 of outer sleeve 680 from forward storage surface 684 to triggering surface 686, and can now slide between triggering surface 686 and angled surface 609 of arms 608 of luer housing 601, which causes rotation of guiding and locking ring 640 relative to shield 660, until reaching rotation limiting surface 690, as seen clearly in FIG. 21A. Due to the rotation of guiding and locking ring 640, fingers 647 move from ingress region 695 to being disposed within slot 682.

By sliding along triggering surface 686 of outer sleeve 680, system 600 reaches a safety feature triggering point. At this triggering point the safety feature is irreversibly activated, and once the shield is removed from the injection site the needle will become blocked by shield 660, as explained in further detail hereinbelow. On the other hand, if prior to reaching the triggering point the user removes pressure from the shield 660, for example by removing it from the injection site, the system 600 returns to its storage position shown in FIGS. 20A-20C, due to the release of spring 630 which causes guiding and locking ring 640 to rotate back towards side storage surface 683 and to move forwardly together with shield 660, resulting in guiding protrusions 646 of guiding and locking ring 640 returning to lie against storage surfaces 683 and 684 of slot 682.

It will be appreciated that the exact location of triggering surface 686 of slot 682 and the location of angled surfaces 609 of arms 608 of luer housing 601 determines the extent to which shield 660 may be pressed prior to activation of the safety feature of system 600. Specifically, when triggering surface 686 and angled surfaces 609 are located closer to the forward end of outer sleeve 680, the safety feature is triggered by application of less pressure to shield 660, or the system is more sensitive to pressure, and when triggering surface 686 and angled surfaces 609 are located closer to the rearward end of outer sleeve 680, the safety feature is triggered by application of more pressure to shield 660.

Figure 22A:
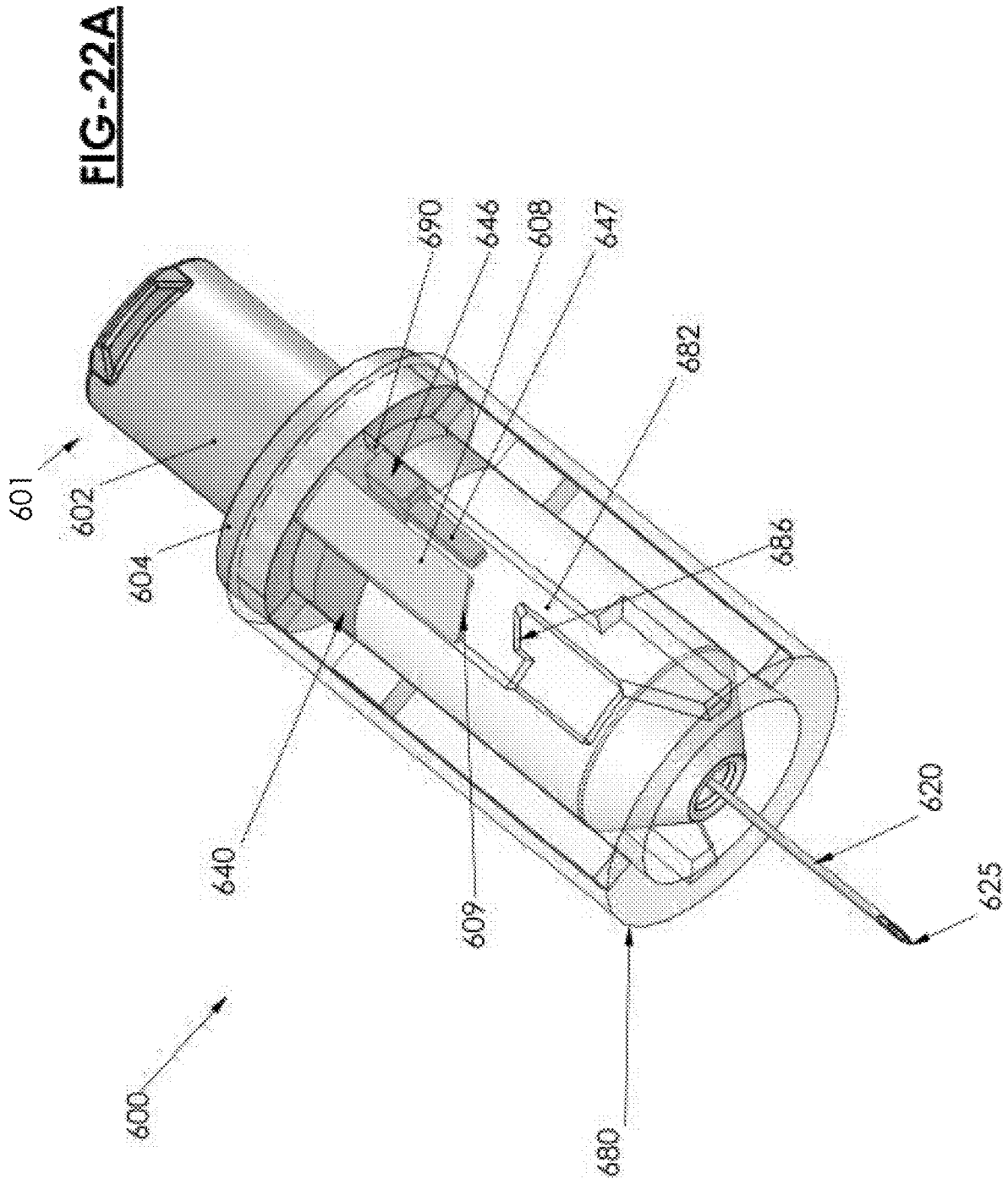
FIG. 22A is an oriented model view illustration of the system of FIGS. 19A to 19H, in an injection operative orientation.
Figures 22B, 22C:
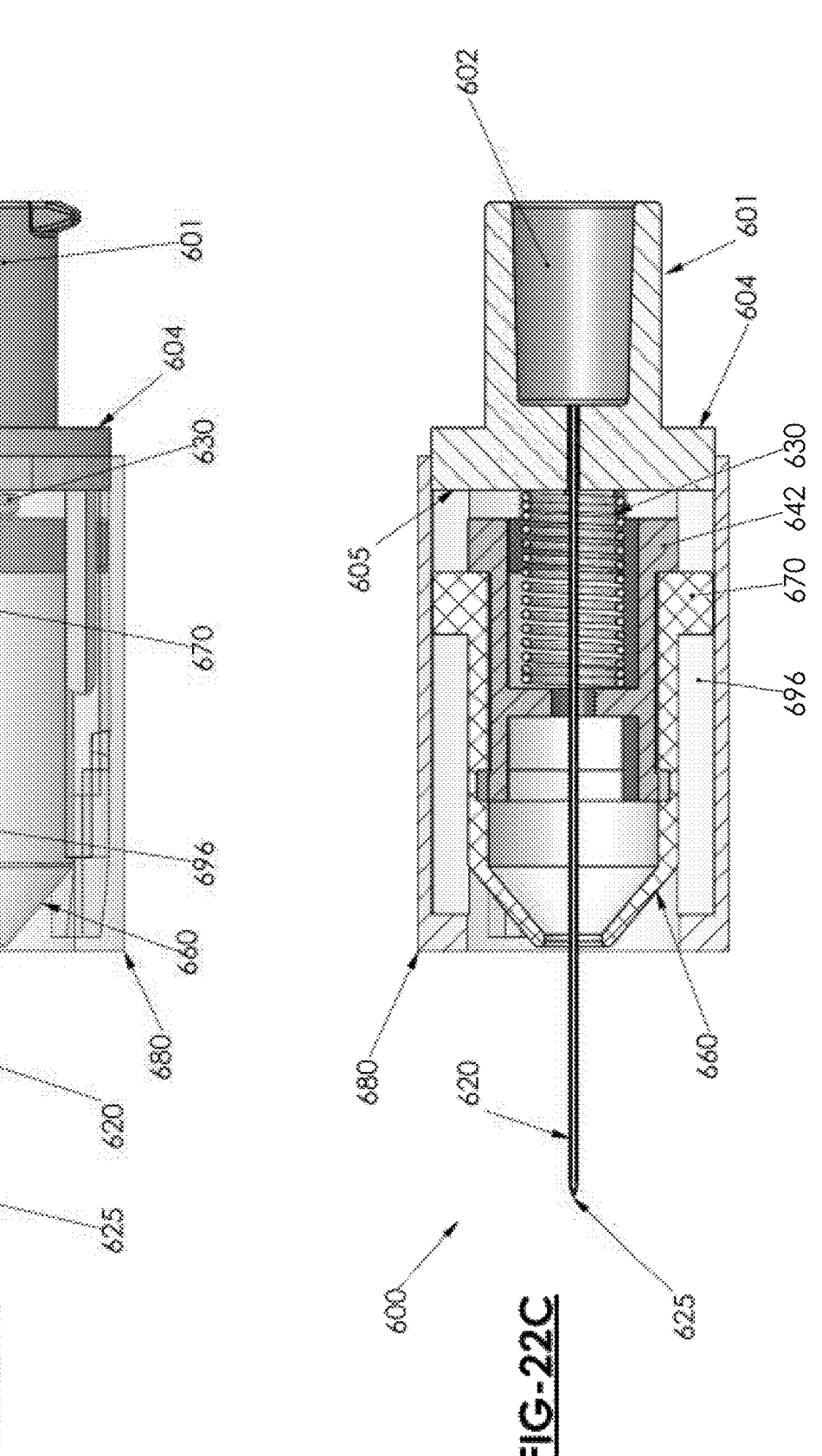
FIG. 22B is a model side view planar illustration of the system of FIG. 22A.
FIG. 22C is a sectional illustration of the system of FIG. 22A, taken along section lines 22C-22C in FIG. 22B.

Reference is now made to FIG. 22A, which is an oriented model view illustration of the system 600, in an injection operative orientation, to FIG. 22B, which is a model side view planar illustration of the system 600 in the injection operative orientation, and to FIG. 22C, which is a sectional illustration of system 600 in the injection operative orientation.

In the injection operative orientation, which occurs when the user continues pressing shield 660 against the injection site, typically to the full extent possible, shield 660 and guiding and locking ring 640 are guided rearwardly, against the compression force of spring 630. The rearward motion of shield 660 is guided by range limiting protrusions 670 moving rearwardly in shield guiding slots 696, and results in exposure of a greater portion of needle 620, up to the maximal needle penetration depth.

Due to the rearward motion of guiding and locking ring 640, guiding protrusions 646 of guiding and locking ring 640 moves rearwardly between rotation limiting surface 690 of slot 682 of outer sleeve 680 and arm 608 of luer housing 601, away from triggering surface 686. Rearward motion of guiding protrusions 646 may continue, as long as additional pressure is applied to shield 660, until the spring is fully compressed, until the guiding protrusions 646 engage forward surface 605 of base 604 of luer housing 601 or any other applicable mechanical stop, or until shield 660 is fully depressed into sleeve 680 as seen clearly in FIG. 22C. When shield 660 is fully depressed into sleeve 680 the needle 620, and particularly needle tip 625, is at its full penetration depth.

Following needle penetration, the user may press a plunger (not shown) of a syringe (not shown) functionally associated with system 600 to inject the fluid contained in the syringe, as is well known in the art.

Figure 23A:
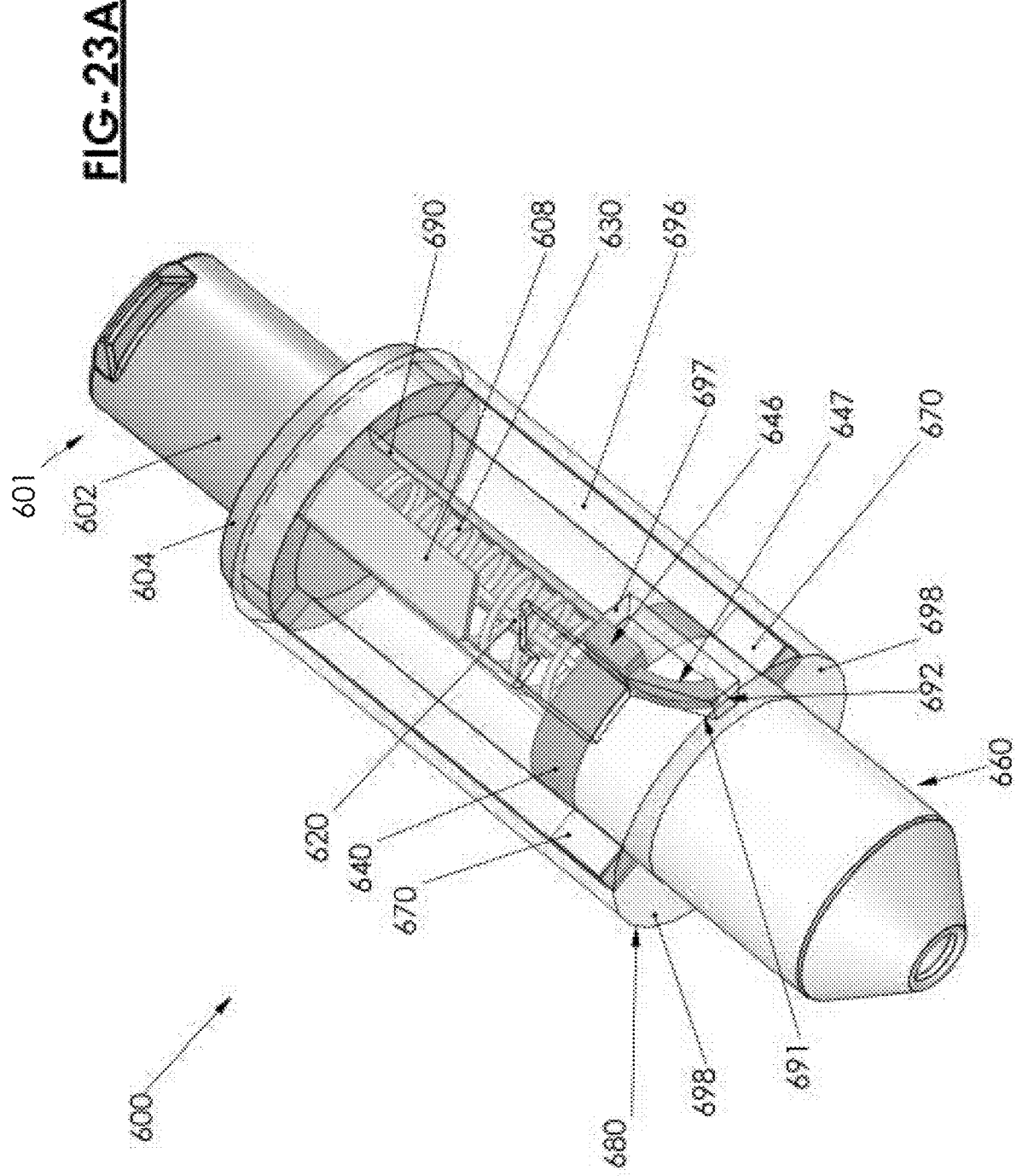
FIG. 23A is an oriented model view illustration of the system of FIGS. 19A to 19H, in a pre-locking operative orientation.
Figures 23B, 23C:
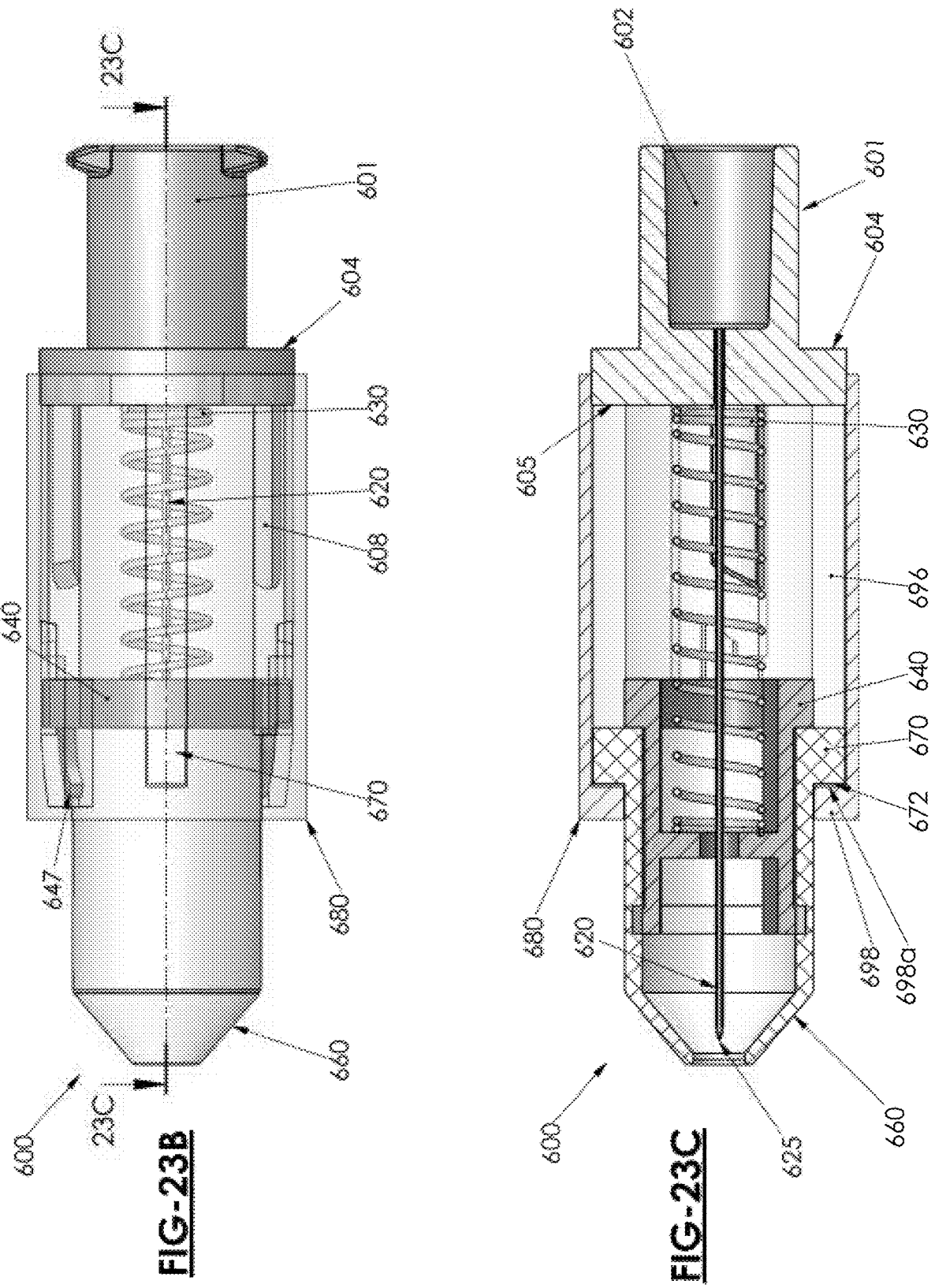
FIG. 23B is a model side view planar illustration of the system of FIG. 23A.
FIG. 23C is a sectional illustration of the system of FIG. 23A, taken along section lines 23C-23C in FIG. 23B.

Reference is now made to FIG. 23A, which is an oriented model view illustration of the system 600, in a pre-locking operative orientation, to FIG. 23B, which is a model side view planar illustration of the system 600 in the pre-locking operative orientation, and to FIG. 23C, which is a sectional illustration of system 600 in the pre-locking operative orientation.

The pre-locking operative orientation occurs following injection, or following triggering of the safety feature of system 600, when the user releases the pressure from shield 660, for example by removing system 600 from the injection site, and just before the shield 660 locks around needle 620. As seen clearly in FIGS. 23A and 23C, following removal of pressure from shield 660, pressure is removed from spring 630, which decompresses and drives guiding and locking ring 640 forwardly, together with shield 660.

Forward motion of shield 660 is guided by forward motion of range limiting protrusions 670 thereof within slots 696 of outer sleeve 680, and is limited by forward facing surfaces 672 of protrusions 670 engaging rearward facing surface 698a of rim 698 of outer sleeve 680.

Forward motion of guiding and locking ring 640 results in guiding protrusions 646 of guiding and locking ring 640 moving forwardly along rotation limiting surface 690 of slot 682 of outer sleeve 680, until fingers 647 engage angled surface 691 and bend along it. At this stage, the needle 620, and particularly needle tip 625, is disposed within shield 660.

It will be appreciated that the exact location of rearward facing surface 698a of outer sleeve 680 determines the protection depth of needle 620, and particularly needle tip 625, or the extent to which shield 660 extends beyond needle tip 625. Specifically, rearward facing surface 698a being located closer to the forward end of outer sleeve 680 results in a greater needle protection depth, whereas rearward facing surface 698a being located closer to the rearward end of outer sleeve 680 results in a smaller needle protection depth.

Figure 24A:
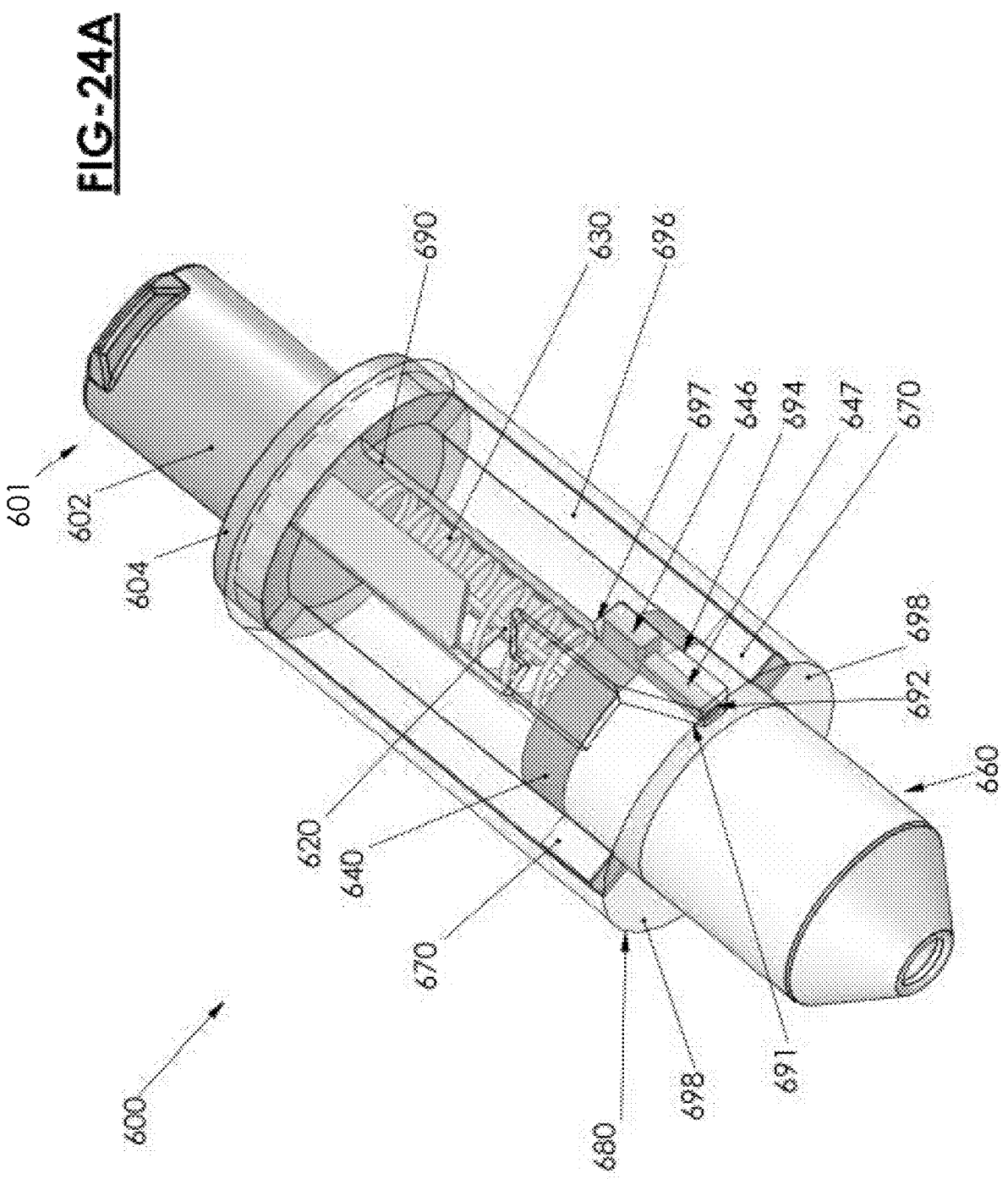
FIG. 24A is an oriented model view illustration of the system of FIGS. 19A to 19I, in a locked operative orientation.
Figures 24B, 24C:
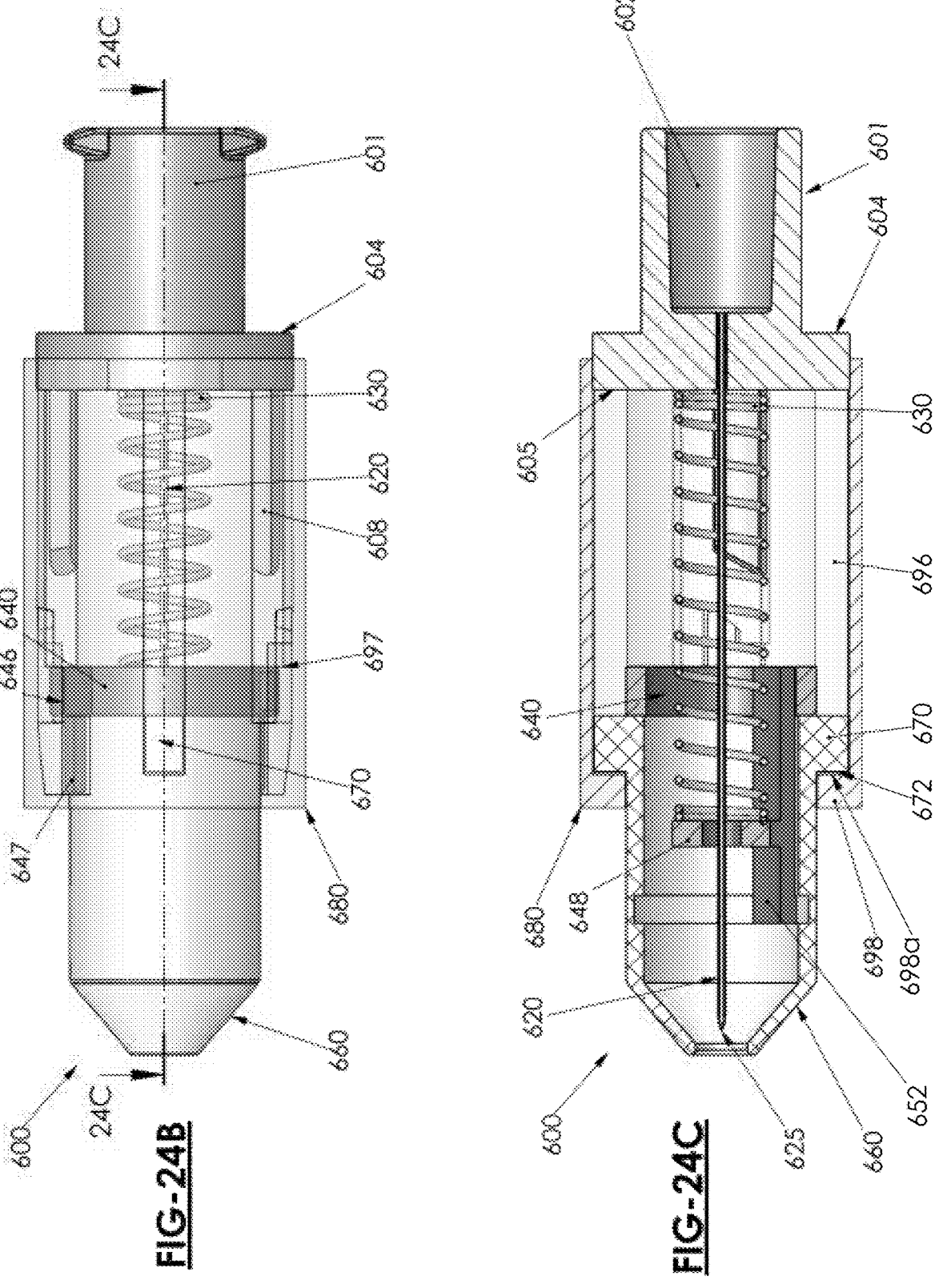
FIG. 24B is a model side view planar illustration of the system of FIG. 24A.
FIG. 24C is a sectional illustration of the system of FIG. 24A, taken along section lines 24C-24C in FIG. 24B.

Reference is now made to FIG. 24A, which is an oriented model view illustration of the system 600, in a locked operative orientation, to FIG. 24B, which is a model side view planar illustration of the system 600 in the locked operative orientation, and to FIG. 24C, which is a sectional illustration of system 600 in the locked operative orientation.

The locked operative orientation occurs automatically immediately following the pre-locking operative orientation, without requiring any additional action by the user. As seen clearly in FIG. 24A, guiding and locking ring 640 rotates under the resilience of fingers 647, such that guiding protrusion 646 and fingers 647 of guiding and locking ring 640 slides along protection surface 692 to locking surface 694 of slot 682. The location of locking surface 694 determines the locking point of system 600.

When system 600 is in the locked position, rearward facing surface 646a of guiding protrusion 646 faces surface 697 of slot 682. It will be appreciated that the distance between surfaces 646a and 697 determines the "give", or maneuverability, of the shield 660 when assembly 600 is in the locked operative orientation. Specifically, a greater distance between the surfaces would allow more movement of shield 660 in the locked operative orientation, whereas smaller distance between the surfaces would allow less, or no, movement of shield 660 in the locked operative orientation. In some embodiments surfaces 646a and 697 may be inclined, in a similar manner to surfaces 547 and 597 of FIG. 18C, and would thus provide higher safety in locking.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

The invention claimed is:

1. A needle protection assembly, adapted to protect a tip of a hypodermic needle, comprising:

a shield adapted, in a protected operative orientation of said needle protection assembly, to shield the tip of the hypodermic needle;

a locking element including at least one slot, said slot including at least three surfaces corresponding to three operative orientations of said shield; said locking element having a base;

at least one slot engaging element, functionally associated with said shield, said slot engaging element being disposed within said slot of said locking element and movable relative thereto, between said surfaces, so as to transition said shield between said three operative orientations and so as to lock said shield in said protected operative orientation; and at least one biasing element, adapted for axial biasing of said shield; said biasing element applying axial force between said base and said one slot engaging element;

wherein said three operative orientations include a storage operative orientation, an injection operative orientation, and said protected operative orientation; and wherein said slot engaging element has a guiding protrusion, which is operative for engaging a first surface of said locking element to transition said shield between said storage operative orientation and said injection operative orientation; and is further operative for engaging a second surface of said locking element, causing relative rotation between said locking element and said slot engaging element, to transition said shield between said injection operative orientation and said protected operative orientation; and wherein said shield is axially displaceable, but not rotatable, relative to said locking element.

2. The assembly of claim 1, wherein said first surface is at least axially or rotationally spaced from said second surface.

3. The assembly of claim 1, wherein relative rotation between said at least one slot engaging element and said locking element allows transitioning between said storage operative orientation and said injection operative orientation.

4. The assembly of claim 1, wherein the guiding protrusion of the slot engaging element is positioned in a different rotational orientation relative to the locking element in each one of said storage operative orientation, injection operative orientation and protected operative orientation.

5. The assembly of claim 1, wherein said slot engaging element includes said guiding protrusion formed on a locking ring, separate from said shield and functionally associated therewith.

6. The assembly of claim 1, wherein said slot engaging element includes a protrusion formed on at least one of a hub of the hypodermic needle, an outer housing surrounding at least one of the hypodermic needle and the shield, and a barrel of a syringe functionally associated with the hypodermic needle.

7. The assembly of claim 1, comprising a locking ring including at least one flexible finger, wherein said flexible finger is not loaded in said storage operative orientation and receives a load during operation of said assembly, and wherein release of said load results in relative rotation between said locking element and said at least one slot engaging element thereby transitioning said assembly into said needle protection operative orientation.

8. The assembly of claim 1, wherein said slot includes at least one inclined surface, such that when said slot engaging element engages said inclined surface there is relative rotation between said slot engaging element and said locking element.

9. The assembly of claim 8, wherein said at least one slot engaging element rotates, thereby providing said relative rotation.

10. The assembly of claim 8, wherein said locking element rotates, thereby providing said relative rotation.

11. The assembly of claim 1, wherein said slot includes an inclined locking surface and said slot engaging element includes a corresponding inclined surface, such that in said protected operative orientation said inclined locking surface of said slot engages said inclined surface of said slot engaging element, thereby increasing safety of locking between said slot engaging element and said slot.

12. The assembly of claim 1, wherein said at least three surfaces include:

a storage surface corresponding to said storage operative orientation;

an end of press surface corresponding to said injection operative orientation; and a locking surface corresponding to said protected operative orientation, wherein said storage surface and said locking surface are at different positions along a longitudinal axis of said assembly.

13. The assembly of claim 1, wherein said slot includes a triggering point, and wherein said transition of said assembly from said storage operative orientation to said injection operative orientation and to said needle protection operative orientation occurs only if pressure applied to said biasing element is sufficient for pushing said slot engaging element past said triggering point.

14. The assembly of claim 13, wherein if said pressure applied to said biasing element is released prior to said slot engaging element passing said triggering point, said assembly returns to said storage operative orientation.

15. The assembly of claim 14, wherein:

said slot includes a one-way triggering passage terminating in said triggering point;

said one-way triggering passage allows passage of said slot engaging element from said storage surface toward said triggering point; and once said slot engaging element has passed said triggering point, said one-way triggering passage blocks passage of said slot engaging element therein toward said storage surface.

16. The assembly of claim 15, wherein:

said slot includes a one-way locking passage terminating in said locking surface;

said one-way locking passage allows passage of said slot engaging element from said end of press surface toward said locking surface; and once said slot engaging element has passed a locking point, said one-way locking passage blocks passage of said slot engaging element therein toward said end of press surface.

17. The assembly of claim 1, further comprising:

a connector for connection of said assembly to a container containing a fluid; and the hypodermic needle in fluid flow communication with said connector and disposed within said assembly at a radial center thereof, wherein, in said storage operative orientation, said tip of said needle protrudes from said shield, and in said protected operative orientation said tip of said needle is locked within said shield.

18. The assembly of claim 17, further comprising a syringe connected to said connector as said container.

19. A needle protection system, comprising:

the needle protection assembly of claim 1; and a hypodermic needle integrally formed with or attached to a syringe, wherein said needle protection assembly is attached to said syringe such that said hypodermic needle is disposed within said assembly at a radial center thereof.

20. The needle protection assembly of claim 1, wherein the hypodermic needle is attached to or integrally formed with a syringe, the assembly further comprising a syringe attachment interface adapted for attachment of said assembly to the syringe, such that when said assembly is attached to the syringe, the hypodermic needle is disposed within said assembly at a radial center thereof.

* * * * *